(12) United States Patent
Ohba et al.

(10) Patent No.: US 7,659,410 B2
(45) Date of Patent: Feb. 9, 2010

(54) THIOPHENE-CONTAINING COMPOUND AND THIOPHENE-CONTAINING COMPOUND POLYMER, ORGANIC ELECTROLUMINESCENT DEVICE, PRODUCTION METHOD THEREOF, AND IMAGE DISPLAY MEDIUM

(75) Inventors: Yoshihiro Ohba, Yamagata (JP); Kazuaki Sato, Yamagata (JP); Mieko Seki, Kanagawa (JP); Hidekazu Hirose, Kanagawa (JP); Takeshi Agata, Kanagawa (JP); Koji Horiba, Kanagawa (JP); Akira Imai, Kanagawa (JP); Tadayoshi Ozaki, Kanagawa (JP); Yohei Nishino, Kanagawa (JP); Hirohito Yoneyama, Kanagawa (JP); Daisuke Okuda, Kanagawa (JP); Toru Ishii, Kanagawa (JP); Kiyokazu Mashimo, Kanagawa (JP); Katsuhiro Sato, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 477 days.

(21) Appl. No.: 11/637,113

(22) Filed: Dec. 12, 2006

(65) Prior Publication Data
US 2007/0252519 A1 Nov. 1, 2007

(30) Foreign Application Priority Data

Apr. 25, 2006 (JP) ............................ 2006-121199
Apr. 25, 2006 (JP) ............................ 2006-121200

(51) Int. Cl.
C07D 333/22 (2006.01)

(52) U.S. Cl. ...................................... 549/77
(58) Field of Classification Search .................... 549/77
See application file for complete search history.

(56) References Cited

U.S. PATENT DOCUMENTS

| | | | |
|---|---|---|---|
| 4,092,162 A | 5/1978 | Wright et al. | |
| 4,801,517 A | 1/1989 | Frechet et al. | |
| 4,806,443 A | 2/1989 | Yanus et al. | |
| 4,806,444 A | 2/1989 | Yanus et al. | |
| 4,937,165 A | 6/1990 | Ong et al. | |
| 4,983,482 A | 1/1991 | Ong et al. | |
| 5,034,296 A | 7/1991 | Ong et al. | |
| 7,153,980 B2 | 12/2006 | Ohba et al. | |
| 2002/0177679 A1 | 11/2002 | Uckert et al. | |
| 2004/0186255 A1 | 9/2004 | Uckert et al. | |
| 2004/0219391 A1 | 11/2004 | Uckert et al. | |

FOREIGN PATENT DOCUMENTS

| | | |
|---|---|---|
| JP | B2 59-28903 | 7/1984 |
| JP | A 61-20953 | 1/1986 |
| JP | A 1-134456 | 5/1989 |
| JP | A 1-134457 | 5/1989 |
| JP | A 1-134462 | 5/1989 |
| JP | A 4-133065 | 5/1992 |
| JP | A 4-133066 | 5/1992 |
| JP | A-04-304466 | 10/1992 |
| JP | A-06-001974 | 1/1994 |

OTHER PUBLICATIONS

P.S. Vincett et al., "Electrical Conduction and Low Voltage Blue Electroluminescence in Vacuum-Deposited Organic Films", Thin Solid Films, vol. 94, 1982, pp. 171-183.

C.W. Tang et al., "Organic Electroluminescent Diodes", Applied Physics Letters, vol. 51, 1987, pp. 913-915.

T. Wakamoto et al., "Organic Electroluminescence Devices with a Starburst Amine as a Hole Transport Material", 40th Meeting Japan Society of Applied Physics and Related Societies, Preprints 30a-SZK-14, 1993, p. 1146.

(Continued)

Primary Examiner—Taofiq A Solola
(74) Attorney, Agent, or Firm—Oliff & Berridge, PLC

(57) ABSTRACT

Provided are a thiophene-containing compound represented by the following formula (X-1), and an organic electroluminescent device that includes a pair of electrodes and an organic compound layer disposed therebetween. The organic compound layer includes a charge-transporting polyester having a repeating structure containing at least one structure selected from the structures represented by the following formulae (I-1) and (I-2) as its partial structure. In formula (X-1), $Ar_1$ represents a substituted or unsubstituted monovalent aromatic group; and $R_1$ to $R_4$ each independently represent a hydrogen atom, a substituted or unsubstituted alkyl group, a substituted or unsubstituted aryl group, or a substituted or unsubstituted aralkyl group; and n' is an integer of 1 to 5.

Formula (X-1)

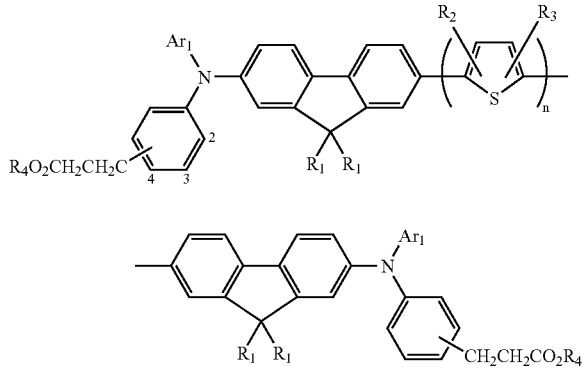

1 Claim, 9 Drawing Sheets

OTHER PUBLICATIONS

M. Sugihara et al., "Synthesis and Physical Properties of Polyphosphazenes Having Hole-Transporting Aromatic Tertiary Amines in Side Chains", Polymer Preprints, 20J-21 Japan, vol. 42, No. 7, 1993, pp. 2860-2862.

G. Gustafsson et al., "Flexible Light-Emitting Diodes Made from Soluble Conducting Polymers", Nature, vol. 357, 1992, pp. 477-479.

Y. Mori et al., "Light-Emitting Characteristics of Organic Electroluminescent Devices with a Mixed-Layer Structure", 38th Meeting Japan Society of Applied Physics & Related Societies, Preprints 31p-G-12, 1991, p. 1086.

T. Mori et al., "Preparation of Organic Electroluminescent Devices by Casting Method and their Evaluation", 50th Meeting Japan Society of Applied Physics, Preprints 29p-ZP-5, 1989, p. 1006.

T. Fujii et al., "Organic EL Devices Having a Cast Polymer Film as a Hole Transport Layer", 51st Meeting Japan Society of Applied Physics, Preprints 28a-PB-7, 1990, p. 1041.

T. Fujii et al., "Organic EL Device Using Evaporated Polymer Film as Hole Transport Layer", 37th Meeting Japan Society of Applied Physics & Related Societies, Preprints 31p-K-12, 1990, p. 1044.

THIOPHENE-CONTAINING COMPOUND AND THIOPHENE-CONTAINING COMPOUND POLYMER, ORGANIC ELECTROLUMINESCENT DEVICE, PRODUCTION METHOD THEREOF, AND IMAGE DISPLAY MEDIUM

BACKGROUND

1. Technical Field

The present invention relates to a thiophene-containing compound and a thiophene-containing compound polymer that are useful for organic electronic devices such as electrophotographic photoreceptor, organic electroluminescent device, and organic transistor. More specifically, it relates to a thiophene-containing compound and a thiophene-containing compound polymer superior in charge-transporting and photoemitting properties. The invention also relates to an organic electroluminescent device using a particular charge-transporting polyester, a method of producing the organic electroluminescent device, and an image display medium using the organic electroluminescent device.

2. Related Art

Regarding electrophotographic photoreceptors, along with recent improvement in performance, organic photoreceptors are used more frequently in high-speed copying machines and printers, but current electrophotographic photoreceptors are insufficient in performance under the circumstance, and thus, there is an urgent demand for elongation of the lifetime. Although there are some charge transport layers in the currently mainstream low-molecular weight dispersion system that almost satisfy the requirements in electrical properties, but the layers still had disadvantages in that they were still lower in mechanical strength and susceptible to abrasion, because a low-molecular weight compound is dispersed in polymer.

Generally, a low-molecular weight charge-transporting material deposited by vacuum deposition is used in the organic electroluminescent device, but there is observed a phenomenon that a great amount of Joule's heat generated by operation at a high current density of several $mA/cm^2$ often causes morphological change of the low-molecular weight charge-transporting material, for example by crystallization, which in turn leads to disadvantages such as deterioration in luminescence brightness, dielectric breakdown, and consequent shortening of device lifetime.

There are various requirements in properties, such as solubility, film-formability, mobility, heat resistance, and matching of oxidation potential, demanded for the charge-transporting material, and thus, to satisfy these requirements, the physical properties thereof are generally modified by introducing a substituent. The physical properties of the charge-transporting polymer have close relationship with the physical properties of the raw material charge-transporting monomer, and thus, molecular design of the charge-transporting monomer, i.e., the low-molecular weight material, is important. The raw material monomers for the triarylamine polymer above include the following two monomers:

(1) Dihydroxyarylamine, and
(2) Bishydroxyalkylarylamine.

However, the dihydroxyarylamine (1) having an aminophenol structure is easily oxidized and thus, hard to purify. In particular, it is less stable when converted into a para-hydroxy substituted structure. Such a compound has a disadvantage that it may be lower in mobility because of uneven distribution of the charge caused by electron withdrawal by the oxygen atom due to the structure in which the oxygen atom is directly bound to the aromatic ring.

On the other hand, the bishydroxyalkylarylamine (2) is less influenced by the electron withdrawal by the oxygen atom because of the methylene group present in the molecule, but is harder to prepare the monomer thereof. Specifically, reaction of a diarylamine or a diarylbenzidine with bromoiodobenzene often gives mixed products because the bromine and iodine atoms are both reactive, resulting in lower yield of desirable product. In addition, the alkyllithium and ethyleneoxide used in replacing bromine with lithium have a problem that they are more hazardous and toxic and demand caution in handling.

Further, organic electroluminescent devices prepared with the $\pi$ conjugation system polymer such as PPV or the polymer containing triphenylamine introduced on the polyphosphazene side chain described above had problems in color tone, light intensity, durability, and others.

For that reason, there exists a need for development of an organic electronic material that is easier to produce and superior in electric charge-transporting efficiency and emission characteristics, in development of organic electronic devices, such as organic electroluminescent devices having greater luminescence brightness and superior in stability during repeated use.

Electroluminescent devices (hereinafter, referred to as "EL devices"), which are self-luminous all-solid-state devices and are superior in visibility and resistant to shock, are expected to find wider application. Inorganic fluorescent materials are mainstream products currently, but these materials demand an AC voltage of 200 V or more for operation, and thus, have problems, for example, in high production cost and insufficient brightness.

SUMMARY

According to an aspect of the invention, there is provided a thiophene-containing compound represented by the following formula (X-1):

Formula (X-1)

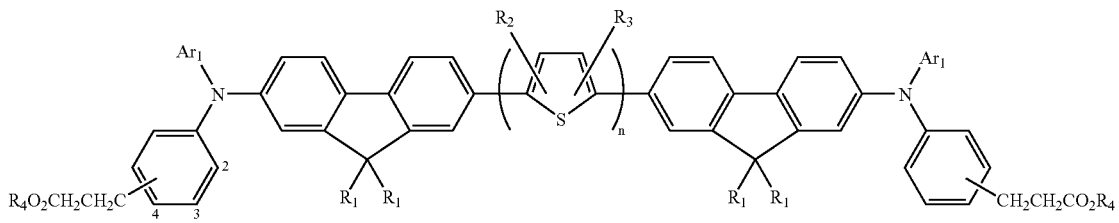

In formula (X-1), $Ar_1$ represents a substituted or unsubstituted monovalent aromatic group; $R_1$ to $R_4$ each independently represent a hydrogen atom, an alkyl group, a substituted or unsubstituted aryl group, or a substituted or unsubstituted aralkyl group; and n represents an integer of 1 to 5.

According to another aspect of the invention, there is provided an organic electroluminescent device including a pair of electrodes composed of an anode and a cathode, and one or more organic compound layers disposed therebetween, at least one of the anode or the cathode being transparent or semitransparent;

at least one of the organic compound layers including a charge-transporting polyester having a repeating structure containing at least one structure selected from the structures represented by the following formulae (I-1) and (I-2) as a partial structure:

Formula (I-1)

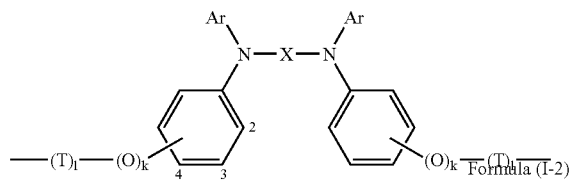

Formula (I-2)

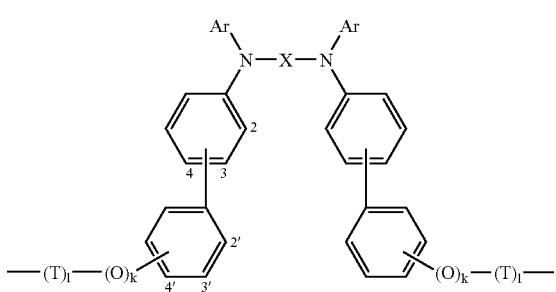

in formulae (I-1) and (I-2), Ar representing a substituted or unsubstituted monovalent phenyl group, a substituted or unsubstituted monovalent polynuclear aromatic hydrocarbon having 2 to 10 aromatic rings, a substituted or unsubstituted monovalent fused aromatic hydrocarbon having 2 to 10 aromatic rings, or a substituted or unsubstituted monovalent aromatic heterocyclic ring; X representing a group represented by the following formula (II); T representing a bivalent straight-chain hydrocarbon group having 1 to 6 carbon atoms or a bivalent branched hydrocarbon group having 2 to 10 carbon atoms; and k and l each independently representing an integer of 0 or 1:

Formula (II)

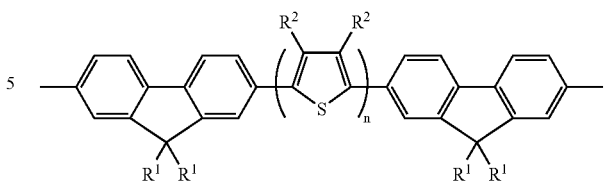

in formula (II), $R^1$ and $R^2$ each independently representing a hydrogen atom, a substituted or unsubstituted alkyl group, a substituted or unsubstituted aryl group, or a substituted or unsubstituted aralkyl group; and n representing an integer of 1 to 10.

BRIEF DESCRIPTION OF THE DRAWINGS

Exemplary embodiments of the present invention will be described in detail based on the following figures, wherein.

DETAILED DESCRIPTION

Figure 1:
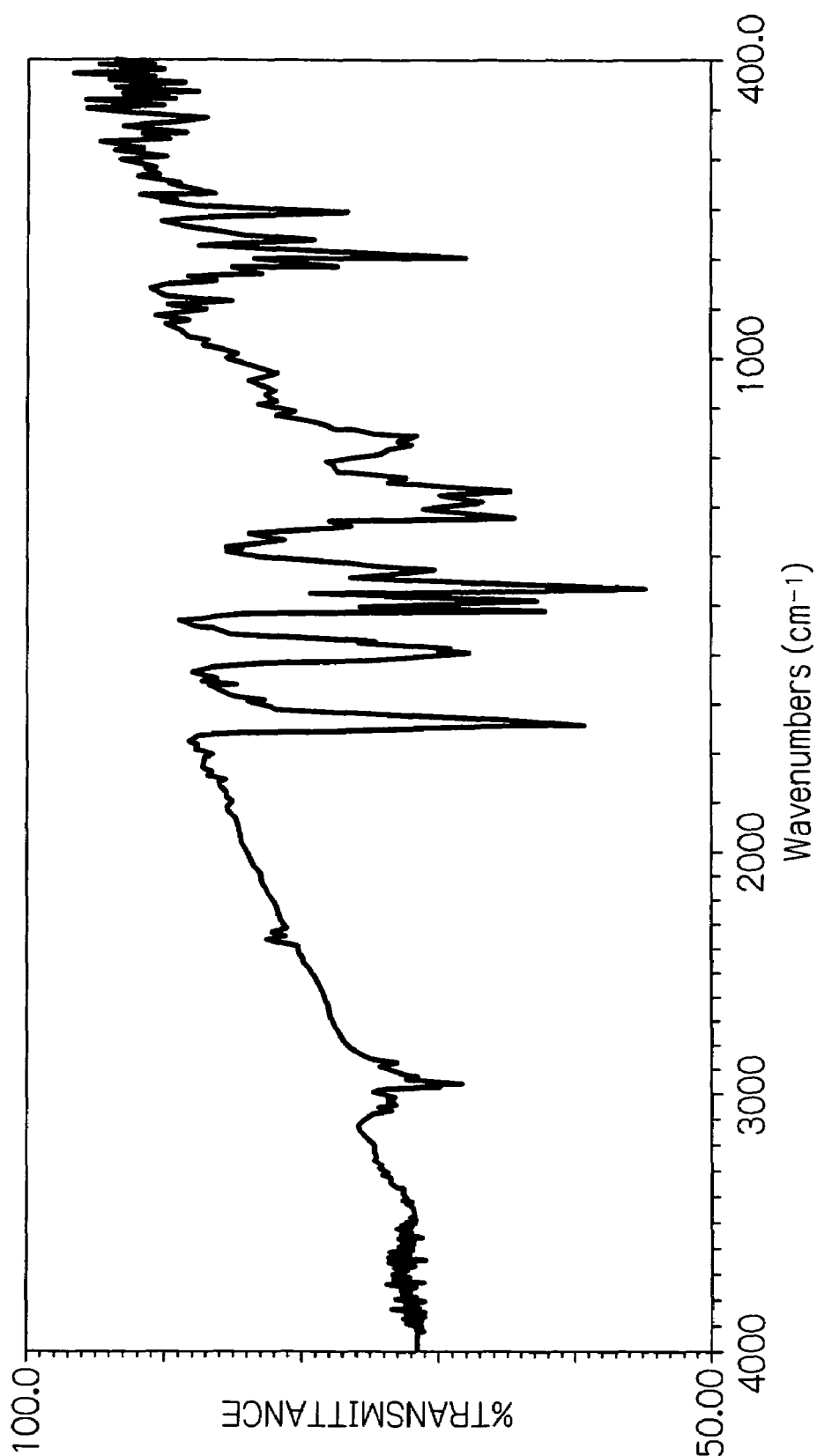
FIG. 1 is the IR spectrum of the compound obtained in Example 1.

The thiophene-containing compound according to an aspect of the invention is a thiophene-containing compound represented by the following formula (X-1).

Formula (X-1)

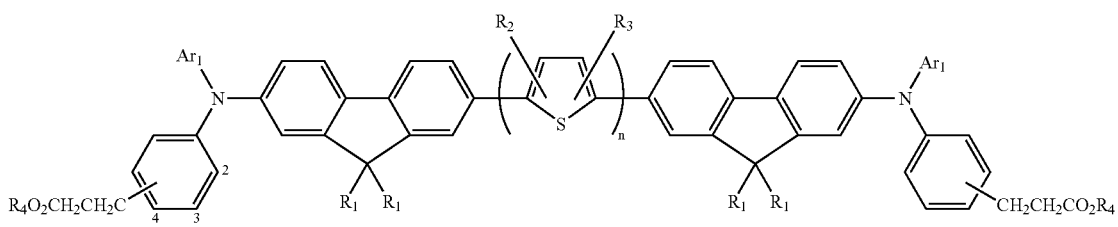

In formula (X-1), $Ar_1$ represents a substituted or unsubstituted monovalent aromatic group; $R_1$ to $R_4$ each independently represent a hydrogen atom, an alkyl group, a substituted or unsubstituted aryl group, or a substituted or unsubstituted aralkyl group; and n is an integer of 1 to 5 (preferably, an integer of 1 to 3).

In formula (X-1) above, $Ar_1$ represents a substituted or unsubstituted monovalent aromatic group; the number of the aromatic or heterocyclic rings are not particularly limited; and specific examples thereof include substituted or unsubstituted phenyl groups, substituted or unsubstituted monovalent polynuclear aromatic hydrocarbons having 2 to 20 aromatic rings, substituted or unsubstituted monovalent fused aromatic hydrocarbons having 2 to 20 aromatic rings, substituted or unsubstituted monovalent aromatic heterocyclic rings, and substituted or unsubstituted monovalent aromatic group having at least one aromatic heterocyclic ring.

The polynuclear aromatic hydrocarbon means specifically a polycyclic aromatic compound defined below in an aspect of the invention. In addition, the fused aromatic hydrocarbon means specifically a polycyclic aromatic compound defined below in an aspect of the invention. Thus, the "polynuclear aromatic hydrocarbon" is a hydrocarbon containing two or more aromatic rings consisting of carbon and hydrogen atoms that are bound to each other via a carbon-carbon bond. Specific examples thereof include biphenyl, terphenyl, and stilbene.

The "fused aromatic hydrocarbon" is a hydrocarbon compound having two or more aromatic rings consisting of carbon and hydrogen atoms wherein neighboring aromatic rings among the two or more aromatic rings share a pair of vicinal carbon atoms that are bonded to each other. Specificl examples thereof include naphthalene, anthracene, phenanthrene, pyrene, perylene, and fluorene.

Further in formula (X-1), the aromatic heterocyclic ring selected as a possible structure represented by $Ar_1$ is an aromatic ring containing an element other than carbon and hydrogen. The number of the atoms constituting the ring skeleton (Nr) may be, for example, 5 or 6. The kind and the number of the atoms other than carbon (hetero atoms) in the ring skeleton are not particularly limited, but, for example, a sulfur atom, a nitrogen atom, an oxygen atom, or the like may be used, and the ring skeleton may include two or more kinds of hetero atom, and may include two or more hetero atoms. Examples of heterocyclic rings having a five-membered ring structure include thiophene, thiofin, pyrrole, furan, and a heterocyclic ring obtained by replacing the carbons at the 3- and 4-positions of any of such rings with a nitrogen atom, and examples of heterocyclic rings having a six-membered structure include a pyridine ring.

Further in formula (X-1), the aromatic group containing the aromatic heterocyclic ring selected as a possible structure represented by $Ar_1$ represents a bond group containing at least one of the aromatic heterocyclic rings described above in the atom group forming the skeleton. Although the ring may be entirely or partially conjugated, it is preferably an entirely conjugated system, from the points of charge-transporting efficiency and luminous efficiency.

In formula (X-1), examples of a substituent on the monovalent aromatic group represented by $Ar_1$ include a hydrogen atom, alkyl groups, alkoxy groups, a phenoxy group, aryl groups, aralkyl groups, substituted amino groups, and halogen atoms.

The alkyl group to be substituted on the monovalent aromatic group may be an alkyl group having 1 to 10 carbon atoms, and examples thereof include a methyl group, an ethyl group, a propyl group, and an isopropyl group. The alkoxy group to be substituted on the monovalent aromatic group may be an alkoxy group having 1 to 10 carbon atoms, and examples thereof include a methoxy group, an ethoxy group, a propoxy group, and an isopropoxy group.

The aryl group to be substituted on the monovalent aromatic group may be an aryl group having 6 to 20 carbon atoms, and examples thereof include a phenyl group and a toluyl group.

The aralkyl group to be substituted on the monovalent aromatic group may be an aralkyl group having 7 to 20 carbon atoms, and examples thereof include a benzyl group and a phenethyl group.

The substituent on the substituted amino group to be substituted on the monovalent aromatic group may be an alkyl group, an aryl group, or an aralkyl group, and specific examples thereof include those mentioned in the above explanation of the alkyl, aryl, and aralkyl groups.

The alkyl group represented by any of $R_1$ to $R_4$ in formula (X-1) may be an alkyl group having 1 to 10 carbon atoms, and examples thereof include a methyl group, an ethyl group, a propyl group, and an isopropyl group.

The aryl group represented by any of $R_1$ to $R_4$ may be an aryl group having 6 to 20 carbon atoms, and examples thereof include a phenyl group and a toluyl group.

The aralkyl group represented by any of $R_1$ to $R_4$ may be an aralkyl group having 7 to 20 carbon atoms, and examples thereof include a benzyl group and a phenethyl group.

Examples of the substituents on the alkyl group, aryl group, or aralkyl group include alkyl groups, aryl groups, and aralkyl groups. Specific examples thereof are as described above.

Hereinafter, exemplary compounds 1 to 37 are shown in Tables 1 to 4 as specific examples of the thiophene-containing compound according to an aspect of the invention, which are compounds having a structure represented by formula (X-1), but the invention is not limited thereto. The specific examples described in Table 1 to 4 are bilaterally symmetric with the central thiophene at the middle. In Tables 1 to 4, the first column from the left indicates the exemplary compound number; the second column indicates $Ar_1$ in formula (X-1); the third column indicates $R_1$ in formula (X-1); the fourth column indicates $R_4$ in formula (X-1); the fifth column indicates the thiophene in formula (X-1) (the structure shown in the first row in Table 1); and the sixth column indicates the binding site of "$R_4CH_2CH_2C$—" in formula (X-1).

TABLE 1

| No. | $Ar_1$ | $R_1$ | $R_4$ | 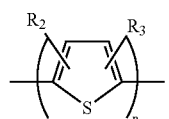 | Bonding Position |
|---|---|---|---|---|---|
| 1 | 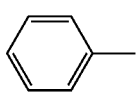 | H | $CH_3$ | 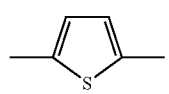 | 3 |

TABLE 1-continued
| No. | Ar₁ | R₁ | R₄ | (thiophene group with R₂, R₃) | Bonding Position |
|---|---|---|---|---|---|
| 2 | 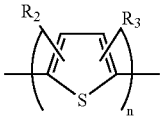 | CH₃ | CH₃ | 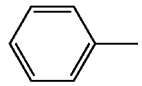 | 4 |
| 3 | 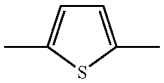 | n-C₃H₇ | CH₃ | 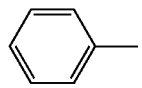 | 4 |
| 4 | 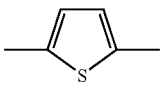 | CH₃ | CH₃ | 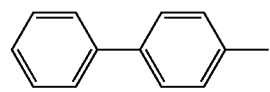 | 4 |
| 5 | 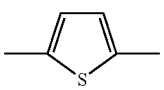 | CH₃ | CH₃ | 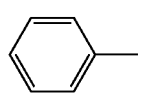 | 4 |
| 6 | 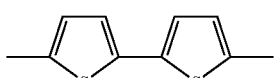 | n-C₃H₇ | CH₃ | 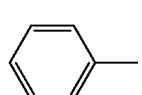 | 4 |
| 7 | 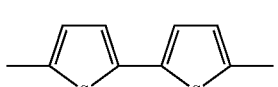 | CH₃ | CH₃ | 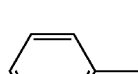 | 4 |
| 8 | 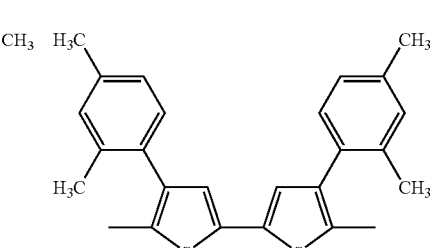 | CH₃ | CH₃ | 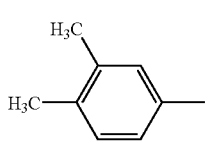 | 4 |
| 9 | 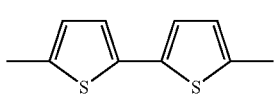 | C₃H₁₃ | CH₃ | 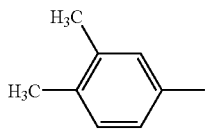 | 4 |
| 10 | 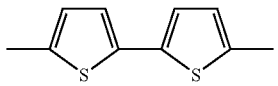 | H | C₂H₅ | 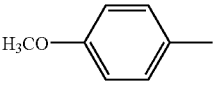 | 4 |
| 11 | 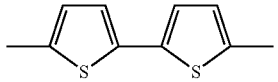 | CH₃ | CH₃ | 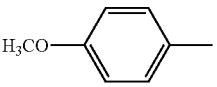 | 3 |
TABLE 2
| 12 | 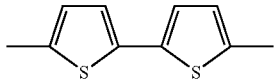 | CH₃ | CH₃ | 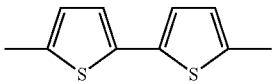 | 4 |

TABLE 2-continued
| | | | | | |
|---|---|---|---|---|---|
| 13 | 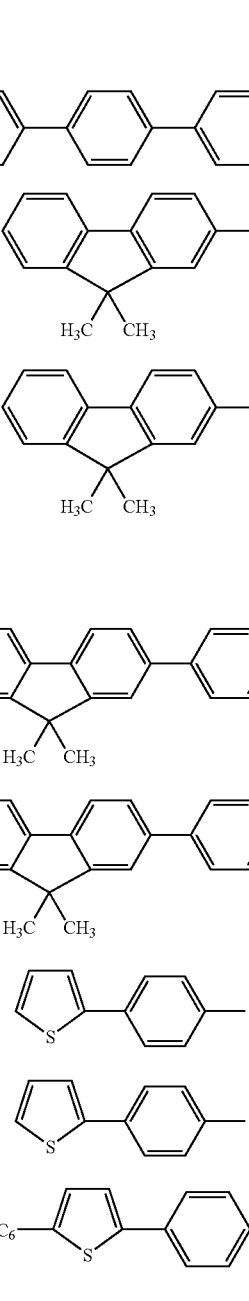 | CH$_3$ | CH$_3$ | 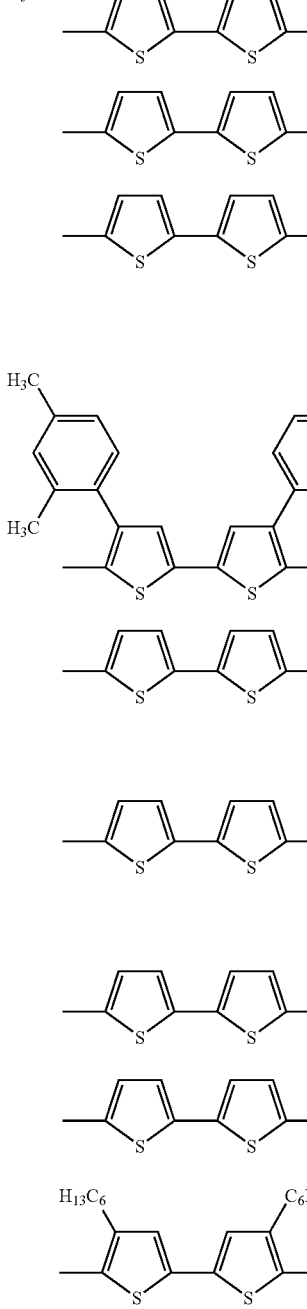 | 4 |
| 14 | 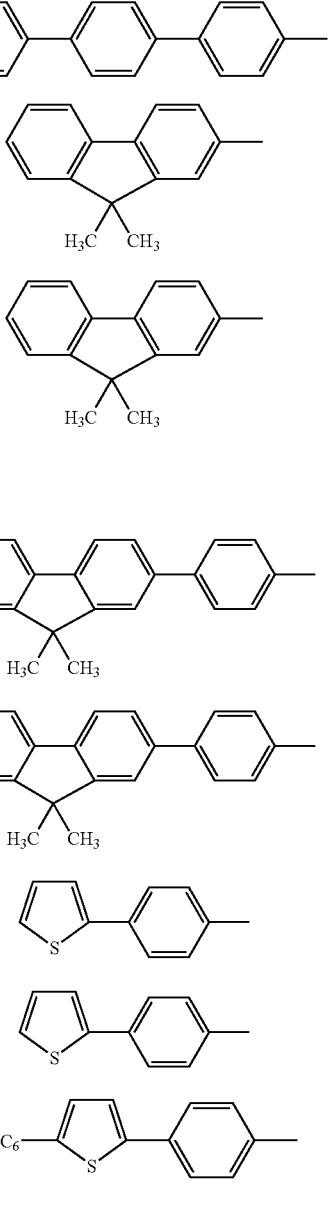 | CH$_3$ | CH$_3$ | 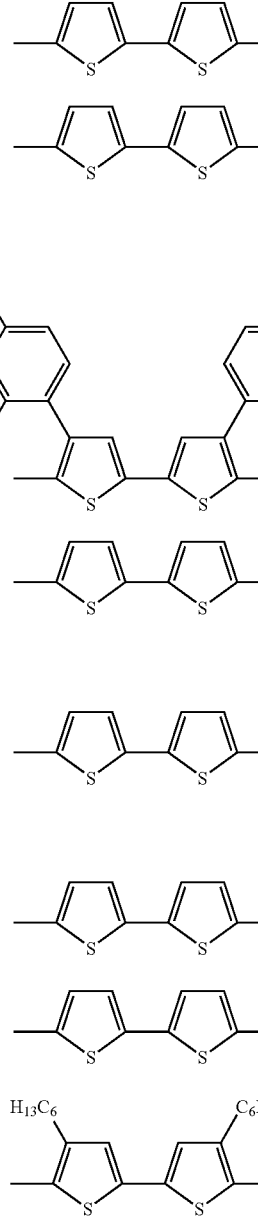 | 4 |
| 15 | 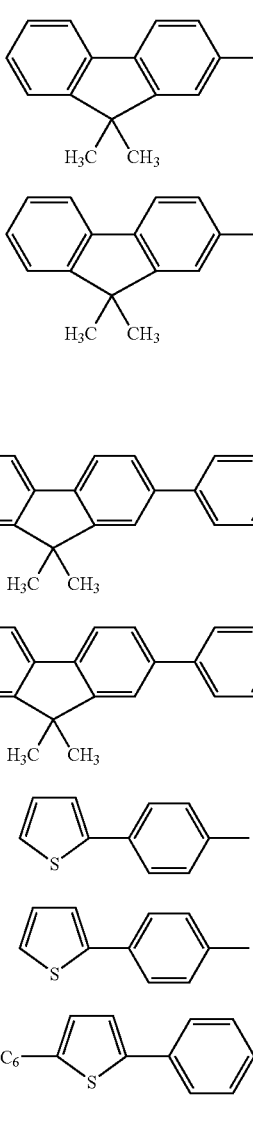 | CH$_3$ | CH$_3$ | 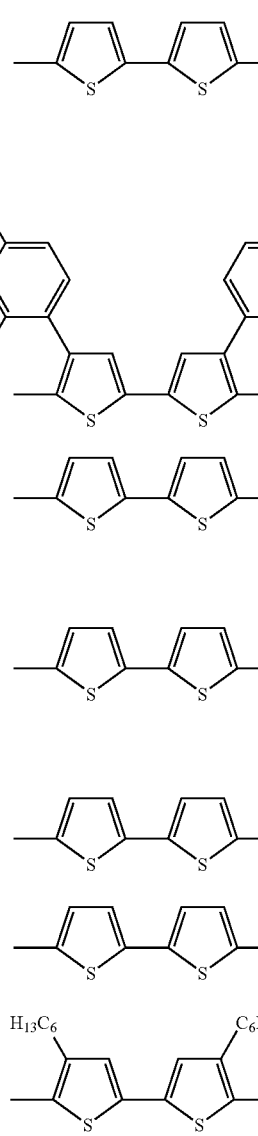 | 4 |
| 16 | 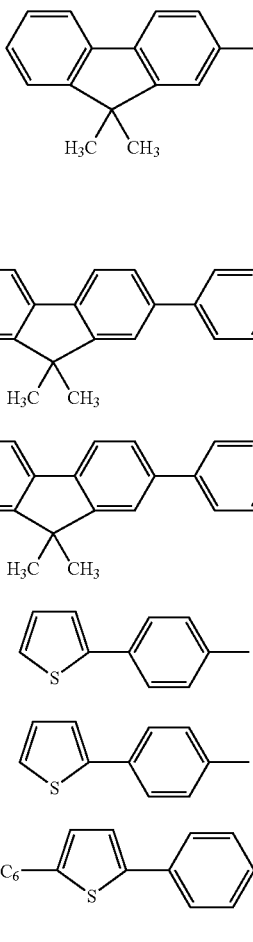 | CH$_3$ | CH$_3$ | 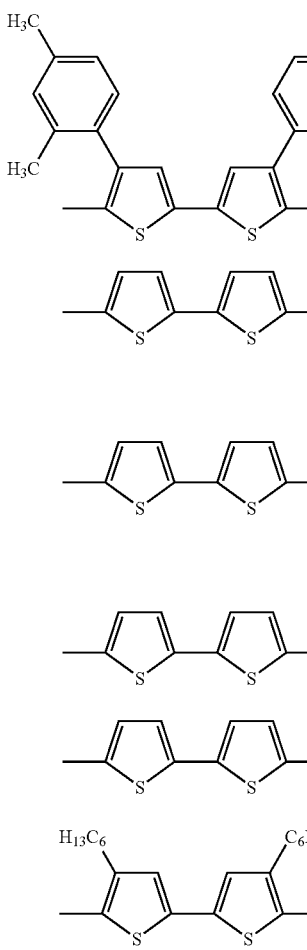 | 4 |
| 17 | 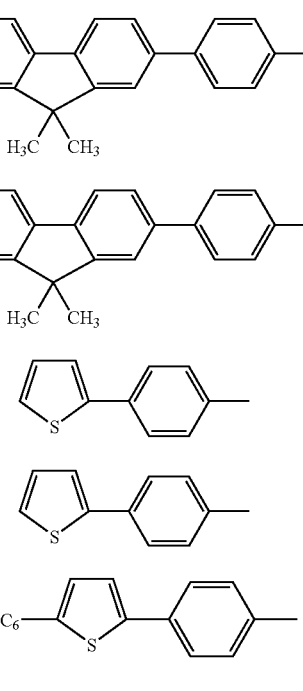 | CH$_3$ | CH$_3$ | 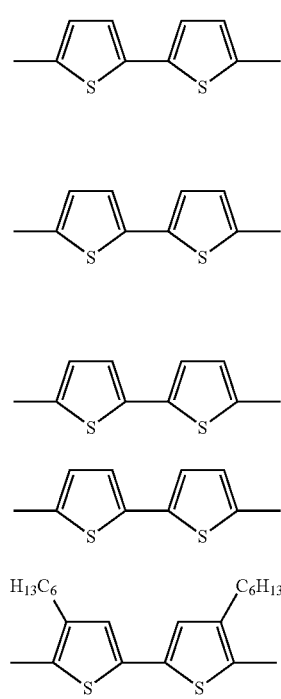 | 4 |
| 18 | 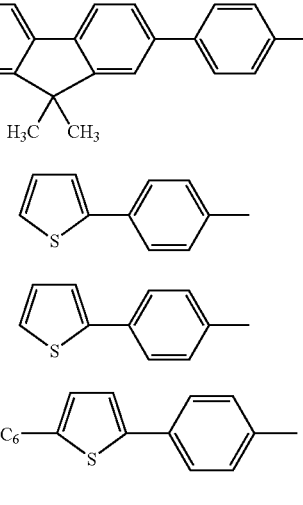 | i-C$_3$H$_7$ | CH$_3$ | 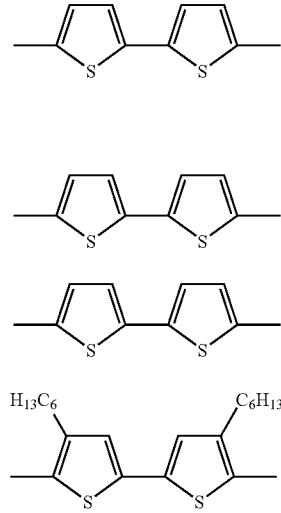 | 4 |
| 19 | 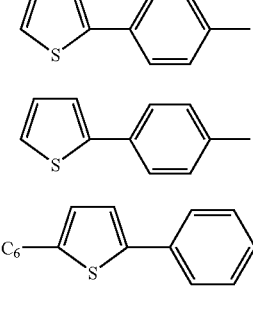 | CH$_3$ | CH$_3$ | 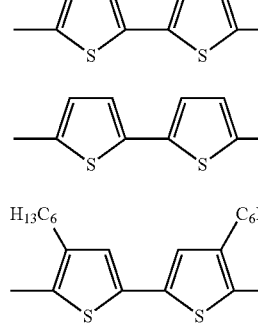 | 4 |
| 20 | 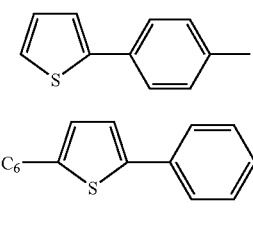 | i-C$_3$H$_7$ | CH$_3$ | 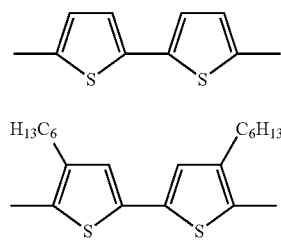 | 4 |
| 21 | 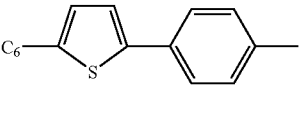 | CH$_3$ | CH$_3$ | 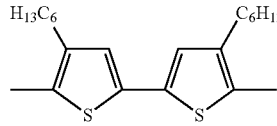 | 4 |
| 22 |  | CH$_3$ | CH$_3$ |  | 4 |

TABLE 3

| # | Structure 1 | R1 | R2 | Structure 2 | n |
|---|---|---|---|---|---|
| 23 | 5-hexyl-thienyl-9,9-dimethylfluorenyl | CH₃ | CH₃ | bis(2,4-dimethylphenyl)-5,5'-dimethyl-2,2'-bithiophene | 4 |
| 24 | 4-methoxy-3-methylbiphenyl | H | CH₃ | 5,5'-dimethyl-2,2'-bithiophene | 4 |
| 25 | 4-methoxy-3-methylbiphenyl | H | CH₃ | bis(2,4-dimethylphenyl)-5,5'-dimethyl-2,2'-bithiophene | 4 |
| 26 | 1-naphthyl | CH₃ | CH₃ | 5,5'-dimethyl-2,2'-bithiophene | 4 |
| 27 | 9-phenanthryl | CH₃ | C₂H₅ | 5,5'-dimethyl-2,2'-bithiophene | 4 |
| 28 | 1-pyrenyl | H | CH₃ | 5,5'-dimethyl-2,2'-bithiophene | 4 |
| 29 | (E)-2-(4-methylstyryl)thiophene | CH₃ | CH₃ | 5,5'-dimethyl-2,2'-bithiophene | 4 |
| 30 | 5'-hexyl-5-[(E)-4-methylstyryl]-2,2'-bithiophene | CH₃ | CH₃ | 5,5'-dimethyl-2,2'-bithiophene | 4 |
| 31 | 2-(thiophen-2-yl)-3-(4-methylphenyl)maleonitrile | CH₃ | CH₃ | 5,5'-dimethyl-2,2'-bithiophene | 4 |

TABLE 3-continued

| 32 |  | CH₃ | CH₃ |  | 4 |
| 33 |  | CH₃ | CH₃ |  | 4 |

TABLE 4

| 34 |  | H | CH₃ | 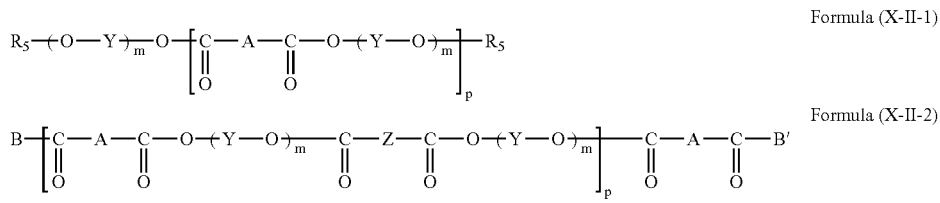 | 4 |
| 35 |  | CH₃ | CH₃ | 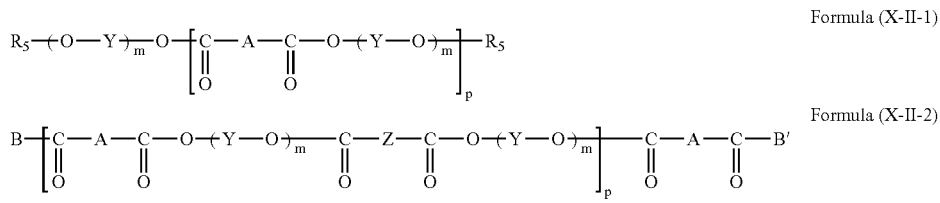 | 4 |
| 36 |  | H | CH₃ | 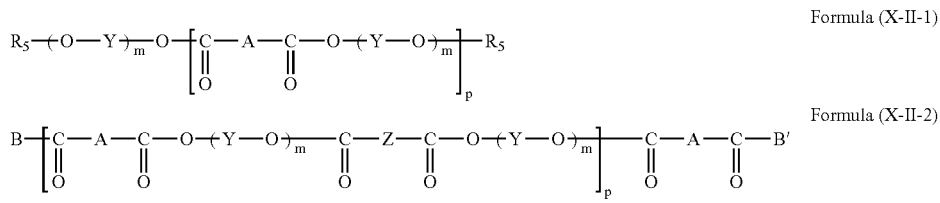 | 4 |
| 37 |  | CH₃ | CH₃ | 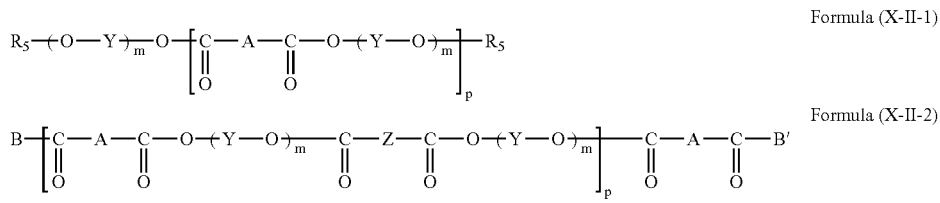 | 4 |

The thiophene-containing compound polymer according to an aspect of the invention is a thiophene-containing compound represented by the following formula (X-II-1) or (X-II-2).

Formula (X-II-1)

$$R_5\!-\!\!(\!O\!-\!Y\!)_m\!-\!O\!-\!\!\left[\!-\!\overset{\scriptscriptstyle O}{\underset{\scriptscriptstyle \|}{C}}\!-\!A\!-\!\overset{\scriptscriptstyle O}{\underset{\scriptscriptstyle \|}{C}}\!-\!O\!-\!(\!Y\!-\!O\!)_m\!-\!\right]_p\!\!-\!R_5$$

Formula (X-II-2)

$$B\!-\!\!\left[\!-\!\overset{\scriptscriptstyle O}{\underset{\scriptscriptstyle \|}{C}}\!-\!A\!-\!\overset{\scriptscriptstyle O}{\underset{\scriptscriptstyle \|}{C}}\!-\!O\!-\!(\!Y\!-\!O\!)_m\!-\!\overset{\scriptscriptstyle O}{\underset{\scriptscriptstyle \|}{C}}\!-\!Z\!-\!\overset{\scriptscriptstyle O}{\underset{\scriptscriptstyle \|}{C}}\!-\!O\!-\!(\!Y\!-\!O\!)_m\!-\!\right]_p\!-\!\overset{\scriptscriptstyle O}{\underset{\scriptscriptstyle \|}{C}}\!-\!A\!-\!\overset{\scriptscriptstyle O}{\underset{\scriptscriptstyle \|}{C}}\!-\!B'$$

In formulae (X-II-1) and (X-II-2), Y represents a bivalent hydrocarbon group; $R_5$ represents a hydrogen atom, a substituted or unsubstituted alkyl group, a substituted or unsubstituted aryl group, or a substituted or unsubstituted aralkyl group. Z represents a bivalent hydrocarbon group. m is a an integer of 1 to 5 (preferably, an integer of 1 to 3). p is an integer of 5 to 5,000. B and B' each independently represent —O—(Y'—O)$_{m2}$—H, or —O—(Y'—O)$_{m2}$—CO-Z'—CO—OR$_6$. Y' and Z' each independently represent a bivalent hydrocarbon group; m2 is an integer of 1 to 5; and $R^6$ represents a hydrogen atom, a substituted or unsubstituted alkyl group, a substituted or unsubstituted aryl group, or a substituted or unsubstituted aralkyl group. A represents a group represented by the following formula (X-III).

Formula (X-III)

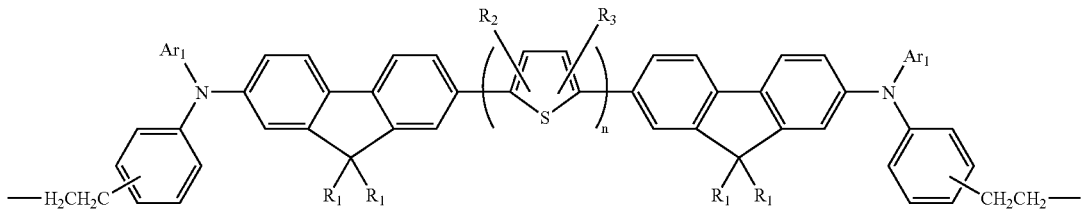

In formula (X-III), Ar₁ represents a substituted or unsubstituted monovalent aromatic group; $R_1$ to $R_3$ each independently represent a hydrogen atom, a substituted or unsubstituted alkyl group, a substituted or unsubstituted aryl group, or a substituted or unsubstituted aralkyl group; and n is an integer of 1 to 5.

The bivalent hydrocarbon group represented by Y or Z in formulae (X-II-1) and (X-II-2) is a group selected from the groups represented by the following formulae (IV-1) to (IV-7).

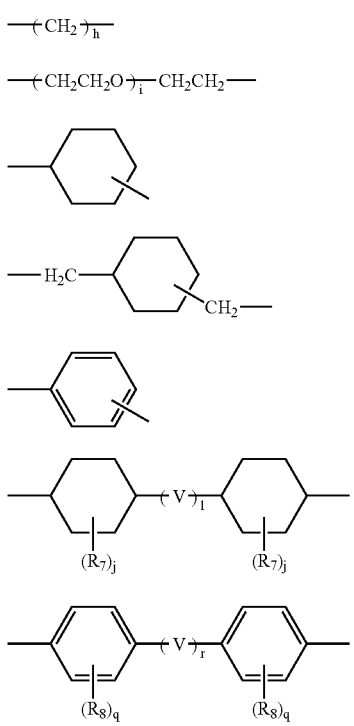

In structural formulae (IV-1) to (IV-7), $R_7$ and $R_8$ each independently represent a hydrogen atom, a substituted or unsubstituted alkyl group having 1 to 4 carbon atoms, a substituted or unsubstituted alkoxy group having 1 to 4 carbon atoms, a substituted or unsubstituted phenyl group, or a substituted or unsubstituted aralkyl group; each of h and i is independently an integer of 1 to 5; each of l and r is independently 0 or 1; each of q and j is an integer of 0 to 2, and V represents a group selected from the following formulae (V-1) to (V-11).

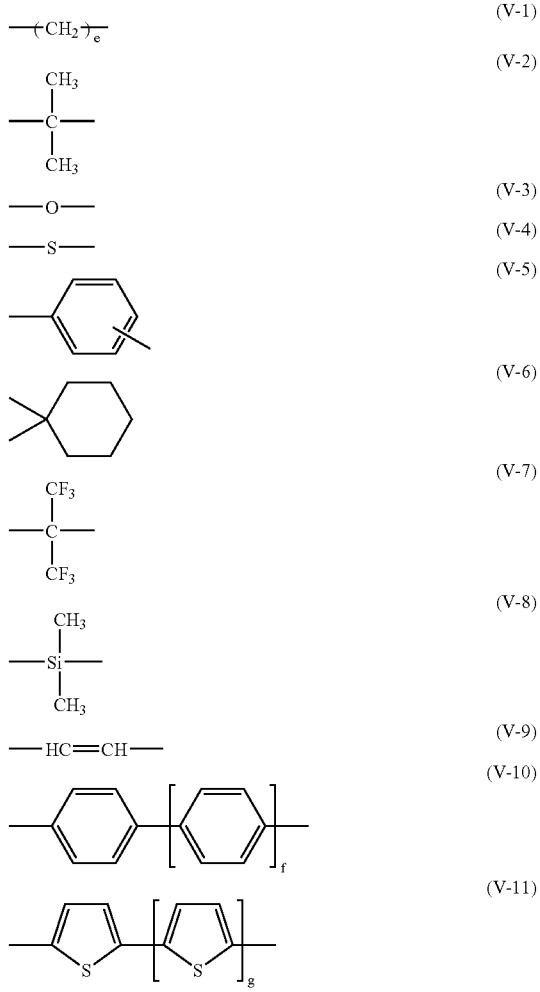

In structural formulae (V-1), (V-10) and (V-11), e is an integer of 1 to 5; and each of f and g is an integer of 0 to 5.

The polymerization degree p of the thiophene-containing compound polymer represented by formula (X-II-1) or (X-II-2) may be in the range of 5 to 5,000, preferably in the range of 10 to 1,000, from the points of film-formability, device stability, and others. The weight-average molecular weight Mw thereof is preferably in the range of 10,000 to 300,000.

$R_5$ in formula (X-II-1) has the same definition as $R_1$ to $R_4$ in formula (X-1), and examples thereof may be also the same.

Each of B and B' in formula (X-II-2) represents —O—(Y'—O)$_{m2}$—H, or —O—(Y'—O)$_{m2}$—CO-Z'-CO—OR$_6$. Y', Z', and m2 has the same definitions as above-described Y, Z, and m respectively, and examples thereof may be also the same.

$R_6$ has the same definition as $R_5$ above, and examples thereof may be also the same.

On the other hand, $Ar_1$, $R_1$ to $R_4$, and n in formula (X-III) have the same definition as $Ar_1$, $R_1$ to $R_4$, and n in formula (X-1) respectively, and examples thereof may be also the same.

Hereinafter, exemplary compounds (1) to (41) are shown in Tables 5 to 6 as specific examples of the thiophene-containing compound polymer represented by formula (X-II-1) or (X-II-2), but the invention is not limited thereto. Among the specific examples shown in Tables 5 to 6, if the column for Z—the fifth column from the left—is blank, the compound is a specific example of the thiophene-containing compound polymer represented by formula (X-II-1). If the column for Z—the fifth column from the left—is filled, the compound is a specific examples of the thiophene-containing compound polymer represented by formula (X-II-2). The first column from the left in Tables 68 to 69 indicate an exemplary compound number; the second column indicates A in formula (X-III), the number described therein corresponding to the exemplary compound number in Tables 1 to 4; and the group A mentioned therein is a group obtained by removing the groups "$CO_2R_4$" from both ends of the exemplary compound having the indicated exemplary compound number to acquire bondability. When there are multiple groups for A, the third column from the left shows the molar ratio between the groups. The fourth column from the left shows Y in formula (X-II-1) or (X-II-2). The fifth column from the left shows Z in formula (X-II-2). The sixth column from the left shows $R_5$ when the compound is a specific example of the thiophene-containing compound polymer represented by formula (X-II-1) (i.e., when the column for Z is blank), and shows B and B' when it is a specific example of the thiophene-containing compound polymer represented by formula (X-II-2). The seventh column from the left shows m in formula (X-II-1) or (X-II-2). The eighth column from the left shows p in formula (X-II-1) or (X-II-2).

TABLE 5

| No. | A No. | A Ratio | Y | Z | $R_5$/B, B' | m | p |
|---|---|---|---|---|---|---|---|
| (1) | 5 | — | —CH₂CH₂— | — | H | 1 | 173 |
| (2) | 5 | — | 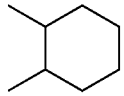 | — | H | 1 | 98 |
| (3) | 5 | — | 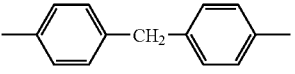 | — | H | 1 | 75 |
| (4) | 5 | — | —CH₂CH₂— |  | OCH₂CH₂OH | 1 | 95 |
| (5) | 5 | — | —CH₂CH₂— | —(CH₂)₄— | OCH₂CH₂OH | 1 | 145 |
| (6) | 6 | — | —CH₂CH₂— | — | H | 1 | 83 |
| (7) | 8 | — | 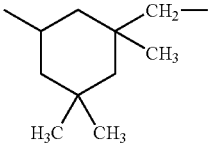 | — | H | 1 | 101 |
| (8) | 12 | — | —CH₂CH₂— | — | H | 1 | 78 |
| (9) | 12 | — | 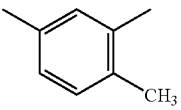 | — | H | 1 | 46 |
| (10) | 15 | — | —CH₂CH₂— | — | H | 1 | 173 |
| (11) | 17 | — |  | — | H | 1 | 56 |
| (12) | 20 | — | —CH₂CH₂— | — | H | 1 | 102 |

TABLE 5-continued
| No. | A No. | A Ratio | Y | Z | R5/B, B' | m | p |
|---|---|---|---|---|---|---|---|
| (13) | 20 | — | 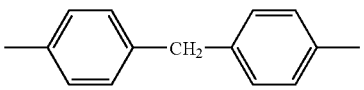 | — | H | 1 | 48 |
| (14) | 22 | — | —CH₂CH₂— | — | H | 1 | 59 |
| (15) | 22 | — | —(CH₂)₆— | — | H | 1 | 85 |
| (16) | 22 | — | —CH₂CH₂— | 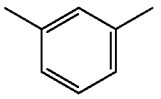 | OCH₂CH₂OH | 1 | 102 |
| (17) | 23 | — | —CH₂CH₂— | — | H | 1 | 64 |
| (18) | 23 | — | 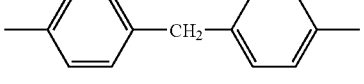 | — | H | 1 | 45 |
| (19) | 23 | — | —CH₂CH₂— | 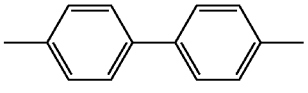 | OCH₂CH₂OH | 1 | 148 |
| (20) | 24 | — | —CH₂CH₂— | — | H | 1 | 68 |
TABLE 6
| (21) | 26 | — | —CH₂CH₂— | — | H | 1 | 96 |
|---|---|---|---|---|---|---|---|
| (22) | 26 | — | —(CH₂)₆— | — | H | 1 | 79 |
| (23) | 26 | — | 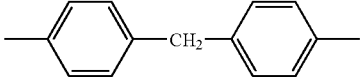 | — | H | 1 | 100 |
| (24) | 26 | — | —CH₂CH₂— |  | OCH₂CH₂OH | 1 | 86 |
| (25) | 27 | — | —CH₂CH₂— | — | H | 1 | 112 |
| (26) | 29 | — | —CH₂CH₂— | — | H | 1 | 72 |
| (27) | 29 | — | 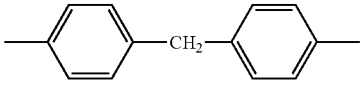 | — | H | 1 | 102 |
| (28) | 29 | — | 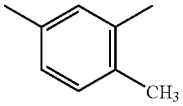 | — | H | 1 | 100 |
| (29) | 30 | — | —CH₂CH₂— | — | H | 1 | 67 |
| (30) | 30 | — | —(CH₂)₆— | — | H | 1 | 87 |
| (31) | 32 | — | 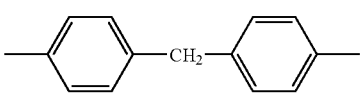 | — | H | 1 | 86 |

TABLE 6-continued

| | | | | | | | |
|---|---|---|---|---|---|---|---|
| (32) | 32 | — | 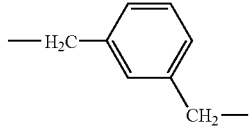 | — | H | 1 | 96 |
| (33) | 34 | — | —CH$_2$CH$_2$— | — | H | 1 | 75 |
| (34) | 34 | — | —(CH$_2$)$_6$— | — | H | 1 | 96 |
| (35) | 36 | — | —CH$_2$CH$_2$— | — | H | 1 | 93 |
| (36) | 36 | — | 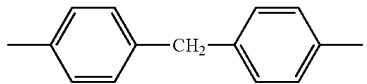 | — | H | 1 | 89 |
| (37) | 1/10 | 1/1 | —CH$_2$CH$_2$— | — | H | 1 | 77 |
| (38) | 1/10 | 1/1 | 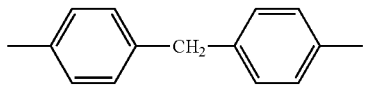 | — | H | 1 | 110 |
| (39) | 1/14 | 1/1 | —CH$_2$CH$_2$— | — | H | 1 | 106 |
| (40) | 14/17 | 1/1 | —CH$_2$CH$_2$— | — | H | 1 | 100 |
| (41) | 14/24 | 1/1 | —CH$_2$CH$_2$— | — | H | 1 | 66 |

The thiophene-containing compound and the thiophene-containing compound polymer according to an aspect of the invention are prepared, for example, in the following manner:

(1) A diarylamine is prepared in reaction of an arylamine with a halogenated carbalkoxyalkylbenzene or in reaction of an aryl halide with a carboalkoxyaniline, and the diarylamine is then allowed to react with a bis-halogenated aryl.

(2) A diarylamine is prepared in reaction of an arylamine or a benzidine derivative with a halogenated carbalkoxyalkyl-benzene, and the diarylamine is allowed to react with an aryl halide.

A method of preparing a charge-transporting material containing an alkylene carboxylic ester group is described in JP-A No. 5-80550, the method including introducing a chloromethyl group, forming its Grignard reagent with Mg, converting it into a carboxylic acid with carbon dioxide, and esterifying the product. However, it is not possible by the method to introduce the chloromethyl group into the raw material at the initial phase because the reactivity of the chloromethyl group is high. Accordingly, the following scheme is required: i) chloromethylate the methyl group introduced, for example, into the raw material in the early stage after formation of a skeleton such as triarylamine or tetraarylbenzidine; or ii) use an unsubstituted raw material in the raw material stage, introduce a functional group such as a formyl group into the aromatic ring in substitution reaction after formation of a tetraarylbenzidine skeleton, reduce it into alcohol, and convert it into a chloromethyl group by using a halogenating agent such as thionyl chloride; or iii) directly chloromethylate the skeleton, for example, with paraformaldehyde and hydrochloric acid.

However, because charge-transporting materials having a skeleton such as triarylamine or tetraarylbenzidine are highly reactive, use of the method of chloromethylating a previously introduced methyl group often results in halogen substitution on the aromatic ring, and thus, it is practically impossible to chlorinate only the methyl group selectively. In addition, use of the method of using an unsubstituted raw material, introducing a functional group such as a formyl group and then converting it into a chloromethyl group or the method of direct chloromethylation often results in introduction of the chloromethyl group only at the position para to the nitrogen atom, and consequently, the alkylene carboxylic ester group is also introduced only at the position para to the nitrogen atom.

In addition, the method of introducing a formyl group and then converting it into a chloromethyl group has more reaction steps. In contrast, the method of obtaining a monomer in reaction of an arylamine, a diarylbenzidine, or the like with a halogenated carbalkoxyalkylbenzene, which is advantageous in that it is easy to modify the position of the substituent and control the ionization potential or the like, enables control of the resultant compound. The monomer used in the preparation in an aspect of the invention enables easy introduction of various substituents at arbitrary positions and is chemically stable and easy to handle, and thus reduces the problems described above.

The method of producing a thiophene-containing compound according to an aspect of the invention will be described specifically below. In an aspect of the invention, for example, a diarylamine represented by the following formula (X-X) can be prepared in coupling reaction of a halogenated compound represented by the following formula (X-VI) and an acetamide compound represented by the following formula (X-VII) in the presence of a copper catalyst or in coupling reaction of an acetamide compound represented by the following formula (X-VIII) with a halogenated compound represented by the following formula (X-IX) in the presence of a copper catalyst, and then, a thiophene compound is obtained in coupling reaction of the diarylamine (X) with a dihalogenated compound represented by the following formula (X-XI) in the presence of a copper catalyst.

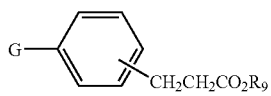

Formula (X-VI)

[in formula (X-VI), $R_9$ represents a hydrogen atom, an alkyl group, a substituted or unsubstituted aryl group, or a substituted or unsubstituted aralkyl group; and G represents a bromine or iodine atom].

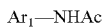

Formula (X-VII)

[in formula (X-VII), $Ar_1$ has the same definition as $Ar_1$ in formula (X-1) or (X-III) and exemplary range thereof may be also the same; and Ac represents an acetyl group].

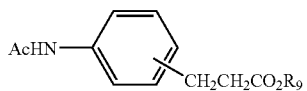

Formula (X-VIII)

[in formula (X-VIII), $R^9$ represents a hydrogen atom, an alkyl group, a substituted or unsubstituted aryl group, or a substituted or unsubstituted aralkyl group; and Ac represents an acetyl group].

Formula (X-IX)

[in formula (X-IX), $Ar_1$ has the same definition as $Ar_1$ in formula (X-1) or (X-III), and exemplary range thereof may be also the same; and G has the same definition as G in formula (X-VI), and exemplary range thereof may be also the same].

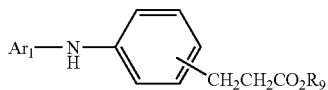

Formula (X-X)

[In formula (X-X), $Ar_1$ has the same definition as $Ar_1$ in formula (X-1) or (X-III), and exemplary range thereof may be also the same; and $R_9$ has the same definition as $R_9$ in formula (X-VI) or (X-VIII), and exemplary range thereof may be also the same].

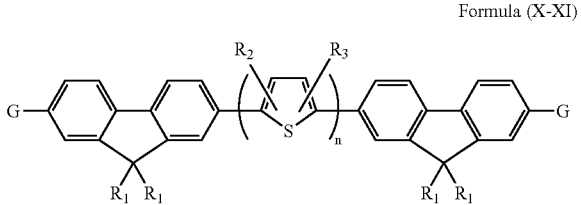

Formula (X-XI)

[In formula (X-XI), n and $R_1$ to $R_3$ have the same definitions as n and $R_1$ to $R_3$ in formula (X-1) or (X-III), respectively, and exemplary ranges thereof may be also the same; and G has the same definition as G in formula (X-VI) or (X-IX), and exemplary range thereof may be also the same].

In the coupling reaction, the halogenated compound represented by formula (X-VI) or (X-IX) may be used in an amount of preferably 0.5 to 1.5 equivalents, more preferably 0.7 to 1.2 equivalents, with respect to 1 equivalent of the acetamide compound represented by formula (X-VII) or (X-VIII). The copper catalyst for use is, for example, copper powder, cuprous oxide, copper sulfate, or the like, and may be used in an amount of preferably 0.001 to 3 parts by weight, more preferably 0.01 to 2 parts by weight, with respect to 1 part by weight of the acetamide compound represented by formula (X-VII) or (X-VIII).

The base for use is, for example, sodium hydroxide, potassium hydroxide, sodium carbonate, potassium carbonate, or the like, and may be used in an amount of preferably 0.5 to 3 equivalents, more preferably 0.7 to 2 equivalents, with respect to 1 equivalent of the acetamide compound represented by formula (X-VII) or (X-VIII).

The coupling reaction does not always demand a solvent, but examples of the solvent, when used, include high-boiling point water-insoluble hydrocarbon solvents such as n-tridecane, tetralin, p-cymene, and terpinolene; and high-boiling point halogenated solvents such as o-dichlorobenzene and chlorobenzene. The solvent may be used in an amount of preferably in the range of 0.1 to 3 parts by weight, more preferably 0.2 to 2 parts by weight, with respect to 1 part by weight of the acetamide compound represented by formula (X-VII) or (X-VIII).

The reaction is carried out, for example, under an inert gas atmosphere such as of nitrogen or argon in a temperature range of preferably 100 to 300° C., more preferably 150 to 270° C., and still more preferably 180 to 230° C., while stirred sufficiently and efficiently. The reaction may be carried out while removing water generated during the reaction. The product is cooled as needed after reaction, and the product is hydrolyzed by using a solvent such as methanol, ethanol, n-octanol, ethylene glycol, propylene glycol, or glycerol and a base such as sodium hydroxide or potassium hydroxide. In such a case, the amount of the solvent to be used is 0.5 to 10 parts by weight, preferably 1 to 5 parts by weight, with respect to 1 part by weight of the acetamide compound represented by formula (X-VII) or (X-VIII), and the amount of the base to be used is preferably 0.2 to 5 parts by weight, more preferably 0.3 to 3 parts by weight with respect to 1 part by weight of the acetamide compound represented by formula (X-VII) or (X-VIII).

The hydrolysis reaction is carried out by adding a solvent and a base directly to the reaction solution after the coupling reaction and stirring the mixture sufficiently and efficiently under an inert gas atmosphere such as of nitrogen or argon in a temperature range from 50° C. to the boiling point of the solvent. In such a case, because a carboxylate salt is generated in the coupling reaction and solidifies, use of a high-boiling point solvent having a boiling point of 150° C. or higher is preferable to raise the reaction temperature, and addition of a water-soluble solvent such as ethylene glycol, propylene glycol, or glycerol is preferable for liberating the diarylamine compound represented by formula (X-X) after injection into water and neutralization, for example with hydrochloric acid, in post-treatment. The diarylamine compound represented by formula (X-X) is liberated by pouring the reaction product into water after completion of the hydrolysis reaction and neutralizing the solution with hydrochloric acid or the like; it is then washed thoroughly and is dissolved, as needed, in a suitable solvent, and purified, for example, by i) being subjected to column chromatography with silica gel, alumina, activated clay, activated carbon, or the like, or ii) adsorbing undesirable components through addition of such an adsorbent into the solution, and recrystallizing the target compound using a suitable solvent such as acetone, ethanol, ethyl acetate, or toluene, or iii) being processed in a similar manner to the above after conversion, for example, to a methyl or ethyl ester thereof.

Then, the diamine compounds represented by formula (X-1) can be obtained by coupling the diarylamine compound represented by formula (X-X) obtained with the halogenated compound represented by formula (X-XI) in the presence of a copper catalyst and esterifying the product into its methyl ester, ethyl ester, or the like, or by esterifying the diarylamine compound represented by formula (X-X) into its methyl ester, ethyl ester, or the like, and coupling it with the dihalogenated compound represented by formula (X-XI) in the presence of a copper catalyst.

In the coupling reaction between the diarylamine compound represented by formula (X-X) and the halogenated compound represented by formula (X-XI), when a halogen disubstituted monomer is used as the compound represented by formula (X-XI), the dihalogenated compound represented by formula (X-XI) may be used in an amount of preferably 1.5 to 5 equivalents, more preferably 1.7 to 4 equivalents, with respect to 1 equivalent of the compound represented by formula (X-X).

The copper catalyst for use is, for example, copper powder, cuprous oxide, copper sulfate, or the like, and may be used in an amount of preferably 0.001 to 3 parts by weight, more preferably 0.01 to 2 parts by weight, with respect to 1 part by weight of the diarylamine compound represented by formula (X-X).

The base for use is, for example, sodium hydroxide, potassium hydroxide, sodium carbonate, potassium carbonate, or the like, and may be used in an amount of preferably 1 to 6 equivalents, more preferably 1.4 to 4 equivalents, with respect to 1 equivalent of the compound represented by formula (X-X).

Examples of the solvent to be optionally used include high-boiling point water-insoluble hydrocarbon solvents such as n-tridecane, tetralin, p-cymene, and terpinolene; high-boiling point halogenated solvents such as o-dichlorobenzene and chlorobenzene, and the solvent may be used in an amount of preferably 0.1 to 3 parts by weight, more preferably 0.2 to 2 parts by weight, with respect to 1 part by weight of the diarylamine compounds represented by formula (X-X). The reaction may be carried out under an inert gas atmosphere such as of nitrogen or argon at a temperature of preferably 100 to 300° C., more preferably 150 to 270° C., still more preferably 180 to 250° C., while stirring the mixture sufficiently and efficiently and removing water generated during reaction.

After termination of the reaction, the reaction product is dissolved in a solvent such as toluene, Isopar, or n-tridecane and, as needed, undesirable components may be removed by washing with water or filtration. Then, the product may be further purified, for example, by column chromatography with silica gel, alumina, activated clay, activated carbon, or the like, or by adding such an adsorbent into the solution to adsorb undesirable components and recrystallizing the target compound using a suitable solvent such as ethanol, ethyl acetate, or toluene.

When a halogen mono-substituted compound is used as the compound represented by formula (X-XI) for use in the coupling reaction, the halogenated compound represented by formula (X-XI), a copper catalyst, a base, and optionally, a solvent are used. Examples of the copper catalyst include copper powder, ferrous oxide, and copper sulfate, and the catalyst may be used in an amount of preferably 0.001 to 3 parts by weight, more preferably 0.01 to 2 parts by weight, with respect to 1 part by weight the diarylamine compound represented by formula (X-X).

The base for use is, for example, sodium hydroxide, potassium hydroxide, sodium carbonate, potassium carbonate, or the like, and may be used in an amount of 0.5 to 3 equivalents, preferably 0.7 to 2 equivalents, with respect to 1 equivalent of the diarylamine compound represented by formula (X-X). The solvent is, for example, a high-boiling point water-insoluble hydrocarbon solvent such as n-tridecane, tetralin, p-cymene, or terpinolene, or a high-boiling point halogenated solvent such as o-dichlorobenzene or chlorobenzene, and may be used in an amount of preferably 0.1 to 3 parts by weight, more preferably 0.2 to 2 parts by weight with respect to 1 part by weight of the diarylamine compounds represented by formula (X-X).

The reaction product is then processed and purified similarly to the case where the compound represented by formula (X-XI) is a dihalogenated compound.

The thiophene-containing compound according to as aspect of the invention can also be prepared by preparing a triarylamine compound represented by the following formula (X-XII) containing a thiophene ring in a coupling reaction in the presence of a copper catalyst similarly to the reaction above, and converting the compound into the halogenated compound (X-XIII) by halogenation of the thiophene ring with N-bromosuccimide (NBS), N-chlorosuccimide (NCS), or the like, and then subjecting the halogenated compound (X-XIII) to a homo-coupling reaction in the presence of a nickel catalyst.

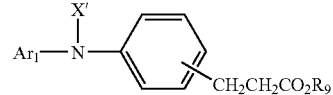

Formula (X-XII)

[In formula (X-XII), $Ar_1$ has the same definition as $Ar_1$ in formula (X-1) or (X-III), and exemplary range thereof may be also the same; and X' represents a substituted or unsubstituted bivalent aromatic group containing one or plural thiophene rings; and $R_9$ represents a hydrogen atom, an alkyl group, a substituted or unsubstituted aryl group, or a substituted or unsubstituted aralkyl group].

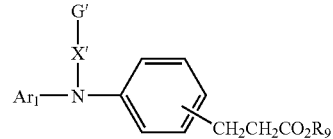

Formula (X-XIII)

[In formula (X-XIII), $Ar_1$, X', and $R_9$ have the same definitions as $Ar_1$, X', and $R_9$ in formula (X-XII), and exemplary ranges thereof may be also the same; and G' represents a bromine or chlorine atom].

The homo-coupling reaction is carried out in combination of a halogenated compound represented by formula (X-XIII), a nickel complex, triphenylphosphine, and zinc in a solvent. When the halogen atom to be introduced is a chlorine atom, the halogen atom may be introduced by halogenation before the triarylamine skeleton is formed in coupling reaction using a copper catalyst.

Examples of the nickel complex for use in an aspect of the invention include nickel chloride, nickel bromide, and nickel acetate, and the nickel complex may be used in an amount of preferably 0.001 to 3 equivalents, more preferably 0.1 to 2 equivalents, with respect to 1 equivalent of the compound (X-XIII). In addition, a reducing agent such as zinc may be present in the reaction system, and may be used in an amount of preferably 0.001 to 3 equivalents, more preferably 0.1 to 2 equivalents, with respect to 1 equivalent of the compound represented by formula (X-XIII). Triphenylphosphine may be used in an amount of 0.5 to 3 equivalents, preferably 0.7 to 2 equivalents, with respect to 1 equivalent of the compound (X-XIII).

Examples of the solvent for use in the reaction include dimethylformamide (DMF), dimethylacetamide (DMA), tetrahydrofuran (THF), dimethoxyethane (DME), and N-methylpyrrolidone (NMP), and the solvent may be used in an amount of preferably 0.1 to 10 equivalents, more preferably 2 to 5 equivalents, with respect to 1 equivalent of the compounds above. The reaction may be carried out under an inert gas atmosphere such as of nitrogen or argon at a temperature of 0 to 100° C., preferably in a temperature range from room temperature to 50° C., while the solution is stirred sufficiently and efficiently.

After termination of the reaction, the reaction solution is poured into water and the mixture is stirred thoroughly, and, when the reaction product is crystalline, a crude product is collected by suction filtration. When the reaction product is oily, a crude product can be obtained by extraction with a suitable solvent such as ethyl acetate or toluene. The crude product thus obtained is purified by being subjected to column chromatography with silica gel, alumina, activated clay, activated carbon, or the like, or by adding such an adsorbent into the solution and adsorbing undesirable components. When the reaction product is crystalline, it is further purified by recrystallization using a suitable solvent such as hexane, methanol, acetone, ethanol, ethyl acetate, or toluene.

The polymer according to an aspect of the invention represented by formulae (X-II-1) and (X-II-2) can be prepared from a monomer represented by the following formula (X-XIV) by polymerization according to a known method described, for example, in New Experimental Chemistry 4th Ed., 28 (the Chemical Society of Japan Ed., Maruzen).

<1> When A' is Hydroxyl Group

When A' is a hydroxyl group, a dihydric alcohol represented by HO—(Y—O)$_m$—H is mixed substantially in the equivalent amount, and polymerization is allowed to proceed in the presence of an acid catalyst. An acid commonly used for esterification such as sulfuric acid, toluenesulfonic acid, or trifluoroacetic acid can be used as the acid catalyst, and it may be used in an amount in the range of preferably 1/10,000 to 1/10 part by weight, more preferably 1/1,000 to 1/50 part by weight, with respect to 1 part by weight of the monomer. Use of a solvent that is azeotropic with water may be used to remove water generated during preparation, and use of toluene, chlorobenzene, 1-chloronaphthalene, or the like, is effective. The solvent that is azeotropc with water may be used in an amount in the range of preferably 1 to 100 parts by weight, more preferably 2 to 50 parts by weight, with respect to 1 part by weight of the monomer. Y and m have the same definitions as Y and m described above, respectively, and exemplary ranges thereof may be also the same.

The reaction temperature is arbitrarily set, and the reaction may be carried out at the boiling point of the solvent so as to remove water generated during polymerization. When no solvent is used, the resultant polymer is dissolved in a solvent that is capable of dissolving the polymer after reaction. When a solvent is used, the polymer is precipitated by adding dropwise the reaction solution as it is into a poor solvent such as an alcohol (e.g., methanol or ethanol) or acetone. Then, the polymer is separated, washed thoroughly with water and/or an organic solvent, and dried. Further, if needed, the polymer may be reprecipitated repeatedly by dissolving the polymer in a suitable organic solvent and then adding the solution into a poor solvent dropwise to precipitate the polymer. During the reprecipitation processing, it is preferable to stir the solution sufficiently and efficiently with a mechanical stirrer or the like. The amount of the solvent to be used for dissolving the polymer during the reprecipitation is in the range of preferably 1 to 100 parts by weight, more preferably 2 to 50 parts, with respect to 1 part by weight of the polymer. The amount of the poor solvent to be used is in the range of preferably 1 to 1,000 parts by weight, more preferably 10 to 500 parts by weight, with respect to 1 part by weight of the polymer.

Formula (X-XIV)

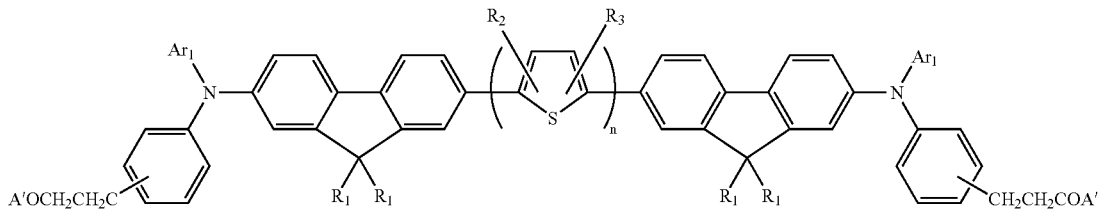

In formula (X-XIV), n, $Ar_1$, and $R_1$ to $R_3$ have the same definitions as n, $Ar_1$, and $R_1$ to $R_3$ in formula (X-1) above, respectively, and exemplary ranges thereof may be also the same. A' represents a hydroxyl group, a halogen atom, or —O—$R_{10}$ ($R_{10}$ represents an alkyl group, a substituted or unsubstituted aryl group or an aralkyl group. Specifically, the thiophene-containing compound polymers represented by formulae (X-II-1) and (X-II-2) can be prepared in the following manner:

[2] When A' is Halogen

When A' is a halogen, a dihydric alcohol represented by HO—(Y—O)$_m$—H is mixed substantially in the equivalent amount, and polymerization is allowed to proceed in the presence of an organic base catalyst such as pyridine or triethylamine. The organic base catalyst may be used in an amount in the range of 1 to 10 parts by weight, preferably 2 to 5 parts by weight, with respect to 1 part by weight of the monomer. Effective solvents include methylene chloride, tetrahydrofuran (THF), toluene, chlorobenzene, 1-chloronaphthalene, and the like, and the solvent may be used in an amount in the range of 1 to 100 parts by weight, preferably 2 to 50 parts by weight, with respect to 1 part by weight of the monomer. The reaction temperature may be arbitrarily set. The polymer after polymerization may be purified by reprecipitation as described above. Y and m have the same definitions as Y and m described above, respectively, and exemplary ranges thereof may be also the same.

An interfacial polymerization method may be used when a dihydric alcohol having higher acidity such as bisphenol is used. Specifically, after water is added to a dihydric alcohol and an equivalent amount of a base is added to and dissolved in the mixture, a monomer solution containing the monomer in the equivalent amount to the dihydric alcohol is then added thereto while the mixture is stirred vigorously, whereby the polymerization occurs. The amount of water used then is in the range of 1 to 1,000 parts by weight, preferably 2 to 500 parts by weight, with respect to 1 part by weight of the dihydric alcohol. Examples of solvents effective in dissolving the monomer include methylene chloride, dichloroethane, trichloroethane, toluene, chlorobenzene, and 1-chloronaphthalene. The reaction temperature may be set arbitrarily, and use of a phase-transfer catalyst such as an ammonium salt or a sulfonium salt is effective for acceleration of the reaction. The phase-transfer catalyst may be used in an amount in the range of 0.1 to 10 parts by weight, preferably 0.2 to 5 parts by weight, with respect to 1 part by weight of the monomer.

[3] When A' is —O—$R_{10}$

When A' is —O—$R_{10}$, a polymer can be obtained in ester exchange reaction in which an excessive amount of dihydric alcohol represented by HO—(Y—O)$_m$—H is added, and the reaction mixture is heated in the presence of a catalyst such as an inorganic acid (e.g., sulfuric acid or phosphoric acid), titanium alkoxide, an acetate or carbonate salt of calcium and cobalt, or an oxide of zinc. The dihydric alcohol is used in an amount in the range of 2 to 100 equivalents, preferably 3 to 50 equivalents, with respect to 1 equivalent of the monomer. The catalyst may be used in an amount in the range of $\frac{1}{1,000}$ to 1 parts by weight, preferably $\frac{1}{100}$ to $\frac{1}{2}$ parts by weight, with respect to 1 part by weight of the monomer. The reaction may be carried out at a reaction temperature of 200 to 300° C., and, after completion of ester exchange from the group —O—$R_{10}$ to the group HO—(Y—O)$_m$—H, the reaction may be carried out under reduced pressure so as to accelerate the polymerization reaction through elimination of the group HO—(Y—O)$_m$—H. Y and m have the same definitions as Y and m described above, respectively, and exemplary ranges thereof may be also the same.

In an exemplary embodiment, the reaction is carried out under a reduced pressure by using a high-boiling solvent azeotropic with the group HO—(Y—O)$_m$—H, such as 1-chloronaphthalene, while the group HO—(Y—O)$_m$—H is removed by azeotropic distillation.

On the other hand, the thiophene-containing compound polymer represented by formula (X-II-2) can be prepared in the following manner: In each of the cases described above, the compound represented by the following formula (X-XV) is formed by allowing the reaction to proceed in the presence of an excess dihydric alcohol, and the desired polymer can be obtained by allowing the compound represented by formula (X-XV) as the monomer to react with a bivalent carboxylic acid, a bivalent carboxylic halide, or the like.

Formula (X-XV)

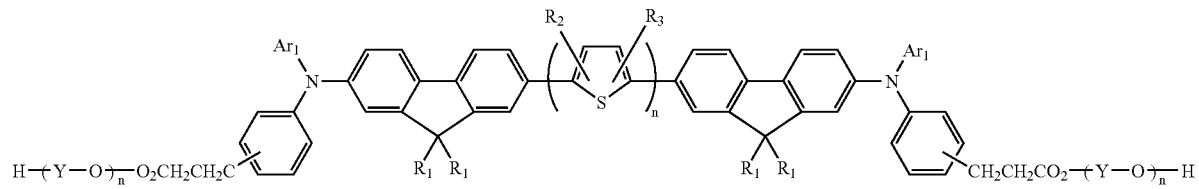

In formula (X-XV), $Ar_1$, X, $R_1$ to $R_3$, and n have the same definitions as $Ar_1$, X, $R_1$ to $R_3$, and n in formula (X-1) above, respectively, and exemplary ranges thereof may be also the same. Y represents a hydrocarbon group.

The thiophene-containing compound and the thiophene-containing compound polymer according to an aspect of the invention are compounds superior in electric charge-transporting efficiency, solubility, and film-formability, and also higher in charge-transporting efficiency and light-emitting efficiency. In addition, the thiophene-containing compound according to an aspect of the invention and the polymer thereof are easy to prepare and to control the physical properties thereof such as ionization potential (IP) and glass transition temperature (Tg) by introduction of substituents, and thus, are very useful as a material for use in organic electronic devices such as organic photoreceptors, organic electroluminescent devices, and organic transistors.

The organic electroluminescent device according to one aspect of the present invention is an electroluminescent device including a pair of electrodes, at least one of which being a transparent or semitransparent electrode, and one or more organic compound layers provided between the electrodes. At least one of the organic compound layers includes a charge-transporting polyester having a repeating structure containing at least one structure selected from the structures represented by the following formulae (I-1) and (I-2) as its partial structure.

Formula (I-1)

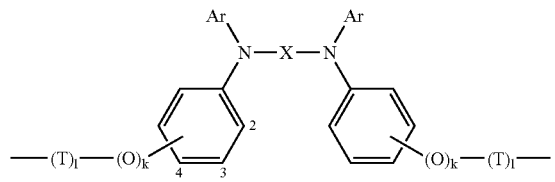

Formula (I-2)

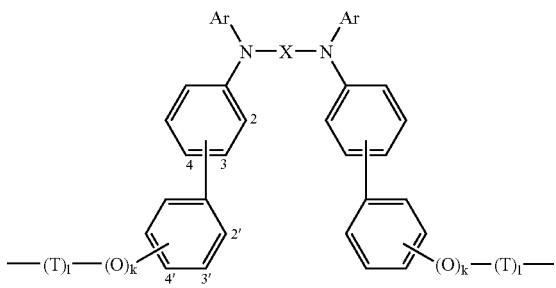

[In formulae (I-1) and (I-2), Ar represents a substituted or unsubstituted monovalent phenyl group, a substituted or unsubstituted monovalent polynuclear aromatic hydrocarbon having 2 to 10 aromatic rings, a substituted or unsubstituted a monovalent fused aromatic hydrocarbon having 2 to 10 aromatic rings, or a substituted or unsubstituted monovalent aromatic heterocyclic ring; X represents a group represented by the following formula (II); T represents a bivalent straight-chain hydrocarbon group having 1 to 6 carbon atoms or a bivalent branched hydrocarbon group having 2 to 10 carbon atoms; and k and l each independently represent an integer of 0 or 1]:

Formula (II)

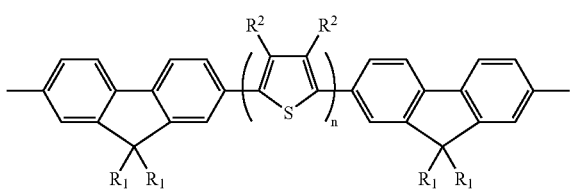

[In formula (II), $R^1$ and $R^2$ each independently represent a hydrogen atom, a substituted or unsubstituted alkyl group, a substituted or unsubstituted aryl group, or a substituted or unsubstituted aralkyl group; and n is an integer of 1 to 10].

The organic electroluminescent device according to the aspect of the invention having at least one organic compound layer containing a charge-transporting polyester shows sufficient luminance and is superior in stability and durability. It also allows expansion in size and is easy to produce. It is also possible to provide the charge-transporting polyester with hole-transporting ability and/or electron-transporting ability by selecting the structure described below appropriately, and thus, the charge-transporting polyester can be used in any of the layers such as a hole transport layer, a light-emitting layer, or an electron transport layer in accordance with the purpose.

Hereinafter, as the beginning of detailed description of aspects of the invention, the charge-transporting polyester according to the aspect of the invention will be described first in detail.

—Charge-Transporting Polyester—

In formulae (I-1) and (I-2), Ar represents a substituted or unsubstituted monovalent phenyl group, a substituted or unsubstituted monovalent polynuclear aromatic hydrocarbon having 2 to 10 aromatic rings, a substituted or unsubstituted monovalent fused aromatic hydrocarbon having 2 to 10 aromatic rings, or a substituted or unsubstituted monovalent aromatic heterocyclic ring. The two Ar groups present in each of formula (I-1) and (I-2) may be the same as or different from each other, but are preferably the same from the viewpoint of productivity.

In formulae (I-1) and (I-2), the number of aromatic rings constituting the polynuclear aromatic hydrocarbon or the fused aromatic hydrocarbon selected as the structure represented by Ar is more preferably 2 to 5, and the fused aromatic hydrocarbon is preferably an aromatic hydrocarbon in which all aromatic rings are fused.

In formulae (I-1) and (I-2), the aromatic heterocyclic ring selected as the structure represented by Ar is an aromatic ring containing elements other than carbon and hydrogen. The number of the atoms constituting the ring skeleton (Nr) may be, for example, 5 or 6. The kind and number of the atoms other than carbon (hetero atoms) in the ring skeleton are not particularly limited, but, for example, a sulfur atom, a nitrogen atom, an oxygen atom, or the like may be used. Two or more kinds of hetero atoms may be contained in the ring skeleton. Two or more hetero atoms may be contained in the ring skeleton. Examples of the heterocyclic ring having a five-membered ring structure include thiophene, thiofin, pyrrole, furan, and a heterocyclic ring obtained by substituting the carbons at the 3- and 4-positions of any of the above heterocyclic rings with nitrogens, and examples of the heterocyclic rings having a six-membered ring structure include a pyridine ring.

Although the ring may be entirely or partially conjugated, it is preferably an entirely conjugated system from the points of charge-transporting efficiency and luminous efficiency.

Examples of a substituent on a group represented by Ar in formulae (I-1) and (I-2) include a hydrogen atom, alkyl groups, alkoxy groups, phenoxy groups, aryl groups, aralkyl groups, substituted amino groups, and halogen atoms. The alkyl group may be a group having 1 to 10 carbon atoms, and examples thereof include a methyl group, an ethyl group, a propyl group, and an isopropyl group. The alkoxy group may be a group having 1 to 10 carbon atoms, and examples thereof include a methoxy group, an ethoxy group, a propoxy group, and an isopropoxy group. The aryl group may be a group having 6 to 20 carbon atoms, and examples thereof include a phenyl group and a toluyl group. The aralkyl group may be a group having 7 to 20 carbon atoms, and examples thereof include a benzyl group and a phenethyl group. Examples of a substituent contained in the substituted amino group include alkyl groups, aryl groups, and aralkyl groups, and specific examples thereof are the same as those described above.

In formulae (I-1) and (I-2), X represents a bivalent aromatic group represented by formula (II) above.

In formula (II), the alkyl group selected as the structure represented by $R^1$ or $R^2$ may be a group having 1 to 10 carbon atoms, and examples thereof include a methyl group, an ethyl group, a propyl group, and an isopropyl group. The aryl group may be a group having 6 to 20 carbon atoms, and examples thereof include a phenyl group and a toluyl group. The aralkyl group may be a group having 7 to 20 carbon atoms, and examples thereof include a benzyl group and a phenethyl group.

In formula (II), when there is a substituent on the group represented by $R^1$ or $R^2$, the substituent may be selected from those described above as substituents that can be substituted on a group represented by Ar in formulae (I-1) and (I-2).

Multiple groups $R^1$s or $R^2$s present in formula (II) may be the same as or different from each other.

In formulae (I-1) and (I-2), T represents a bivalent straight-chain hydrocarbon group having 1 to 6 carbon atoms or a bivalent branched hydrocarbon group having 2 to 10 carbon atoms, and is preferably selected from bivalent straight-chain hydrocarbon groups having 2 to 6 carbon atoms and bivalent branched hydrocarbon groups having 3 to 7 carbon atoms. More specifically among them, the bivalent hydrocarbon groups shown below are more preferable.

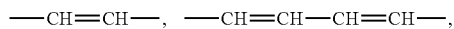

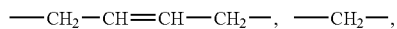

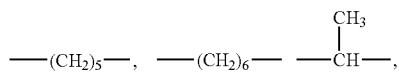

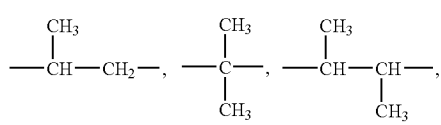

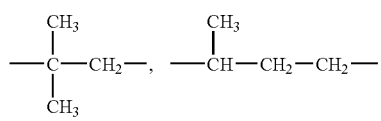

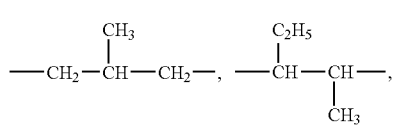

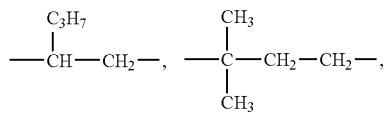

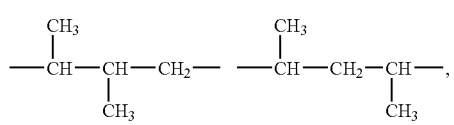

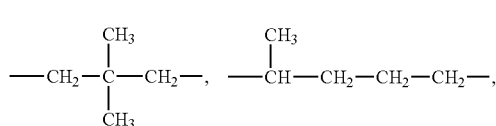

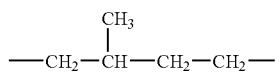

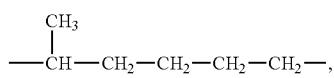

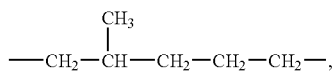

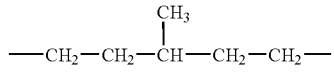

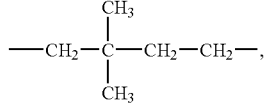

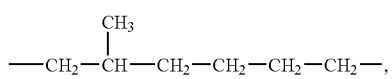

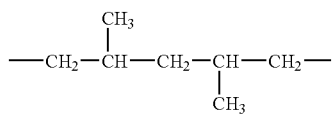

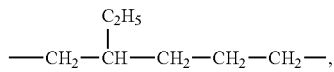

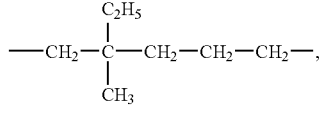

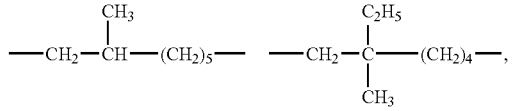

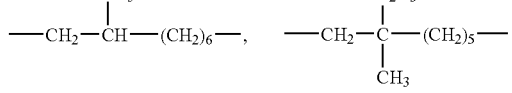

In each of formulae (I-1) and (I-2), the numbers, ls, for the two -(T)$_l$- groups flanking the aromatic diamine skeleton may be the same as or different from each other, and two or more groups Ts flanking the aromatic diamine skeleton may be the same as or different from each other. However, a structure in which the numbers ls are the same and the kinds of Ts are the same is preferable from the viewpoint of productivity.

Specific examples of the structure represented by formula (I-1) above are shown below. In the Tables, "Bond Pos." refers to the bond position.

TABLE 7

| Structure | X | Ar | T | k | l | Bond Pos. |
|---|---|---|---|---|---|---|
| 1 | (fluorene-thiophene-fluorene structure) | (phenyl) | — | 1 | 0 | 3 |
| 2 | (fluorene-bithiophene-fluorene structure) | (2,4-dimethylphenyl) | — | 1 | 0 | 3 |
| 3 | (fluorene-dimethylbithiophene-fluorene structure) | (biphenyl) | — | 1 | 0 | 4 |

TABLE 7-continued

| Structure | X | Ar | T | k | l | Bond Pos. |
|---|---|---|---|---|---|---|
| 4 | (structure) | (fluorene structure) | — | 1 | 0 | 4 |
| 5 | (structure) | (structure) | — | 1 | 0 | 4 |
| 6 | (structure) | (naphthalene structure) | —CH$_2$— | 1 | 1 | 3 |

TABLE 8

| Structure | X | Ar | T | k | l | Bond Pos. |
|---|---|---|---|---|---|---|
| 7 | | | —CH₂CH₂— | 1 | 1 | 3 |
| 8 | | | —CH₂CH₂— | 1 | 1 | 3 |
| 9 | | | —CH₂— | 1 | 1 | 4 |

TABLE 8-continued

| Structure | X | Ar | T | k | l | Bond Pos. |
|---|---|---|---|---|---|---|
| 10 | (bis-fluorene-bithiophene structure) | 2,4-dimethylphenyl | —CH₂CH₂— | 1 | 1 | 4 |
| 11 | (bis-fluorene-bithiophene with two dimethylphenyl substituents) | terphenyl (4-methyl) | C(CH₃)₂ with CH₂ linkers (neopentyl-type) | 1 | 1 | 4 |
| 12 | (bis-fluorene-thiophene structure) | 2,5-dimethylphenyl | —CH₂— | 0 | 1 | 3 |

TABLE 9

| Structure | X | Ar | T | k | l | Bond Pos. |
|---|---|---|---|---|---|---|
| 13 | (bis-fluorenyl-thiophene) | 4-methoxyphenyl | —CH₂CH₂— | 0 | 1 | 3 |
| 14 | (bis-fluorenyl-thiophene) | 9,9-dimethyl-2-methylfluorenyl | —CH₂CH₂— | 0 | 1 | 3 |
| 15 | (bis-fluorenyl-thiophene) | 9,9-dioctyl-7-(thiophen-2-yl)fluorenyl | —CH₂— | 0 | 1 | 4 |

TABLE 9-continued

| Structure | X | Ar | T | k | l | Bond Pos. |
|---|---|---|---|---|---|---|
| 16 | (9,9-dimethylfluorene-thiophene-9,9-dimethylfluorene) | 5-(4-methylstyryl)-4-n-hexylthiophen-2-yl | —CH$_2$— | 0 | 1 | 4 |
| 17 | (9,9-dimethylfluorene-thiophene-9,9-dimethylfluorene) | 3,5-bis(2,4-dimethylphenyl)-2-(4-methylstyryl)thiophene | C(CH$_3$)$_2$CH$_2$C(CH$_3$)$_2$CH$_2$ | 0 | 1 | 4 |
| 18 | (9,9-dimethylfluorene-thiophene-9,9-dimethylfluorene) | 4-phenoxy-4′-methylbiphenyl ether | C(CH$_3$)$_2$CH$_2$C(CH$_3$)$_2$CH$_2$ | 0 | 1 | 4 |

TABLE 10

| Structure | X | Ar | T | k | l | Bond Pos. |
|---|---|---|---|---|---|---|
| 19 | (fluorene-thiophene-fluorene structure) | 4-methyl-p-terphenyl | —CH$_2$— | 0 | 1 | 4 |
| 20 | (fluorene-thiophene-fluorene structure) | 1-methylnaphthalene | —CH$_2$CH$_2$— | 0 | 1 | 4 |
| 21 | (fluorene-thiophene-fluorene structure) | methylphenanthrene | —CH$_2$CH$_2$— | 0 | 1 | 4 |

TABLE 10-continued

| Structure | X | Ar | T | k | l | Bond Pos. |
|---|---|---|---|---|---|---|
| 22 | | | —CH$_2$CH$_2$— | 0 | 1 | 4 |
| 23 | | | —CH$_2$CH$_2$— | 0 | 1 | 4 |
| 24 | | | —CH$_2$CH$_2$— | 0 | 1 | 4 |

TABLE 11

| Structure | X | Ar | T | k | l | Bond Pos. |
|---|---|---|---|---|---|---|
| 25 | | | —CH$_2$CH$_2$— | 0 | 1 | 4 |
| 26 | | | —CH$_2$— | 0 | 1 | 4 |
| 27 | | | —CH$_2$CH$_2$— | 0 | 1 | 4 |
| 28 | | | —CH$_2$— | 0 | 1 | 4 |
| 29 | | | —CH$_2$CH$_2$— | 0 | 1 | 4 |
| 30 | | | —CH$_2$CH$_2$— | 0 | 1 | 4 |

TABLE 12

| Structure | X | Ar | T | k | l | Bond Pos. |
|---|---|---|---|---|---|---|
| 31 | (fluorene-thiophene-thiophene-fluorene) | biphenyl | —CH₂CH₂— | 0 | 1 | 4 |
| 32 | (fluorene-thiophene-thiophene-fluorene) | terphenyl | —CH₂CH₂— | 0 | 1 | 4 |
| 33 | (fluorene-thiophene-thiophene-fluorene) | methylnaphthyl | —CH₂CH₂— | 0 | 1 | 4 |
| 34 | (fluorene-thiophene-thiophene-fluorene) | 9,9-dimethylfluorenyl | —CH₂— | 0 | 1 | 4 |
| 35 | (fluorene-thiophene-thiophene-fluorene) | 5-chlorothienyl-9,9-dimethylfluorenyl | C(CH₃)₂(CH₂)... | 0 | 1 | 4 |
| 36 | (fluorene-thiophene-thiophene-fluorene) | n-hexyl-bithienyl-phenyl | C(CH₃)₂(CH₂)... | 0 | 1 | 4 |

TABLE 13

| Structure | X | Ar | T | k | l | Bond Pos. |
|---|---|---|---|---|---|---|
| 37 | | | —CH₂CH₂— | 0 | 1 | 4 |
| 38 | | | (neopentyl-type linker) | 0 | 1 | 3 |
| 39 | | | (neopentyl-type linker) | 0 | 1 | 4 |
| 40 | | | —CH₂CH₂— | 0 | 1 | 4 |
| 41 | | | —CH₂CH₂— | 0 | 1 | 4 |
| 42 | | | —CH₂CH₂— | 0 | 1 | 4 |

TABLE 14

| Structure | X | Ar | T | k | l | Bond Pos. |
|---|---|---|---|---|---|---|
| 43 | (fluorene-thiophene-thiophene-fluorene structure) | (methylthiophene-naphthalene) | —CH₂CH₂— | 0 | 1 | 4 |
| 44 | (fluorene-thiophene-thiophene-fluorene structure) | (methylthiophene-thiophene-naphthalene) | —CH₂CH₂— | 0 | 1 | 4 |
| 45 | (fluorene-methylthiophene-methylthiophene-fluorene structure) | (phenyl) | —CH₂— | 0 | 1 | 4 |

TABLE 14-continued

| Structure | X | Ar | T | k | l | Bond Pos. |
|---|---|---|---|---|---|---|
| 46 | (fluorene-thiophene-thiophene-fluorene structure with CH₃ groups) | 2,4-dimethylphenyl | —CH₂CH₂— | 0 | 1 | 4 |
| 47 | (fluorene-thiophene-thiophene-fluorene structure with CH₃ groups) | biphenyl (4-methyl) | —CH₂— | 0 | 1 | 4 |
| 48 | (fluorene-thiophene-thiophene-fluorene structure with CH₃ groups) | naphthyl | —CH₂— | 0 | 1 | 3 |

TABLE 15

| Structure | X | Ar | T | k | l | Bond Pos. |
|---|---|---|---|---|---|---|
| 49 | [bis-fluorenyl-bithiophene structure] | anthracene | —CH$_2$CH$_2$— | 0 | 1 | 4 |
| 50 | [bis-fluorenyl-bithiophene structure] | 9,9-dimethyl-2-methylfluorene | —CH$_2$CH$_2$— | 0 | 1 | 4 |
| 51 | [bis-fluorenyl-bithiophene structure] | 9,9-di-n-propyl-2-methylfluorene | —C(CH$_3$)$_2$CH$_2$— | 0 | 1 | 4 |
| 52 | [bis-fluorenyl-bithiophene structure] | 2-(thienylvinyl)-9,9-dimethyl-7-methylfluorene | —CH$_2$CH$_2$— | 0 | 1 | 4 |
| 53 | [bis-fluorenyl-bithiophene structure] | 5-n-hexyl-2-(4-methylphenyl)thiophene | —CH$_2$— | 0 | 1 | 4 |

TABLE 16

| Structure | X | Ar | T | k | l | Bond Pos. |
|---|---|---|---|---|---|---|
| 54 | | | —CH$_2$CH$_2$— | 0 | 1 | 3 |
| 55 | | | —CH$_2$CH$_2$— | 0 | 1 | 4 |
| 56 | | | —CH$_2$CH$_2$— | 0 | 1 | 2 |

TABLE 16-continued

| Structure | X | Ar | T | k | l | Bond Pos. |
|---|---|---|---|---|---|---|
| 57 | (fluorene-thiophene-thiophene-fluorene structure with CH3 groups) | 2-(p-tolyl)quinoline | —CH$_2$— | 0 | 1 | 3 |
| 58 | (fluorene-thiophene-thiophene-fluorene structure with CH3 groups) | N,N-diphenyl-4-methylaniline (triarylamine) | —CH$_2$CH$_2$— | 0 | 1 | 4 |

TABLE 17

| Structure | X | Ar | T | k | l | Bond Pos. |
|---|---|---|---|---|---|---|
| 59 | | | —CH$_2$CH$_2$— | 0 | 1 | 4 |
| 60 | | | —CH$_2$CH$_2$— | 0 | 1 | 3 |
| 61 | | | —CH$_2$— | 0 | 1 | 4 |

TABLE 17-continued

| Structure | X | Ar | T | k | l | Bond Pos. |
|---|---|---|---|---|---|---|
| 62 | (structure) | (biphenyl with methyl) | —CH$_2$— | 0 | 1 | 4 |
| 63 | (structure) | (biphenyl with OCH$_3$ and CH$_3$) | —CH$_2$CH$_2$— | 0 | 1 | 4 |

TABLE 18

| Structure | X | Ar | T | k | l | Bond Pos. |
|---|---|---|---|---|---|---|
| 64 | | 1-methylnaphthalene | —CH₂CH₂— | 0 | 1 | 4 |
| 65 | | 9-methylanthracene | —CH₂— | 0 | 1 | 4 |
| 66 | | 9-methylphenanthrene | —CH₂— | 0 | 1 | 4 |

TABLE 18-continued

| Structure | X | Ar | T | k | l | Bond Pos. |
|---|---|---|---|---|---|---|
| 67 | (fluorene-thiophene-thiophene-fluorene structure with phenyl and methyl substituents) | (methylpyrene) | —CH₂CH₂— | 0 | 1 | 4 |
| 68 | (fluorene-thiophene-thiophene-fluorene structure with phenyl and methyl substituents) | (methylfluorene) | neopentyl-type C(CH₃)(CH₃)(CH₂—)(CH₂—) | 0 | 1 | 4 |

TABLE 19

| Structure | X | Ar | T | k | l | Bond Pos. |
|---|---|---|---|---|---|---|
| 69 | | | —CH$_2$— | 0 | 1 | 4 |
| 70 | | | —CH$_2$CH$_2$— | 0 | 1 | 3 |
| 71 | | | —CH$_2$CH$_2$— | 0 | 1 | 4 |

TABLE 19-continued
| Structure | X | Ar | T | k | l | Bond Pos. |
|---|---|---|---|---|---|---|
| 72 | 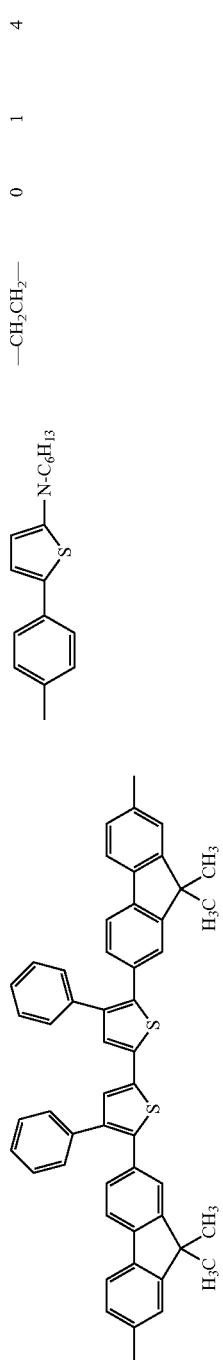 | 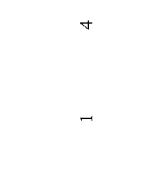 | —CH₂CH₂— | 0 | 1 | 4 |
| 73 | 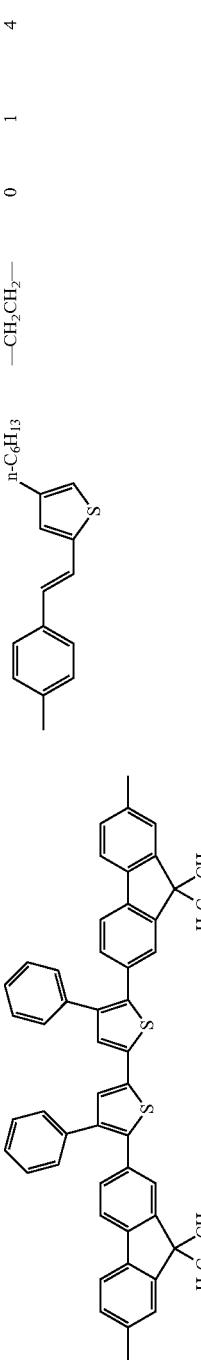 |  | —CH₂CH₂— | 0 | 1 | 4 |

TABLE 20

| Structure | X | Ar | T | k | l | Bond Pos. |
|---|---|---|---|---|---|---|
| 74 | (fluorene-thiophene(Ph)-thiophene(Ph)-fluorene) | α-CN-4-methylstyryl-thiophene | —CH₂CH₂— | 0 | 1 | 3 |
| 75 | (fluorene-thiophene(Ph)-thiophene(Ph)-fluorene) | 4-methylstilbene | —CH₂CH₂— | 0 | 1 | 4 |
| 76 | (fluorene-thiophene(Ph)-thiophene(Ph)-fluorene) | 4-methylstyryl-bithiophene | —C(CH₃)(CH₂CH₃)— neopentyl-like linker | 0 | 1 | 4 |

TABLE 20-continued

| Structure | X | Ar | T | k | l | Bond Pos. |
|---|---|---|---|---|---|---|
| 77 | (structure) | (4-methylphenyl-C≡C-phenyl) | —CH₂CH₂— | 0 | 1 | 4 |
| 78 | (structure) | (2,5-diaryl-1,3,4-oxadiazole) | —CH₂CH₂— | 0 | 1 | 4 |

TABLE 21
| Structure | X | Ar | T | k | l | Bond Pos. |
|---|---|---|---|---|---|---|
| 79 | 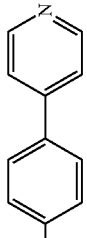 | 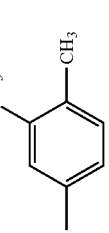 | —CH$_2$CH$_2$— | 0 | 1 | 3 |
| 80 |  | 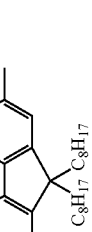 | —CH$_2$— | 0 | 1 | 4 |
| 81 | 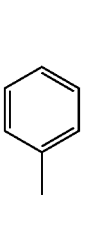 | 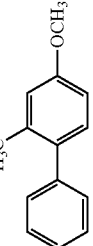 | —CH$_2$CH$_2$— | 0 | 1 | 4 |
| 82 | 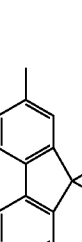 | 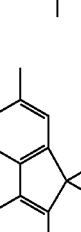 | —CH$_2$— | 0 | 1 | 4 |
| 83 | 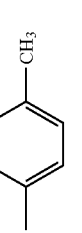 | 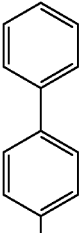 | —CH$_2$CH$_2$— | 0 | 1 | 4 |
| 84 | 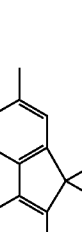 | 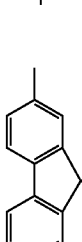 | —CH$_2$CH$_2$— | 0 | 1 | 4 |

TABLE 22

| Structure | X | Ar | T | k | l | Bond Pos. |
|---|---|---|---|---|---|---|
| 85 | (bis-fluorenyl-bithiophene) | 1-methylnaphthyl | —CH₂CH₂— | 0 | 1 | 4 |
| 86 | (bis-fluorenyl-bithiophene) | methylphenanthryl | —CH₂CH₂— | 0 | 1 | 4 |
| 87 | (bis-fluorenyl-bithiophene) | 9,9-dimethylfluorenyl | —CH₂CH₂— | 0 | 1 | 4 |
| 88 | (bis-fluorenyl-bithiophene) | 9,9-di-n-propylfluorenyl | —CH₂— | 0 | 1 | 4 |

TABLE 22-continued

| Structure | X | Ar | T | k | l | Bond Pos. |
|---|---|---|---|---|---|---|
| 89 | | | —CH₂CH₂— | 0 | 1 | 4 |
| 90 | | | —CH₂CH₂— | 0 | 1 | 3 |
| 91 | | | —CH₂— | 0 | 1 | 4 |

TABLE 23

| Structure | X | Ar | T | k | l | Bond Pos. |
|---|---|---|---|---|---|---|
| 92 | (fluorene-thiophene-thiophene-fluorene structure with C8H17 groups and methyl substituents) | (2,4-dimethylphenyl-thiophene with Cl and p-tolyl substituents) | —CH$_2$CH$_2$— | 0 | 1 | 4 |
| 93 | (fluorene-thiophene-thiophene-fluorene structure with C8H17 groups and methyl substituents) | (4-methylstilbene) | —CH$_2$CH$_2$— | 0 | 1 | 4 |
| 94 | (fluorene-thiophene-thiophene-fluorene structure with C8H17 groups and methyl substituents) | (3-pyridyl-4-methylphenyl) | —CH$_2$CH$_2$— | 0 | 1 | 4 |

TABLE 23-continued

| Structure | X | Ar | T | k | l | Bond Pos. |
|---|---|---|---|---|---|---|
| 95 | (fluorene-Bu-thiophene-thiophene-Bu-fluorene) | phenyl | —CH$_2$CH$_2$— | 0 | 1 | 4 |
| 96 | (fluorene-Bu-thiophene-thiophene-Bu-fluorene) | 4-methylphenyl | —CH$_2$CH$_2$— | 0 | 1 | 4 |
| 97 | (fluorene-Bu-thiophene-thiophene-Bu-fluorene) | 2,4-dimethylphenyl | —CH$_2$CH$_2$— | 0 | 1 | 4 |

TABLE 24

| Structure | X | Ar | T | k | l | Bond Pos. |
|---|---|---|---|---|---|---|
| 98 | (fluorene-Bu-thiophene-thiophene-Bu-fluorene structure) | 4-methylbiphenyl | —CH$_2$— | 0 | 1 | 3 |
| 99 | (fluorene-Bu-thiophene-thiophene-Bu-fluorene structure) | 4-methyl-p-terphenyl | —CH$_2$CH$_2$— | 0 | 1 | 4 |
| 100 | (fluorene-Bu-thiophene-thiophene-Bu-fluorene structure) | methylnaphthalene | —CH$_2$CH$_2$— | 0 | 1 | 4 |

TABLE 24-continued

| Structure | X | Ar | T | k | l | Bond Pos. |
|---|---|---|---|---|---|---|
| 101 | | | —CH₂CH₂— | 0 | 1 | 4 |
| 102 | | | —CH₂CH₂— | 0 | 1 | 4 |
| 103 | | | —CH₂CH₂— | 0 | 1 | 4 |

TABLE 25

| Structure | X | Ar |
|---|---|---|
| 104 | Fluorene(CH₃)₂–Thiophene(Bu)–Thiophene(Bu)–Fluorene(CH₃)₂ | –C₆H₄–Thiophene–n-C₆H₁₃ |
| 105 | Fluorene(CH₃)₂–Thiophene(Bu)–Thiophene(Bu)–Fluorene(CH₃)₂ | –C₆H₄–C(CN)=C(CN)–Thiophene |
| 106 | Fluorene(CH₃)₂–Thiophene(Bu)–Thiophene(Bu)–Fluorene(CH₃)₂ | –C₆H₄–O–C₆H₅ |
| 107 | Fluorene–Thiophene–Thiophene–Fluorene | –C₆H₅ |
| 108 | Fluorene–Thiophene–Thiophene–Fluorene | –C₆H₃(CH₃)₂ |
| 109 | Fluorene–Thiophene–Thiophene–Fluorene | –C₆H₄–C₆H₅ |

| Structure | T | k | l | Bond Pos. |
|---|---|---|---|---|
| 104 | —CH₂CH₂— | 0 | 1 | 4 |
| 105 | —CH₂CH₂— | 0 | 1 | 4 |
| 106 | —CH₂CH₂— | 0 | 1 | 4 |
| 107 | —CH₂CH₂— | 0 | 1 | 4 |
| 108 | —CH₂— | 0 | 1 | 4 |
| 109 | —CH₂CH₂— | 0 | 1 | 4 |

TABLE 26

| Structure | X | Ar |
|---|---|---|
| 110 | Fluorene–Thiophene–Thiophene–Fluorene | 1-Naphthyl |
| 111 | Fluorene–Thiophene–Thiophene–Fluorene | –C₆H₄–Thiophene–n-C₆H₁₃ |

TABLE 26-continued

| # | Structure | Ar |
|---|---|---|
| 112 | (fluorene)-(thiophene)-(thiophene)-(fluorene) | 2,4-di(2,4-dimethylphenyl)-3,5-di(4-methylphenyl)thiophene-type substituent |
| 113 | (fluorene)-(thiophene)-(thiophene)-(fluorene) | 9,9-dimethylfluorenyl |
| 114 | (C$_8$H$_{17}$)$_2$-fluorene-(thiophene)$_3$-(C$_8$H$_{17}$)$_2$-fluorene | 4-methylphenyl |
| 115 | (C$_8$H$_{17}$)$_2$-fluorene-(thiophene)$_3$-(C$_8$H$_{17}$)$_2$-fluorene | 4-methylphenyl |

| Structure | T | k | l | Bond Pos. |
|---|---|---|---|---|
| 110 | —CH$_2$— | 0 | 1 | 4 |
| 111 | —CH$_2$— | 0 | 1 | 4 |
| 112 | —CH$_2$CH$_2$— | 0 | 1 | 4 |
| 113 | —CH$_2$CH$_2$— | 0 | 1 | 2 |
| 114 | —CH$_2$CH$_2$— | 0 | 1 | 3 |
| 115 | —CH$_2$— | 0 | 1 | 4 |

TABLE 27

| Structure | X | Ar |
|---|---|---|
| 116 | (C$_8$H$_{17}$)$_2$-fluorene-(thiophene)$_3$-(C$_8$H$_{17}$)$_2$-fluorene | 3,4-dimethylphenyl |
| 117 | (C$_8$H$_{17}$)$_2$-fluorene-(thiophene)$_3$-(C$_8$H$_{17}$)$_2$-fluorene | 4-biphenyl |
| 118 | (C$_8$H$_{17}$)$_2$-fluorene-(thiophene)$_3$-(C$_8$H$_{17}$)$_2$-fluorene | 1-naphthyl |
| 119 | (C$_8$H$_{17}$)$_2$-fluorene-(thiophene)$_3$-(C$_8$H$_{17}$)$_2$-fluorene | 9,9-dimethylfluorenyl |
| 120 | (C$_8$H$_{17}$)$_2$-fluorene-(thiophene)$_3$-(C$_8$H$_{17}$)$_2$-fluorene | 4-(5-n-hexylthiophen-2-yl)phenyl |

TABLE 27-continued

| Structure | T | k | l | Bond Pos. |
|---|---|---|---|---|
| 116 | —CH₂CH₂— | 0 | 1 | 4 |
| 117 | —(CH₂)₄— | 0 | 1 | 4 |
| 118 | —C(H₂)—C(CH₃)(CH₃)—C(H₂)— | 0 | 1 | 4 |
| 119 | —CH₂CH₂— | 0 | 1 | 4 |
| 120 | —CH₂— | 0 | 1 | 4 |
| 121 | —CH₂CH₂— | 0 | 1 | 3 |

TABLE 28

| Structure | T | k | l | Bond Pos. |
|---|---|---|---|---|
| 122 | —CH₂CH₂— | 0 | 1 | 4 |
| 123 | —CH₂CH₂— | 0 | 1 | 4 |

TABLE 28-continued

| | | | | |
|---|---|---|---|---|
| 124 | —CH₂—C(CH₃)(CH₃)—CH₂— | 0 | 1 | 4 |
| 125 | —(CH₂)₄— | 0 | 1 | 4 |
| 126 | —CH₂CH₂— | 0 | 1 | 4 |

TABLE 29

| Structure | X | Ar |
|---|---|---|
| 127 | fluorene-bithiophene-fluorene (dialkyl substituted) | 1-naphthyl |
| 128 | fluorene-bithiophene-fluorene (dialkyl substituted) | 4-(thien-2-yl)phenyl |
| 129 | fluorene-bithiophene-fluorene (dialkyl substituted) | 9,9-dimethylfluoren-2-yl |
| 130 | fluorene-bithiophene-fluorene (dialkyl substituted) | 4-styrylphenyl |
| 131 | fluorene-thiophene-fluorene (diphenyl substituted) | 2,4-dimethylphenyl |

| Structure | T | | | Bond Pos. |
|---|---|---|---|---|
| 127 | —CH₂—C(CH₃)(CH₃)—CH₂— | 0 | 1 | 4 |
| 128 | —CH₂CH₂— | 0 | 1 | 4 |
| 129 | —CH₂CH₂— | 0 | 1 | 4 |
| 130 | —CH₂CH₂— | 0 | 1 | 4 |
| 131 | —CH₂CH₂— | 0 | 1 | 4 |

TABLE 30

| Structure | X | Ar | T | k | l | Bond Pos. |
|---|---|---|---|---|---|---|
| 132 | (fluorene-thiophene-fluorene with phenyl groups) | -biphenyl- | —CH₂— | 0 | 1 | 4 |
| 133 | (fluorene-thiophene-fluorene with phenyl groups) | -naphthyl- | —CH₂CH₂— | 0 | 1 | 4 |
| 134 | (fluorene-thiophene-fluorene with phenyl groups) | -phenanthryl- | —CH₂CH₂— | 0 | 1 | 4 |
| 135 | (fluorene-thiophene-fluorene with phenyl groups) | -(9,9-dimethylfluorenyl)- | —(CH₂)₄— | 0 | 1 | 3 |
| 136 | (fluorene-thiophene-fluorene with phenyl groups) | -phenyl-thiophene-n-C₆H₁₃ | —CH₂CH₂— | 0 | 1 | 4 |

TABLE 31

| Structure | X | Ar |
|---|---|---|
| 137 | (fluorene-thiophene-fluorene with phenyl groups) | (substituted thiophene with dimethylphenyl groups and styryl) |
| 138 | (fluorene-thiophene-fluorene with phenyl groups) | -phenyl-C≡C-thiophene |
| 139 | (fluorene-thiophene-fluorene with phenyl groups) | -phenyl-O-phenyl |

TABLE 31-continued

| Structure | T | k | l | Bond Pos. |
|---|---|---|---|---|
| 137 | —CH₂CH₂— | 0 | 1 | 4 |
| 138 | —CH₂CH₂— | 0 | 1 | 4 |
| 139 | —CH₂CH₂— | 0 | 1 | 4 |
| 140 | —CH₂— | 0 | 1 | 4 |
| 141 | —CH₂CH₂— | 0 | 1 | 4 |

TABLE 32

| Structure | X | Ar | T | k | l | Bond Pos. |
|---|---|---|---|---|---|---|
| 142 | | | —CH₂CH₂— | 0 | 1 | 4 |
| 143 | | | —CH₂CH₂— | 0 | 1 | 4 |
| 144 | | | —CH₂CH₂— | 0 | 1 | 4 |
| 145 | | | —CH₂CH₂— | 0 | 1 | 4 |

TABLE 33

| Structure | X | Ar |
|---|---|---|
| 146 | (structure) | (structure) |
| 147 | (structure) | (structure) |
| 148 | (structure) | (structure) |
| 149 | (structure) | (structure) |

| Structure | T | k | l | Bond Pos. |
|---|---|---|---|---|
| 146 | —CH$_2$CH$_2$— | 0 | 1 | 4 |
| 147 | —CH$_2$CH$_2$— | 0 | 1 | 4 |
| 148 | —CH$_2$CH$_2$— | 0 | 1 | 4 |
| 149 | —CH$_2$CH$_2$— | 0 | 1 | 4 |

TABLE 34

| Structure | X | Ar |
|---|---|---|
| 150 | (structure) | (structure) |

TABLE 34-continued

| Structure | T | k | l | Bond Pos. |
|---|---|---|---|---|
| 150 | —CH₂CH₂— | 0 | 1 | 4 |
| 151 | —CH₂CH₂— | 0 | 1 | 4 |
| 152 | —CH₂CH₂— | 0 | 1 | 4 |
| 153 | —CH₂CH₂— | 0 | 1 | 4 |
| 154 | —CH₂CH₂— | 0 | 1 | 4 |
| 155 | —CH₂CH₂— | 0 | 1 | 4 |

TABLE 35

| Structure | X | Ar | T | k | l | Bond Pos. |
|---|---|---|---|---|---|---|
| 156 | | | —CH₂CH₂— | 0 | 1 | 4 |
| 157 | | | —CH₂CH₂— | 0 | 1 | 4 |
| 158 | | | —CH₂CH₂— | 0 | 1 | 4 |

TABLE 35-continued

| Structure | X | Ar | T | k | l | Bond Pos. |
|---|---|---|---|---|---|---|
| 159 | fluorene-thiophene-thiophene-fluorene (C6H13 substituents) | phenyl | —CH₂CH₂— | 0 | 1 | 4 |
| 160 | fluorene-thiophene-thiophene-fluorene (C6H13 substituents) | 2-methyl-4-methoxyphenyl (H₃C, OCH₃) | —CH₂CH₂— | 0 | 1 | 4 |
| 161 | fluorene-thiophene-thiophene-fluorene (C6H13 substituents) | biphenyl | —CH₂CH₂— | 0 | 1 | 4 |

TABLE 36

| Structure | X | Ar |
|---|---|---|
| 162 | fluorene-thiophene-thiophene-fluorene (C6H13 substituents) | 9,9-dimethylfluorene |
| 163 | fluorene-thiophene-thiophene-fluorene (C6H13 substituents) | phenyl-9,9-dimethylfluorene |
| 164 | fluorene-thiophene-thiophene-fluorene (C6H13 substituents) | phenyl-(n-C₆H₁₃-thiophene) |
| 165 | fluorene-thiophene-thiophene-fluorene (C6H13 substituents) | styryl-thiophene with two 2,4-dimethylphenyl substituents |
| 166 | fluorene-thiophene-thiophene-fluorene (C6H13 substituents) | thiophene with phenyl and two 2,4-dimethylphenyl substituents |
| 167 | fluorene-thiophene-thiophene-fluorene (C6H13 substituents) | 4-(quinolin-3-yl)phenyl |

| Structure | T | k | l | Bond Pos. |
|---|---|---|---|---|
| 162 | —CH₂CH₂— | 0 | 1 | 4 |
| 163 | —CH₂CH₂— | 0 | 1 | 4 |

TABLE 36-continued

| | | | | | |
|---|---|---|---|---|---|
| | 164 | —CH$_2$CH$_2$— | 0 | 1 | 4 |
| | 165 | —CH$_2$CH$_2$— | 0 | 1 | 4 |
| | 166 | —CH$_2$CH$_2$— | 0 | 1 | 4 |
| | 167 | —CH$_2$— | 0 | 1 | 4 |

TABLE 37

| Structure | X | Ar | T | k | l | Bond Pos. |
|---|---|---|---|---|---|---|
| 168 | [fluorene(C$_6$H$_{13}$)$_2$—thiophene—thiophene—fluorene(C$_6$H$_{13}$)$_2$] | [4-methylphenyl-N(phenyl)$_2$] | —CH$_2$CH$_2$— | 0 | 1 | 4 |

Specific examples of the structure represented by formula (I-2) above are shown below.

TABLE 38

| Structure | X | Ar | T | k | l | Bond Pos. |
|---|---|---|---|---|---|---|
| 200 | [fluorene(CH$_3$)$_2$—thiophene—fluorene(CH$_3$)$_2$] | [phenyl] | — | 1 | 0 | 3, 3' |
| 201 | [fluorene(CH$_3$)$_2$—thiophene—thiophene—fluorene(CH$_3$)$_2$] | [4-methylphenyl] | — | 1 | 0 | 3, 3' |
| 202 | [fluorene(CH$_3$)$_2$—(3,4-dimethylphenyl)thiophene—(3,4-dimethylphenyl)thiophene—fluorene(CH$_3$)$_2$] | [biphenyl] | — | 1 | 0 | 3, 3' |
| 203 | [fluorene(CH$_3$)$_2$—thiophene—thiophene—thiophene—fluorene(CH$_3$)$_2$] | [phenyl] | — | 1 | 0 | 3, 3' |
| 204 | [fluorene(CH$_3$)$_2$—thiophene—fluorene(CH$_3$)$_2$] | [biphenyl] | — | 1 | 0 | 4, 4' |
| 205 | [fluorene(CH$_3$)$_2$—thiophene—thiophene—fluorene(CH$_3$)$_2$] | [naphthyl] | — | 1 | 0 | 4, 4' |

TABLE 39

| Structure | X | Ar | T | k | l | Bond Pos. |
|---|---|---|---|---|---|---|
| 206 | (fluorene-dimethylthiophene-dimethylthiophene-fluorene, with H₃C/CH₃ on fluorenes and CH₃ groups on thiophenes) | phenyl | — | 1 | 0 | 4, 4' |
| 207 | (fluorene-thiophene-thiophene-fluorene with 3,5-dimethylphenyl substituents on thiophenes; H₃C CH₃ on fluorenes) | phenyl | — | 1 | 0 | 4, 4' |
| 208 | (fluorene-thiophene-thiophene-fluorene with phenyl substituents on thiophenes; H₃C CH₃ on fluorenes) | phenyl | — | 1 | 0 | 4, 4' |
| 209 | (fluorene-thiophene-thiophene-fluorene, with dialkyl substituents on fluorenes) | phenyl | — | 1 | 0 | 4, 4' |
| 210 | (fluorene-thiophene-fluorene, H₃C CH₃ on fluorenes) | phenyl | —CH₂— | 0 | 1 | 4, 4' |

TABLE 40

| Structure | X | Ar | T | k | l | Bond Pos. |
|---|---|---|---|---|---|---|
| 211 | (fluorene-thiophene-fluorene, H₃C CH₃ on fluorenes) | phenyl | —CH₂CH₂— | 0 | 1 | 4, 4' |
| 212 | (fluorene-thiophene-fluorene, H₃C CH₃ on fluorenes) | 3,4-dimethylphenyl | —CH₂CH₂— | 0 | 1 | 4, 4' |
| 213 | (fluorene-thiophene-fluorene, H₃C CH₃ on fluorenes) | biphenyl | —CH₂CH₂— | 0 | 1 | 4, 4' |
| 214 | (fluorene-thiophene-fluorene, H₃C CH₃ on fluorenes) | 2-methyl-4'-methoxybiphenyl | —CH₂— | 0 | 1 | 2, 2' |

TABLE 40-continued

| Structure | X | Ar | T | k | l | Bond Pos. |
|---|---|---|---|---|---|---|
| 215 | (fluorene-thiophene-fluorene with 9,9-dimethyl groups) | (1-methylnaphthalene) | —CH₂CH₂— | 0 | 1 | 3, 3' |
| 216 | (fluorene-thiophene-fluorene with 9,9-dimethyl groups) | (9,9-dimethylfluorene) | —CH₂CH₂— | 0 | 1 | 4, 4' |

TABLE 41

| Structure | X | Ar |
|---|---|---|
| 217 | | |
| 218 | | |
| 219 | | |
| 220 | | |
| 221 | | |
| 222 | | |

TABLE 41-continued

| Structure | T | k | l | Bond Pos. |
|---|---|---|---|---|
| 217 | —CH₂CH₂— | 0 | 1 | 4, 4' |
| 218 | —CH₂—C(CH₃)(CH₃)—CH₂— | 0 | 1 | 4, 4' |
| 219 | —CH₂CH₂— | 0 | 1 | 3, 3' |
| 220 | —CH₂CH₂— | 0 | 1 | 4, 4' |
| 221 | —CH₂—C(CH₃)(CH₃)—CH₂— | 0 | 1 | 4, 4' |
| 222 | —CH₂CH₂— | 0 | 1 | 4, 4' |

TABLE 42

| Structure | X | Ar |
|---|---|---|
| 223 | bis(9,9-dimethylfluorene)-thiophene | phenyl-C(CN)=CH-thiophene |
| 224 | bis(9,9-dimethylfluorene)-thiophene | phenyl-pyridine |
| 225 | bis(9,9-dimethylfluorene)-thiophene | phenyl-N(phenyl)₂ |
| 226 | bis(9,9-dimethylfluorene)-bithiophene | 2,4-dimethylphenyl |
| 227 | bis(9,9-dimethylfluorene)-bithiophene | biphenyl |
| 228 | bis(9,9-dimethylfluorene)-bithiophene | terphenyl |

TABLE 42-continued
| Structure | T | k | l | Bond Pos. |
|---|---|---|---|---|
| 223 | —CH$_2$CH$_2$— | 0 | 1 | 4, 4' |
| 224 | —C(H$_2$)—C(CH$_3$)(CH$_3$)—C(H$_2$)— | 0 | 1 | 4, 4' |
| 225 | —CH$_2$— | 0 | 1 | 4, 4' |
| 226 | —CH$_2$CH$_2$— | 0 | 1 | 4, 4' |
| 227 | —CH$_2$CH$_2$— | 0 | 1 | 4, 4' |
| 228 | —CH$_2$— | 0 | 1 | 4, 4' |
TABLE 43
| Structure | X | Ar |
|---|---|---|
| 229 | 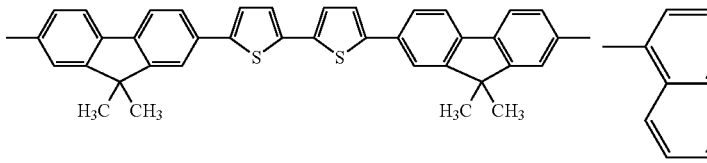 | 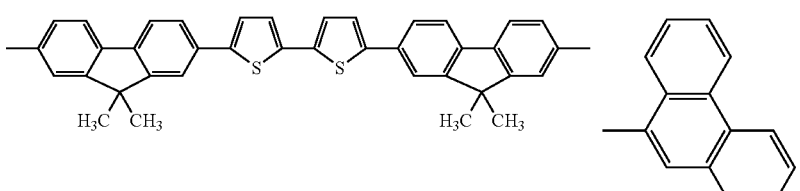 |
| 230 | 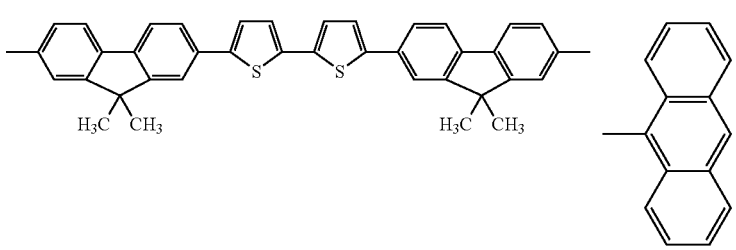 | 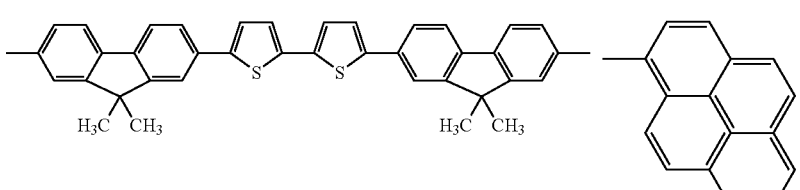 |
| 231 | 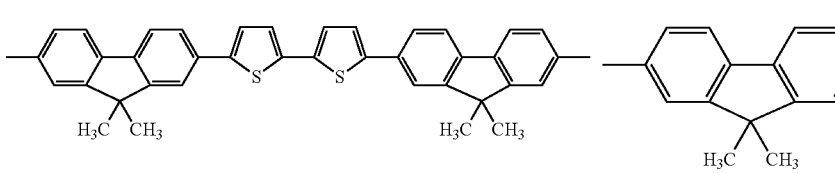 | 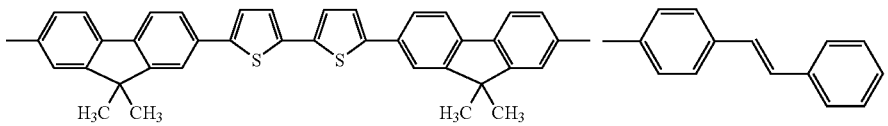 |
| 232 | | |
| 233 | | |
| 234 | | |
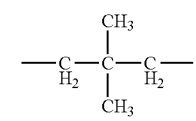

TABLE 43-continued

| Structure | T | k | l | Bond Pos. |
|---|---|---|---|---|
| 229 | —CH₂CH₂— | 0 | 1 | 4, 4' |
| 230 | —CH₂— | 0 | 1 | 4, 4' |
| 231 | —CH₂CH₂— | 0 | 1 | 4, 4' |
| 232 | —CH₂—C(CH₃)(CH₃)—CH₂— | 0 | 1 | 4, 4' |
| 233 | —CH₂CH₂— | 0 | 1 | 4, 4' |
| 234 | —CH₂CH₂— | 0 | 1 | 4, 4' |

TABLE 44

| Structure | X | Ar |
|---|---|---|
| 235 | [bis(9,9-dimethylfluorene)-bithiophene] | —C₆H₄—thiophene |
| 236 | [bis(9,9-dimethylfluorene)-bithiophene] | —C₆H₄—thiophene—n-C₆H₁₃ |
| 237 | [bis(9,9-dimethylfluorene)-bithiophene] | —C₆H₄—bithiophene |
| 238 | [bis(9,9-dimethylfluorene)-bithiophene] | —C₆H₄—oxadiazole—phenyl |
| 239 | [bis(9,9-dimethylfluorene)-dimethylbithiophene] | —phenyl |
| 240 | [bis(9,9-dimethylfluorene)-dimethylbithiophene] | —C₆H₄—CH₃ |

| Structure | T | k | l | Bond Pos. |
|---|---|---|---|---|
| 235 | —CH₂— | 0 | 1 | 4, 4' |
| 236 | —CH₂CH₂— | 0 | 1 | 3, 3' |
| 237 | —CH₂CH₂— | 0 | 1 | 4, 4' |
| 238 | —CH₂CH₂— | 0 | 1 | 4, 4' |
| 239 | —CH₂CH₂— | 0 | 1 | 4, 4' |
| 240 | —CH₂CH₂— | 0 | 1 | 4, 4' |

TABLE 45
| Structure | X | Ar |
|---|---|---|
| 241 | 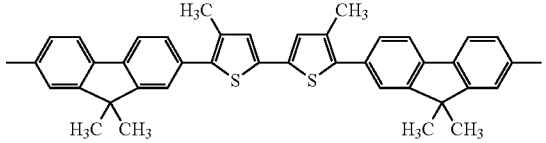 | 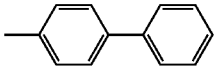 |
| 242 | 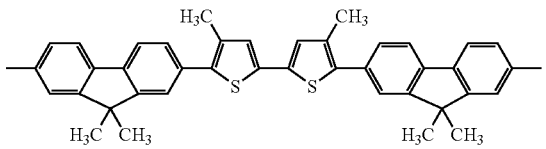 | 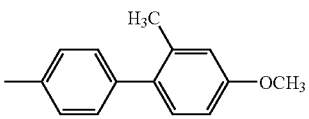 |
| 243 | 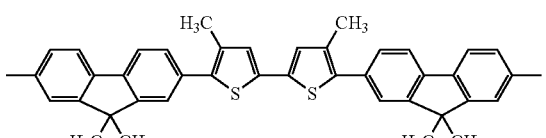 | 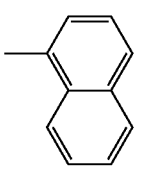 |
| 244 | 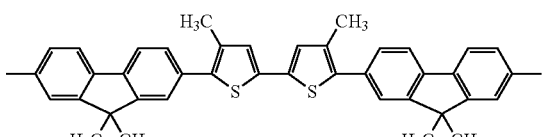 | 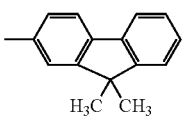 |
| 245 | 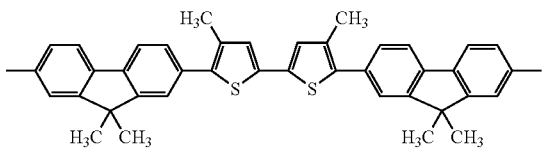 | 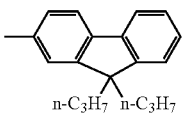 |
| 246 | 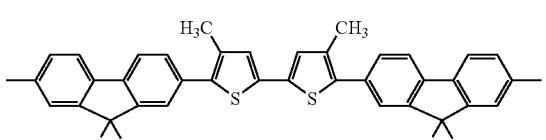 | 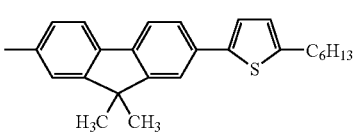 |
| Structure | T | k | l | Bond Pos. |
|---|---|---|---|---|
| 241 | —CH$_2$— | 0 | 1 | 4, 4' |
| 242 | —CH$_2$CH$_2$— | 0 | 1 | 4, 4' |
| 243 | —CH$_2$CH$_2$— | 0 | 1 | 4, 4' |
| 244 | —CH$_2$CH$_2$— | 0 | 1 | 4, 4' |
| 245 | —CH$_2$— | 0 | 1 | 3, 3' |
| 246 | —CH$_2$CH$_2$— | 0 | 1 | 4, 4' |
TABLE 46
| Structure | X | Ar |
|---|---|---|
| 247 | 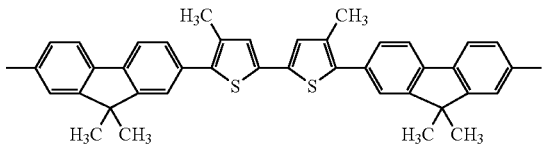 | 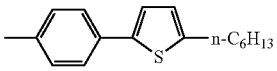 |
| 248 | 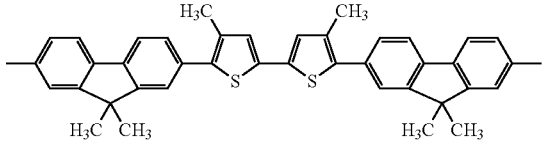 | 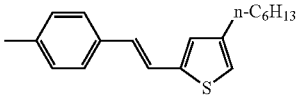 |

TABLE 46-continued

| Structure | T | k | l | Bond Pos. |
|---|---|---|---|---|
| 247 | —CH$_2$CH$_2$— | 0 | 1 | 4, 4' |
| 248 | —CH$_2$CH$_2$— | 0 | 1 | 4, 4' |
| 249 | —CH$_2$CH$_2$— | 0 | 1 | 4, 4' |
| 250 | —CH$_2$CH$_2$— | 0 | 1 | 3, 3' |
| 251 | —CH$_2$CH$_2$— | 0 | 1 | 3, 3' |
| 252 | —CH$_2$CH$_2$— | 0 | 1 | 4, 4' |

TABLE 47

| Structure | X | Ar | T | k | l | Bond Pos. |
|---|---|---|---|---|---|---|
| 253 | | | —CH$_2$CH$_2$— | 0 | 1 | 3, 3' |
| 254 | | | —CH$_2$CH$_2$— | 0 | 1 | 3, 3' |
| 255 | | | —CH$_2$CH$_2$— | 0 | 1 | 3, 3' |

TABLE 47-continued
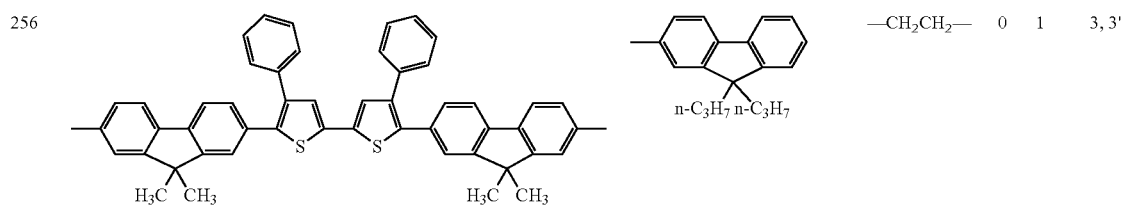
TABLE 48
| Structure | X | Ar |
|---|---|---|
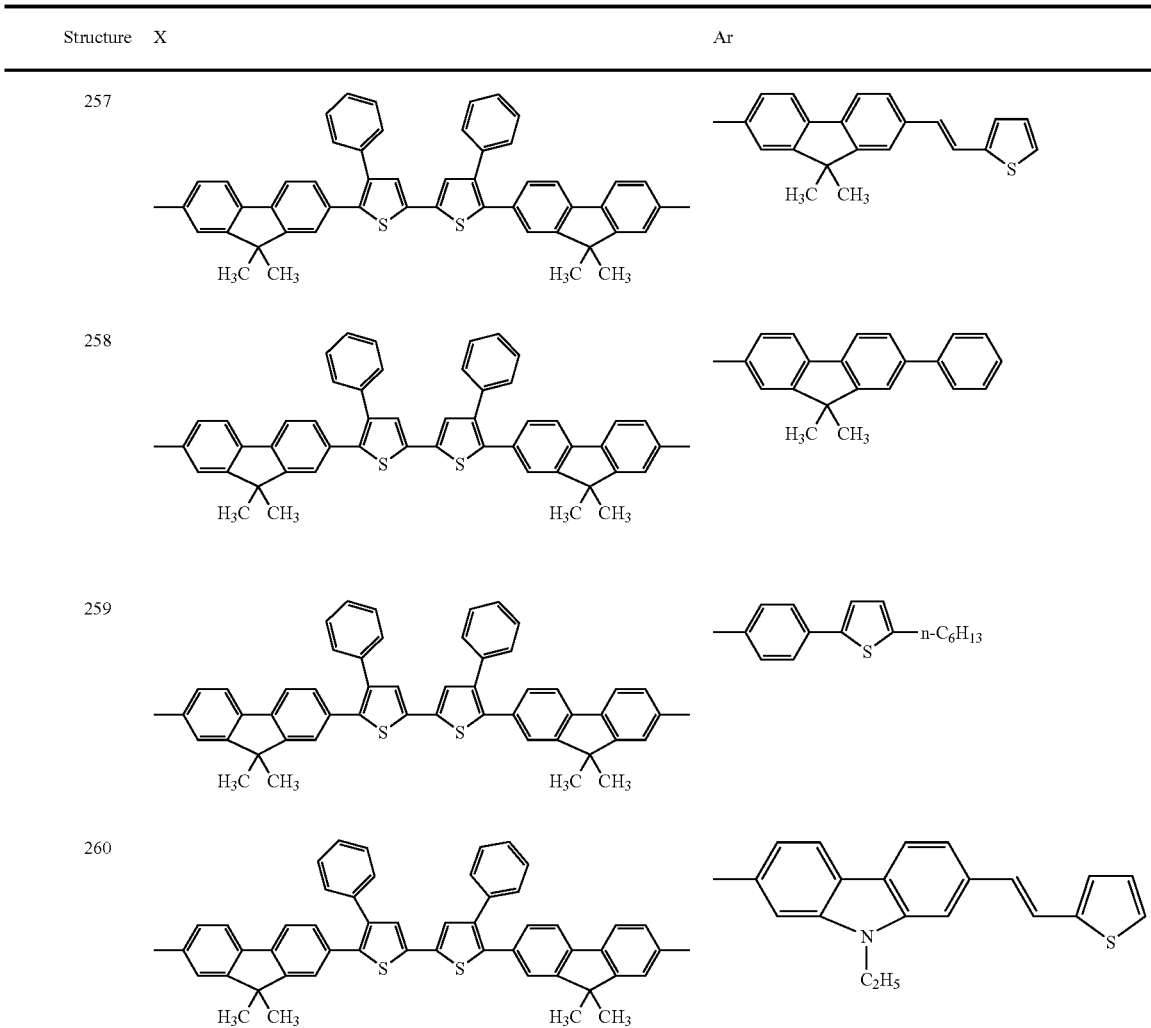
| Structure | T | k | l | Bond Pos. |
|---|---|---|---|---|
| 257 | —CH$_2$CH$_2$— | 0 | 1 | 4, 4' |
| 258 | —CH$_2$CH$_2$— | 0 | 1 | 4, 4' |
| 259 | —CH$_2$CH$_2$— | 0 | 1 | 4, 4' |
| 260 | —CH$_2$CH$_2$— | 0 | 1 | 4, 4' |

TABLE 49

| Structure | X | Ar |
|---|---|---|
| 261 | (fluorene-thiophene-thiophene-fluorene with phenyl substituents on thiophenes; 9,9-dimethyl fluorenes) | -C6H4-O-C6H5 |
| 262 | (fluorene-thiophene-thiophene-fluorene; 9,9-di-n-hexyl) | -C6H5 |
| 263 | (fluorene-thiophene-thiophene-fluorene; 9,9-di-n-hexyl) | -C6H4-CH3 (p-tolyl) |
| 264 | (fluorene-thiophene-thiophene-fluorene; 9,9-di-n-hexyl) | -2,4-dimethylphenyl |
| 265 | (fluorene-thiophene-thiophene-fluorene; 9,9-di-n-hexyl) | -biphenyl |
| 266 | (fluorene-thiophene-thiophene-fluorene; 9,9-di-n-hexyl) | -1-naphthyl |

| Structure | T | k | l | Bond Pos. |
|---|---|---|---|---|
| 261 | —CH$_2$— | 0 | 1 | 4, 4' |
| 262 | —CH$_2$CH$_2$— | 1 | 1 | 4, 4' |
| 263 | —CH$_2$CH$_2$— | 0 | 1 | 4, 4' |
| 264 | —CH$_2$CH$_2$— | 0 | 1 | 4, 4' |
| 265 | —CH$_2$CH$_2$— | 0 | 1 | 4, 4' |
| 266 | —CH$_2$— | 0 | 1 | 4, 4' |

TABLE 50

| Structure | X | Ar |
|---|---|---|
| 267 | (fluorene-thiophene-thiophene-fluorene; 9,9-di-n-hexyl) | 9-phenanthryl |
| 268 | (fluorene-thiophene-thiophene-fluorene; 9,9-di-n-hexyl) | 9,9-di-n-propylfluorenyl |

TABLE 50-continued

| Structure | T | k | l | Bond Pos. |
|---|---|---|---|---|
| 267 | —CH$_2$— | 0 | 1 | 4, 4' |
| 268 | —CH$_2$CH$_2$— | 0 | 1 | 4, 4' |
| 269 | —CH$_2$—C(CH$_3$)$_2$—CH$_2$— | 0 | 1 | 4, 4' |
| 270 | —CH$_2$CH$_2$— | 0 | 1 | 4, 4' |
| 271 | —(CH$_2$)$_4$— | 0 | 1 | 4, 4' |

TABLE 51

TABLE 51-continued

| Structure | T | k | l | Bond Pos. |
|---|---|---|---|---|
| 272 | —CH₂—C(CH₃)(CH₃)—CH₂— | 0 | 1 | 4, 4' |
| 273 | —CH₂CH₂— | 0 | 1 | 4, 4' |
| 274 | —(CH₂)₃— | 0 | 1 | 4, 4' |
| 275 | —CH₂CH₂— | 0 | 1 | 4, 4' |
| 276 | —CH₂—C(CH₃)(CH₃)—CH₂— | 0 | 1 | 4, 4' |

TABLE 52

| Structure | X | Ar |
|---|---|---|

TABLE 52-continued

| Structure | T | k | l | Bond Pos. |
|---|---|---|---|---|
| 277 | —CH$_2$CH$_2$— | 0 | 1 | 4, 4' |
| 278 | —(CH$_2$)$_3$— | 0 | 1 | 4, 4' |
| 279 | —CH$_2$CH$_2$— | 0 | 1 | 4, 4' |
| 280 | —CH$_2$—C(CH$_3$)$_2$—CH$_2$— | 0 | 1 | 4, 4' |
| 281 | —CH$_2$CH$_2$— | 0 | 1 | 4, 4' |

TABLE 53

| Structure | X | Ar |
|---|---|---|
| 282 | | |
| 283 | | |
| 284 | | |
| 285 | | |
| 286 | | |

TABLE 53-continued

| Structure | T | k | l | Bond Pos. |
|---|---|---|---|---|
| 282 | —CH₂CH₂— | 0 | 1 | 4, 4' |
| 283 | —CH₂CH₂— | 0 | 1 | 4, 4' |
| 284 | —CH₂CH₂— | 0 | 1 | 4, 4' |
| 285 | —CH₂CH₂— | 0 | 1 | 4, 4' |
| 286 | —CH₂CH₂— | 0 | 1 | 4, 4' |
| 287 | —CH₂CH₂— | 0 | 1 | 4, 4' |

TABLE 54

| Structure | T | k | l | Bond Pos. |
|---|---|---|---|---|
| 288 | —CH₂CH₂— | 0 | 1 | 4, 4' |
| 289 | —CH₂— | 0 | 1 | 4, 4' |
| 290 | —CH₂CH₂— | 0 | 1 | 4, 4' |
| 291 | —CH₂CH₂— | 0 | 1 | 4, 4' |
| 292 | —CH₂CH₂— | 0 | 1 | 4, 4' |
| 293 | —CH₂CH₂— | 0 | 1 | 4, 4' |

TABLE 55
| Structure | X | Ar |
|---|---|---|
| 294 | 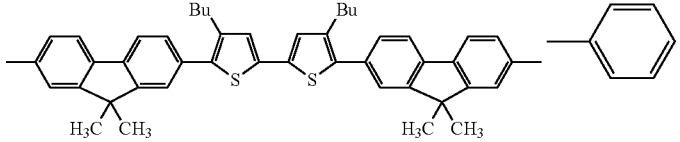 | 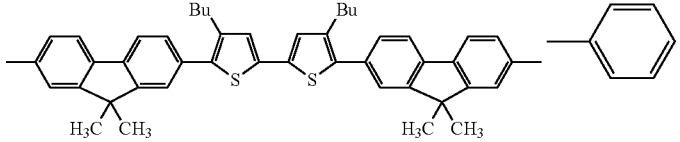 |
| 295 | 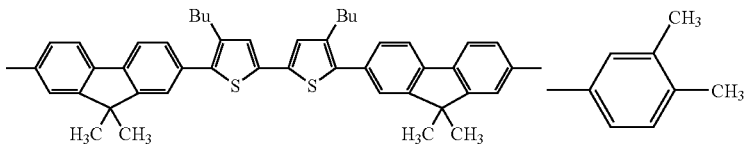 | 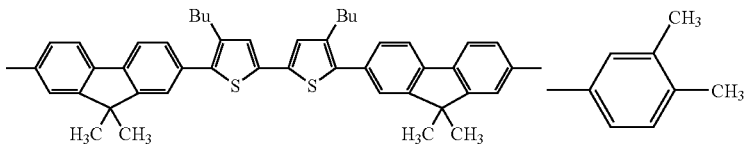 |
| 296 | 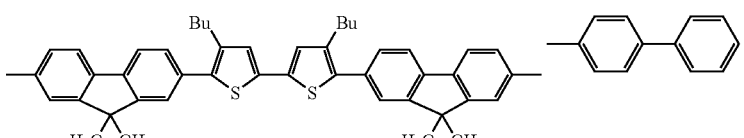 | 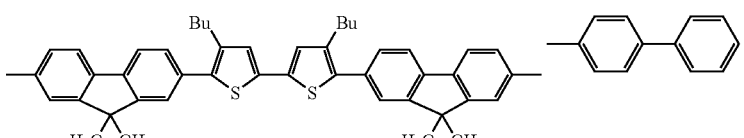 |
| 297 | 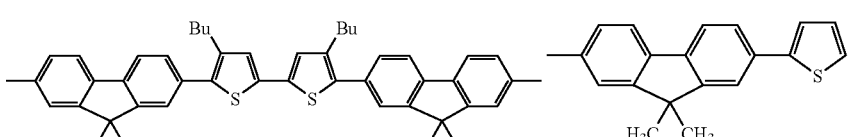 | 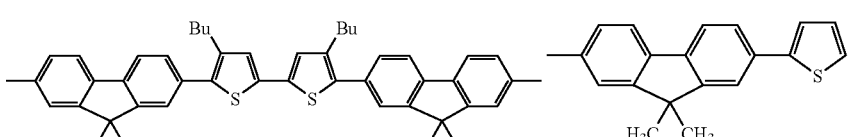 |
| 298 | 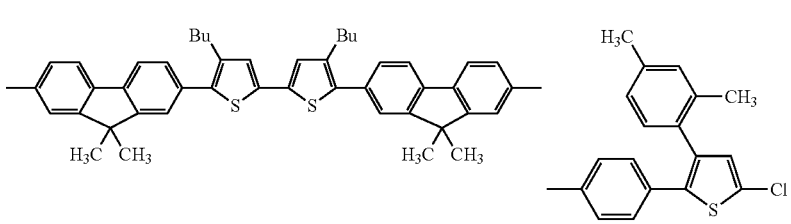 | 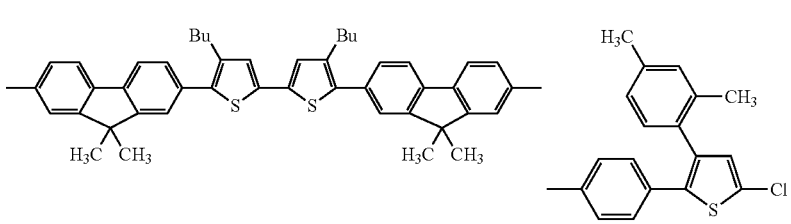 |
| 299 | 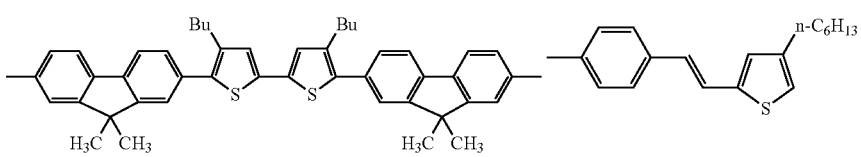 | 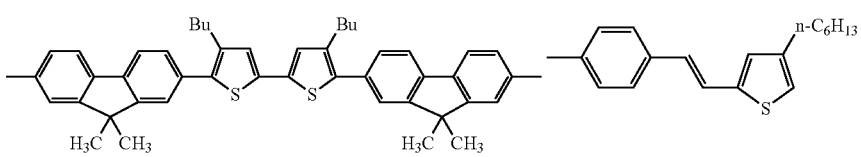 |
| Structure | T | k | l | Bond Pos. |
|---|---|---|---|---|
| 294 | —CH$_2$CH$_2$— | 0 | 1 | 4, 4' |
| 295 | —CH$_2$CH$_2$— | 0 | 1 | 4, 4' |
| 296 | —(CH$_2$)$_4$— | 0 | 1 | 4, 4' |
| 297 | —CH$_2$— | 0 | 1 | 4, 4' |
| 298 | 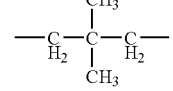 | 0 | 1 | 4, 4' |
| 299 | —CH$_2$CH$_2$— | 0 | 1 | 3, 3' |
TABLE 56
| Structure | X | Ar |
|---|---|---|
| 300 | 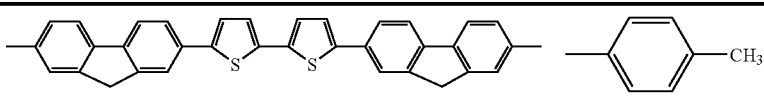 | 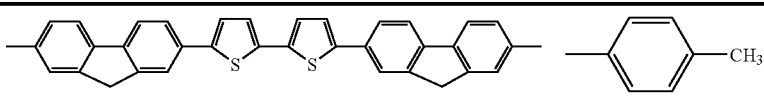 |

TABLE 56-continued

| Structure | T | k | l | Bond Pos. |
|---|---|---|---|---|
| 300 | —CH$_2$CH$_2$— | 0 | 1 | 4, 4' |
| 301 | —CH$_2$CH$_2$— | 0 | 1 | 3, 3' |
| 302 | —CH$_2$CH$_2$— | 0 | 1 | 4, 4' |
| 303 | —CH$_2$— | 0 | 1 | 4, 4' |
| 304 | —CH$_2$CH$_2$— | 0 | 1 | 4, 4' |
| 305 | —CH$_2$CH$_2$— | 0 | 1 | 4, 4' |

TABLE 57

| Structure | X | Ar |
|---|---|---|
| 306 | | |
| 307 | | |
| 308 | | |
| 309 | | |
| 310 | | |

TABLE 57-continued
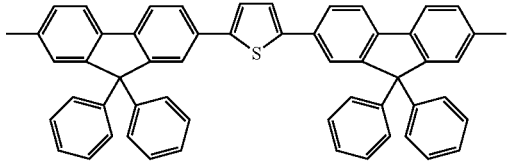
| Structure | T | k | l | Bond Pos. |
|---|---|---|---|---|
| 306 | —CH$_2$CH$_2$— | 0 | 1 | 4, 4' |
| 307 | —CH$_2$— | 0 | 1 | 4, 4' |
| 308 | —CH$_2$CH$_2$— | 0 | 1 | 4, 4' |
| 309 | —CH$_2$CH$_2$— | 0 | 1 | 4, 4' |
| 310 | —CH$_2$— | 0 | 1 | 4, 4' |
| 311 | —CH$_2$CH$_2$— | 0 | 1 | 4, 4' |
| 312 | —CH$_2$— | 0 | 1 | 4, 4' |
TABLE 58
| Structure | X | Ar |
|---|---|---|
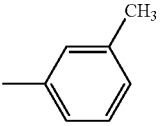

TABLE 58-continued
| | | | | | |
|---|---|---|---|---|---|
| Structure | T | | k | l | Bond Pos. |
| 313 | —CH₂CH₂— | | 0 | 1 | 4, 4' |
| 314 | —CH₂CH₂— | | 0 | 1 | 4, 4' |
| 315 | —CH₂CH₂— | | 0 | 1 | 4, 4' |
| 316 | —CH₂CH₂— | | 0 | 1 | 4, 4' |
| 317 | —CH₂CH₂— | | 0 | 1 | 4, 4' |
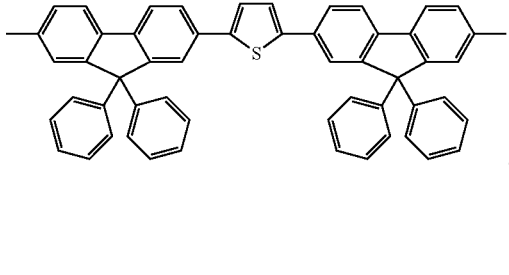
TABLE 59
| Structure | X | Ar |
|---|---|---|
| 318 | 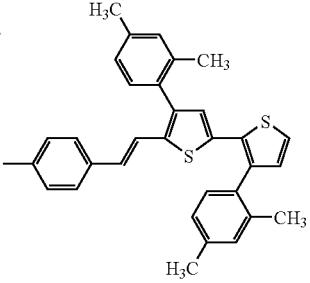 | 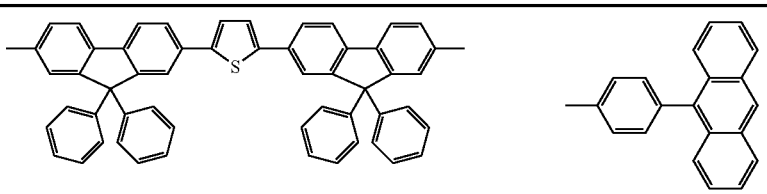 |
| 319 | 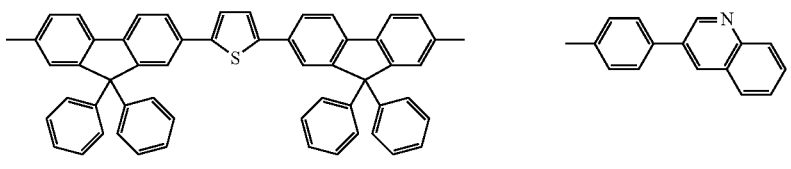 | 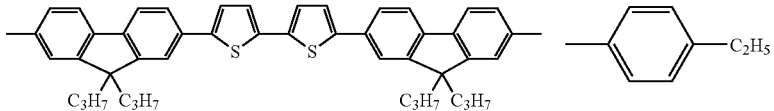 |
| 320 | 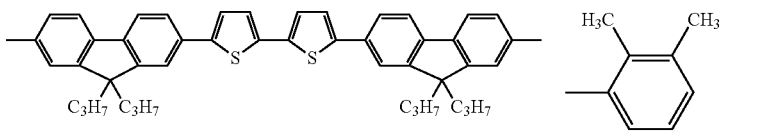 | 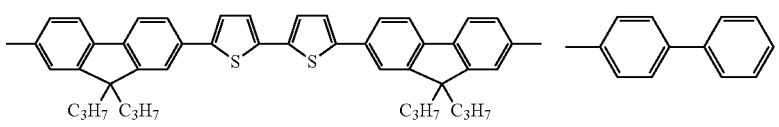 |
| 321 | 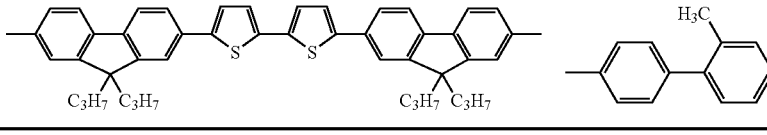 | |
| 322 | | |
| 323 | | |

TABLE 59-continued

| Structure | T | k | l | Bond Pos. |
|---|---|---|---|---|
| 318 | —CH$_2$CH$_2$— | 0 | 1 | 4, 4' |
| 319 | —CH$_2$CH$_2$— | 0 | 1 | 4, 4' |
| 320 | —CH$_2$CH$_2$— | 0 | 1 | 4, 4' |
| 321 | —CH$_2$CH$_2$— | 0 | 1 | 4, 4' |
| 322 | —CH$_2$CH$_2$— | 0 | 1 | 4, 4' |
| 323 | —CH$_2$CH$_2$— | 0 | 1 | 4, 4' |

TABLE 60

| Structure | X | Ar |
|---|---|---|
| 324 | (fluorene-C$_3$H$_7$,C$_3$H$_7$)-thiophene-thiophene-(fluorene-C$_3$H$_7$,C$_3$H$_7$) | phenanthrene |
| 325 | (fluorene-C$_3$H$_7$,C$_3$H$_7$)-thiophene-thiophene-(fluorene-C$_3$H$_7$,C$_3$H$_7$) | 9,9-dimethylfluorene |
| 326 | (fluorene-C$_3$H$_7$,C$_3$H$_7$)-thiophene-thiophene-(fluorene-C$_3$H$_7$,C$_3$H$_7$) | phenyl-thiophene-n-C$_6$H$_{13}$ |
| 327 | (fluorene-C$_3$H$_7$,C$_3$H$_7$)-thiophene-thiophene-(fluorene-C$_3$H$_7$,C$_3$H$_7$) | stilbene |
| 328 | (fluorene-C$_3$H$_7$,C$_3$H$_7$)-thiophene-thiophene-(fluorene-C$_3$H$_7$,C$_3$H$_7$) | phenyl-quinoline |
| 329 | (fluorene-C$_8$H$_{17}$,C$_8$H$_{17}$)-thiophene-thiophene-(fluorene-C$_8$H$_{17}$,C$_8$H$_{17}$) | tolyl (—C$_6$H$_4$—CH$_3$) |
| 330 | (fluorene-C$_8$H$_{17}$,C$_8$H$_{17}$)-thiophene-thiophene-(fluorene-C$_8$H$_{17}$,C$_8$H$_{17}$) | 1-naphthyl |

TABLE 60-continued

| Structure | T | k | l | Bond Pos. |
|---|---|---|---|---|
| 324 | —CH₂CH₂— | 0 | 1 | 4, 4' |
| 325 | —CH₂CH₂— | 0 | 1 | 4, 4' |
| 326 | —CH₂CH₂— | 0 | 1 | 4, 4' |
| 327 | —CH₂CH₂— | 0 | 1 | 4, 4' |
| 328 | —CH₂CH₂— | 0 | 1 | 4, 4' |
| 329 | —CH₂— | 0 | 1 | 4, 4' |
| 330 | —(CH₂)₄— | 0 | 1 | 4, 4' |

TABLE 61

| Structure | X | Ar |
|---|---|---|
| 331 | (structure) | (structure) |
| 332 | (structure) | (structure) |
| 333 | (structure) | (structure) |
| 334 | (structure) | (structure) |
| 335 | (structure) | (structure) |
| 336 | (structure) | (structure) |

TABLE 61-continued

| Structure | T | k | l | Bond Pos. |
|---|---|---|---|---|
| 331 | —CH$_2$CH$_2$— | 0 | 1 | 4, 4' |
| 332 | —CH$_2$— | 0 | 1 | 4, 4' |
| 333 | —CH$_2$CH$_2$— | 0 | 1 | 4, 4' |
| 334 | —CH$_2$CH$_2$— | 0 | 1 | 4, 4' |
| 335 | —C(H$_2$)—C(CH$_3$)(CH$_3$)—C(H$_2$)— | 0 | 1 | 4, 4' |
| 336 | —CH$_2$— | 0 | 1 | 4, 4' |

TABLE 62

| Structure | T | k | l | Bond Pos. |
|---|---|---|---|---|
| 337 | —CH$_2$— | 0 | 1 | 4, 4' |
| 338 | —CH$_2$CH$_2$— | 0 | 1 | 4, 4' |
| 339 | —CH$_2$CH$_2$— | 0 | 1 | 4, 4' |
| 340 | —C(H$_2$)—C(CH$_3$)(CH$_3$)—C(H$_2$)— | 0 | 1 | 4, 4' |

TABLE 63

| Structure | T | k | l | Bond Pos. |
|---|---|---|---|---|
| 341 | —CH₂CH₂— | 0 | 1 | 4, 4' |
| 342 | —CH₂CH₂— | 0 | 1 | 4, 4' |
| 343 | —CH₂CH₂— | 0 | 1 | 4, 4' |
| 345 | —CH₂CH₂— | 0 | 1 | 4, 4' |

TABLE 64

TABLE 64-continued

| Structure | T | k | l | Bond Pos. |
|---|---|---|---|---|
| 346 | —CH$_2$CH$_2$— | 0 | 1 | 4, 4' |
| 347 | —CH$_2$CH$_2$— | 0 | 1 | 4, 4' |
| 348 | —CH$_2$CH$_2$— | 0 | 1 | 4, 4' |

Examples of charge-transporting polyesters having a repeating structure containing at least one structure selected from the structures represented by formulae (I-1) and (I-2) as a partial structure include the polyesters represented by the following formulae (III-1) and (III-2).

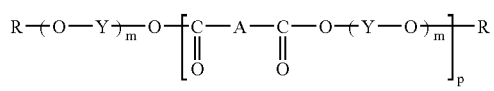

Formula (III-1)

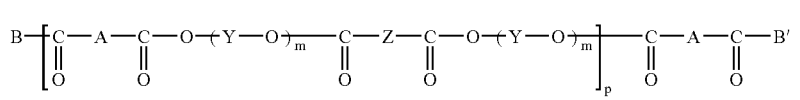

Formula (III-2)

[In formulae (III-1) and (III-2), Y and Z each independently represent a bivalent hydrocarbon group; B and B' each independently represent —O—(Y—O)$_m$—H, or —O—(Y—O)$_m$—CO-Z—CO—OR'; R and R' each independently represent a hydrogen atom, a substituted or unsubstituted alkyl group, a substituted or unsubstituted aryl group, or a substituted or unsubstituted aralkyl group; m is an integer of 1 to 5, p is an integer of 5 to 5,000; and A represents at least one of the structures represented by formulae (I-1) and (I-2) above].

In formulae (III-1) and (III-2), A represents at least one structure selected from the structures represented by formulae (I-1) and (I-2); and multiple groups A present in the polyester represented by formula (III-1) or (III-2) may have the same structure as each other or different structures from each other.

In formulae (III-1) and (III-2), R represents a hydrogen atom, a substituted or unsubstituted alkyl group, a substituted or unsubstituted aryl group, or a substituted or unsubstituted aralkyl group. The alkyl group may be a group having 1 to 10 carbon atoms, and examples thereof include a methyl group, an ethyl group, a propyl group, and an isopropyl group. The aryl group may be a group having 6 to 20 carbon atoms, and examples thereof include a phenyl group and a toluyl group. The aralkyl group may be a group having 7 to 20 carbon atoms, and examples thereof include a benzyl group and a phenethyl group.

Examples of a substituent on the group represented by each R include a hydrogen atom, alkyl groups, alkoxy groups, substituted amino groups, and halogen atoms.

In formulae (III-1) and (III-2), Y and Z each independently represent a bivalent hydrocarbon group; and, more specifically, Y represents a dihydric alcohol residue, and Z represents a bivalent carboxylic acid residue. Among them, more preferable are groups selected from the groups represented by the following formulae (IV-1) to (IV-7).

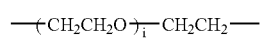 (IV-1)

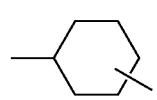 (IV-2)

—(CH$_2$CH$_2$O)$_i$—CH$_2$CH$_2$— (IV-3)

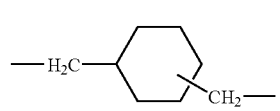 (IV-4)

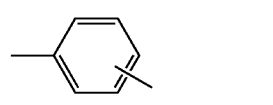 (IV-5)

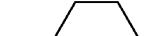 (IV-6)

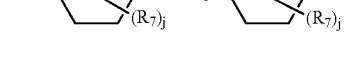 (IV-7)

[In formulae (IV-1) to (IV-7) above, R$^1$ and R$^2$ each independently represent a hydrogen atom, a substituted or unsubstituted alkyl group having 1 to 4 carbon atoms, a substituted or unsubstituted alkoxy group having 1 to 4 carbon atoms, a substituted or unsubstituted phenyl group, or a substituted or unsubstituted aralkyl group; each of a and b is independently an integer of 1 to 5; each of d and f is independently 0 or 1; each of c and e is independently an integer of 0 to 2; and V represents a group represented by one of the following formulae (V-1) to (V-11)].

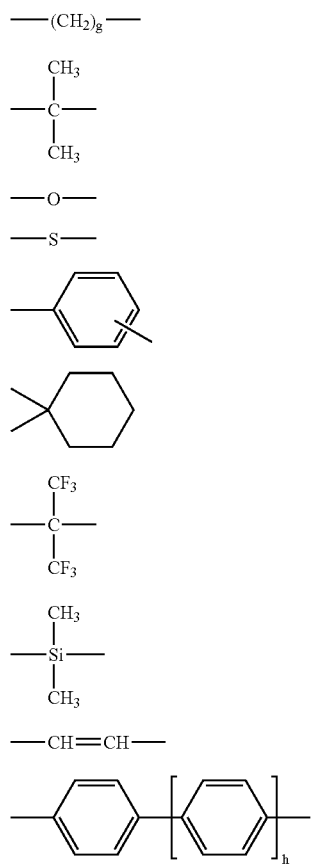

-continued

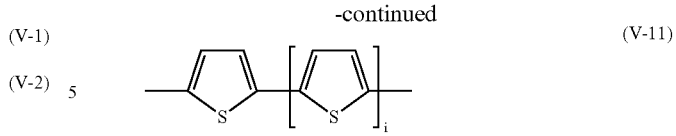

[In formulae (V-1), (V-10) and (V-11) above, g is an integer of 1 to 5, and each of h and i is independently an integer of 0 to 5].

In formulae (III-1) and (III-2), B and B' each independently represent —O—(Y—O)$_m$—H, or —O—(Y—O)$_m$—CO-Z-CO—OR'. R' has the same definition as R described above, and exemplary range thereof may be also the same.

In formulae (III-1) and (III-2), m is an integer of 1 to 5; and p is an integer of 5 to 5,000, preferably in the range of 10 to 1,000.

Hereinafter, specific examples of the charge-transporting polyesters represented by formulae (III-1) and (III-2) will be listed below, but the invention is not limited by these specific examples. The numbers in the column for monomer A in the following Tables correspond to the structure numbers of the specific examples of the structures represented by formula (I-1) and (I-2). The polymers having "-" in column Z are specific examples of the charge-transporting polyester represented by formula (III-1), and the other polymers are specific examples of the charge-transporting polyester represented by formula (III-2).

Each specific example of the charge-transporting polyester compound has an identification number in the following Tables, and a specific example with a number, for example, of 15 will be called "charge-transporting polyester (15)" hereinafter.

TABLE 65

| Polymer | Monomer A | Ratio | Y | Z | m | R/B, B' | p |
|---|---|---|---|---|---|---|---|
| (1) | 1 | — | —CH$_2$CH$_2$— | — | 1 | H | 78 |
| (2) | 5 | — | —CH$_2$CH$_2$— | — | 1 | H | 59 |
| (3) | 5 | — | -⌬-CH$_2$-⌬- | — | 1 | H | 105 |
| (4) | 5 | — | —CH$_2$CH$_2$— | -⌬- | 1 | —OC$_2$H$_4$OH | 48 |
| (5) | 9 | — | -⌬- | — | 1 | H | 79 |
| (6) | 14 | — | —CH$_2$CH$_2$— | — | 1 | H | 80 |
| (7) | 15 | — | —(CH$_2$)$_6$— | — | 1 | H | 100 |
| (8) | 17 | — | —CH$_2$CH$_2$— | — | 1 | H | 102 |
| (9) | 20 | — | —CH$_2$CH$_2$— | — | 1 | H | 98 |
| (10) | 25 | — | —CH$_2$CH$_2$— | — | 1 | H | 83 |
| (11) | 25 | — | H$_2$C-⌬-CH$_2$ | — | 1 | H | 57 |

TABLE 65-continued
| Polymer | Monomer A | Ratio | Y | Z | m | R/B, B' | p |
|---|---|---|---|---|---|---|---|
| (12) | 30 | — | —CH₂CH₂— | — | 1 | H | 79 |
| (13) | 29 | — | —CH₂CH₂— | — | 1 | H | 97 |
| (14) | 29 | — | —(CH₂)₆— | — | 1 | H | 124 |
| (15) | 29 | — | 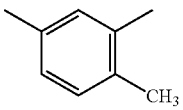 | — | 1 | H | 121 |
| (16) | 35 | — | 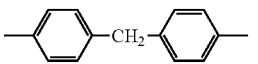 | — | 1 | H | 69 |
| (17) | 35 | — | —CH₂CH₂— | 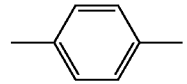 | 1 | —OC₂H₄OH | 98 |
| (18) | 35 | — | 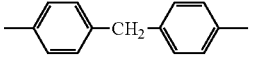 | — | 1 | H | 60 |
| (19) | 29 | — | 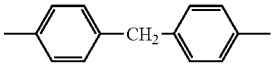 | — | 1 | H | 100 |
| (20) | 32 | — | —CH₂CH₂— | — | 1 | H | 140 |
| (21) | 48 | — |  | — | 1 | H | 123 |
| (22) | 49 | — | 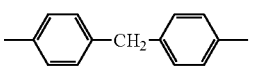 | — | 1 | H | 108 |
| (23) | 50 | — | 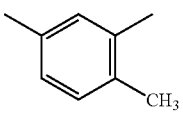 | — | 1 | H | 104 |
| (24) | 50 | — | —CH₂CH₂— | 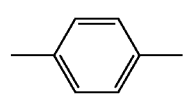 | 1 | —OC₂H₄OH | 68 |
| (25) | 60 | — | —(CH₂)₆— | — | 1 | H | 59 |
TABLE 66
| Polymer | Monomer A | Ratio | Y | Z | m | R/B, B' | p |
|---|---|---|---|---|---|---|---|
| (26) | 66 | — | —CH₂CH₂— | — | 1 | H | 96 |
| (27) | 70 | — | —CH₂CH₂— | — | 1 | H | 80 |
| (28) | 70 | — | 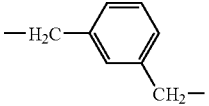 | — | 1 | H | 101 |
| (29) | 70 | — | —CH₂CH₂— | 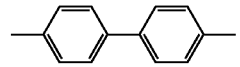 | 1 | —OC₂H₄OH | 79 |
| (30) | 70 | — | —(CH₂)₆— | — | 1 | H | 96 |

TABLE 66-continued

| Polymer | Monomer A | Ratio | Y | Z | m | R/B, B' | p |
|---|---|---|---|---|---|---|---|
| (31) | 73 | — | -C₆H₄-CH₂-C₆H₄- | — | 1 | H | 86 |
| (32) | 75 | — | —CH₂CH₂— | — | 1 | H | 80 |
| (33) | 79 | — | —CH₂CH₂— | -C₆H₄- | 1 | —OC₂H₄OH | 60 |
| (34) | 79 | — | -cyclohexyl- | — | 1 | H | 95 |
| (35) | 81 | — | —(CH₂)₆— | — | 1 | H | 40 |
| (36) | 81 | — | -C₆H₄-CH₂-C₆H₄- | — | 1 | H | 120 |
| (37) | 95 | — | —CH₂CH₂— | — | 1 | H | 107 |
| (38) | 95 | — | —(CH₂)₆— | — | 1 | H | 101 |
| (39) | 101 | — | H₂C-cyclohexyl-CH₂ | — | 1 | H | 68 |
| (40) | 105 | — | —CH₂CH₂— | — | 1 | H | 70 |
| (41) | 115 | — | —CH₂CH₂— | -C₆H₄-C₆H₄- | 1 | —OC₂H₄OH | 89 |
| (42) | 116 | — | —CH₂CH₂— | — | 1 | H | 69 |
| (43) | 117 | — | -cyclohexyl- (1,2) | — | 1 | H | 92 |
| (44) | 118 | — | —CH₂CH₂— | — | 1 | H | 85 |
| (45) | 119 | — | —CH₂CH₂— | — | 1 | H | 100 |
| (46) | 120 | — | -C₆H₄-CH₂-C₆H₄- | — | 1 | H | 69 |
| (47) | 125 | — | —CH₂CH₂— | — | 1 | H | 95 |
| (48) | 127 | — | —CH₂CH₂— | — | 1 | H | 98 |
| (49) | 129 | — | —CH₂CH₂— | -C₆H₄-C₆H₄- | 1 | —OC₂H₄OH | 111 |

TABLE 67

| Polymer | Monomer A | Ratio | Y | Z | m | R/B, B' | p |
|---|---|---|---|---|---|---|---|
| (50) | 135 | — | —CH₂CH₂— | — | 1 | H | 81 |
| (51) | 135 | — | -cyclohexyl- | — | 1 | H | 88 |
| (52) | 141 | — | —CH₂CH₂— | — | 1 | H | 69 |

TABLE 67-continued

| Polymer | Monomer A | Ratio | Y | Z | m | R/B, B' | p |
|---|---|---|---|---|---|---|---|
| (53) | 141 | — | 1,4-cyclohexylene | — | 1 | H | 49 |
| (54) | 141 | — | —C₆H₄—CH₂—C₆H₄— | — | 1 | H | 49 |
| (55) | 144 | — | —CH₂CH₂— | — | 1 | H | 93 |
| (56) | 146 | — | —(CH₂)₆— | — | 1 | H | 89 |
| (57) | 147 | — | —CH₂CH₂— | — | 1 | H | 101 |
| (58) | 147 | — | —(CH₂)₆— | 1,4-phenylene | 1 | —OC₂H₄OH | 101 |
| (59) | 147 | — | 1,4-cyclohexylene | — | 1 | H | 101 |
| (60) | 149 | — | —CH₂CH₂— | — | 1 | H | 101 |
| (61) | 152 | — | —CH₂CH₂— | — | 1 | H | 69 |
| (62) | 156 | — | 1,4-cyclohexylene | — | 1 | H | 90 |
| (63) | 201 | — | —CH₂—C(CH₃)₂—CH₂— | — | 1 | H | 95 |
| (64) | 206 | — | —CH₂CH₂— | 1,4-phenylene | 1 | —OC₂H₄OH | 65 |
| (65) | 208 | — | —CH₂CH₂— | — | 1 | H | 109 |
| (66) | 214 | — | —CH₂CH₂— | — | 1 | H | 82 |
| (67) | 221 | — | —H₂C—C₆H₄—CH₂— (1,3-) | — | 1 | H | 77 |
| (68) | 234 | — | —CH₂CH₂— | — | 1 | H | 85 |
| (69) | 234 | — | —CH₂CH₂— | 4,4'-biphenylene | 1 | —OC₂H₄OH | 98 |
| (70) | 255 | — | —CH₂CH₂— | — | 1 | H | 82 |
| (71) | 270 | — | —CH₂CH₂— | — | 1 | H | 60 |
| (72) | 278 | — | —CH₂CH₂— | — | 1 | H | 82 |
| (73) | 279 | — | —CH₂CH₂— | 4,4'-biphenylene | 1 | —OC₂H₄OH | 82 |
| (74) | 290 | — | —CH₂CH₂— | — | 1 | H | 82 |

TABLE 68

| Polymer | Monomer A | Ratio | Y | Z | m | R/B, B' | p |
|---|---|---|---|---|---|---|---|
| (75) | 339 | — | —CH₂CH₂— | — | 1 | H | 72 |
| (76) | 23/31 | 1/1 | —CH₂CH₂— | — | 1 | H | 66 |
| (77) | 23/35 | 1/1 | —CH₂CH₂— | — | 1 | H | 90 |
| (78) | 23/37 | 1/1 | —CH₂CH₂— | — | 1 | H | 109 |
| (79) | 25/37 | 1/1 | —CH₂CH₂— | — | 1 | H | 89 |
| (80) | 38/56 | 1/1 | —CH₂CH₂— | — | 1 | H | 60 |
| (81) | 38/58 | 1/1 | —CH₂CH₂— | — | 1 | H | 97 |
| (82) | 38/60 | 1/1 | *1,4-cyclohexylene* | — | 1 | H | 92 |
| (83) | 38/88 | 1/1 | —CH₂CH₂— | — | 1 | H | 115 |
| (84) | 49/60 | 1/1 | —CH₂CH₂— | — | 1 | H | 101 |
| (85) | 49/65 | 1/1 | —CH₂CH₂— | *1,4-phenylene* | 1 | —OC₂H₄OH | 47 |
| (86) | 49/88 | 1/1 | —C(CH₃)₂—C(CH₃)₂— (neopentylene: —CH₂—C(CH₃)₂—CH₂—) | — | 1 | H | 76 |
| (87) | 49/88 | 1/1 | —CH₂CH₂— | — | 1 | H | 99 |
| (88) | 55/90 | 1/1 | —CH₂CH₂— | — | 1 | H | 111 |
| (89) | 55/95 | 1/1 | —CH₂CH₂— | *4,4'-biphenylene* | 1 | —OC₂H₄OH | 67 |
| (90) | 60/75 | 1/1 | *1,4-cyclohexylene* | — | 1 | H | 52 |
| (91) | 60/86 | 1/1 | —CH₂CH₂— | — | 1 | H | 116 |
| (92) | 63/88 | 1/1 | —H₂C—(1,3-phenylene)—CH₂— | — | 1 | H | 86 |
| (93) | 63/90 | 1/1 | —CH₂CH₂— | — | 1 | H | 120 |
| (94) | 63/95 | 1/1 | —CH₂CH₂— | *1,4-phenylene* | 1 | —OC₂H₄OH | 52 |
| (95) | 88/90 | 1/1 | —CH₂CH₂— | — | 1 | H | 89 |
| (96) | 88/95 | 1/1 | —CH₂CH₂— | — | 1 | H | 58 |
| (97) | 120/130 | 1/1 | —CH₂CH₂— | — | 1 | H | 99 |
| (98) | 120/155 | 1/1 | —CH₂CH₂— | — | 1 | H | 95 |
| (99) | 120/130 | 1/1 | —(CH₂)₆— | — | 1 | H | 78 |

TABLE 69

| Polymer | Monomer A | Ratio | Y | Z | m | R/B, B' | p |
|---|---|---|---|---|---|---|---|
| (100) | 120/155 | 1/1 | —CH₂CH₂— | *4,4'-biphenylene* | 1 | —OC₂H₄OH | 81 |
| (101) | 128/180 | 1/1 | —CH₂CH₂— | — | 1 | H | 80 |

TABLE 69-continued

| Polymer | Monomer A | Ratio | Y | Z | m | R/B, B' | p |
|---|---|---|---|---|---|---|---|
| (102) | 128/150 | 1/1 | H₂C—⟨cyclohexyl⟩—CH₂ | — | 1 | H | 104 |
| (103) | 135/155 | 1/1 | —(CH₂)₆— | — | 1 | H | 58 |

The weight-average molecular weight Mw of the charge-transporting polyester is preferably in the range of 5,000 to 1,000,000, more preferably in the range of 10,000 to 300,000.

The weight-average molecular weight Mw can be determined by the following method. The weight-average molecular weight Mw can be determined by preparing a THF solution of 1.0 wt % charge-transporting polymer and analyzing the solution by gel permeation chromatography (GPC) in a differential refractometer (RI) while using styrene polymers as the standard sample.

(Method of Preparing Charge-Transporting Polyester)

The charge-transporting polyester represented by formula (III-1) or (III-2) can be prepared, for example, by polymerization of a charge-transporting monomer represented by the following formula (VI-1) or (VI-2) according to a known method such as the method described in New Experimental Chemistry 4th Ed., No. 28 (the Chemical Society of Japan Ed., Maruzen, 1992).

Formula (VI-1)

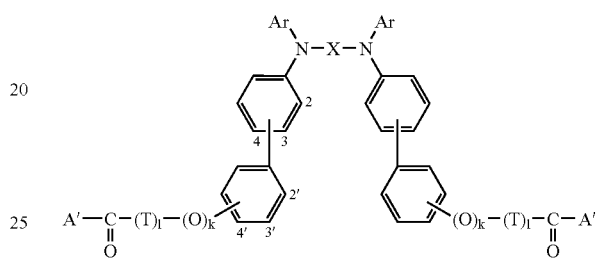

-continued

Formula (VI-2)

[In formulae (VI-1) and (VI-2), Ar, X, T, k, and l respectively have the same definitions as Ar, X, T, k, l in formulae (I-1) and (I-2); and A' represents a hydroxyl group, a halogen atom, or —O—R (R represents a substituted or unsubstituted alkyl group, a substituted or unsubstituted aryl group, or a substituted or unsubstituted aralkyl group)].

The method of preparing the electric charge-transporting monomer represented by formula (VI-1) or (VI-2) will be described first. The raw material monomer for the charge-transporting polymer according to an aspect of the invention can prepared, for example, in the following manner, but the method is not limited thereto.

An arylamine derivative and a halogenated carboalkoxyalkylbenzene, or an aryl halide and a carboalkoxyaniline derivative, are allowed to react with each other to form a diarylamine, and then, the diarylamine is allowed to react with a bis-halogenated aryl.

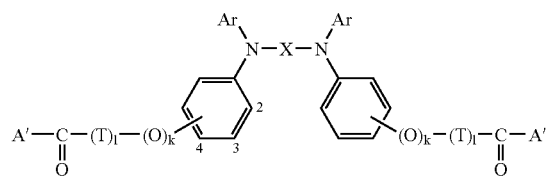

Diarylamine (DAA)

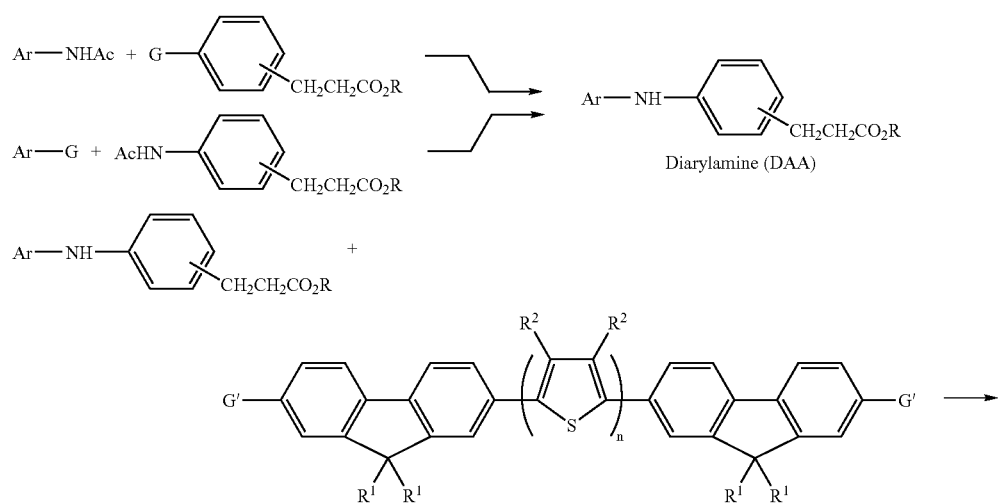

-continued

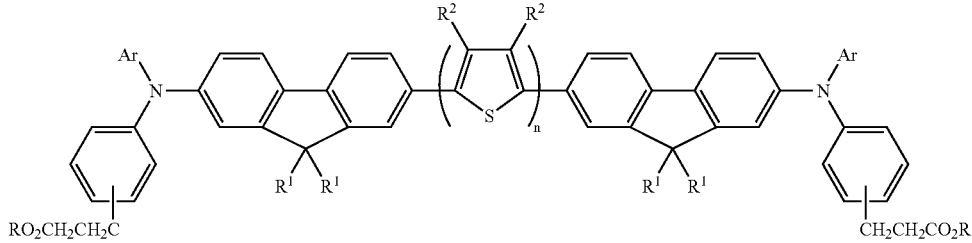

[In the reaction formula, G and G' each independently represent an iodine or bromine atom; Ar has the same definition as Ar in formulae (I-1) and (I-2) above; and $R^1$, $R^2$, and n respectively have the same definitions as $R^1$, $R^2$, and n in formula (II), and their exemplary ranges may be also the same; and R has the same definition as R in formulae (VI-1) and (VI-2), and exemplary range thereof may be also the same].

Alternatively, an arylamine derivative or a benzidine derivative is allowed to react with a halogenated carboalkoxyalkylbenzene to give a diarylamine, and the diarylamine obtained is allowed to react with an aryl halide.

[In the reaction formula, G and G' each independently represent an iodine or bromine atom; Ar has the same definition as Ar in formulae (I-1) and (I-2) above; $R^1$, $R^2$, and n respectively have the same definitions as $R^1$, $R^2$, and in formula (II), and exemplary ranges thereof may be also the same; and R has the same definition as R in formulae (VI-1) and (VI-2), and exemplary range thereof may be also the same].

When n is an even number, a triarylamine compound can be prepared in a similar manner to the method above, and a diarylamine can be prepared by homo-coupling thereof, for example, in the presence of a nickel catalyst.

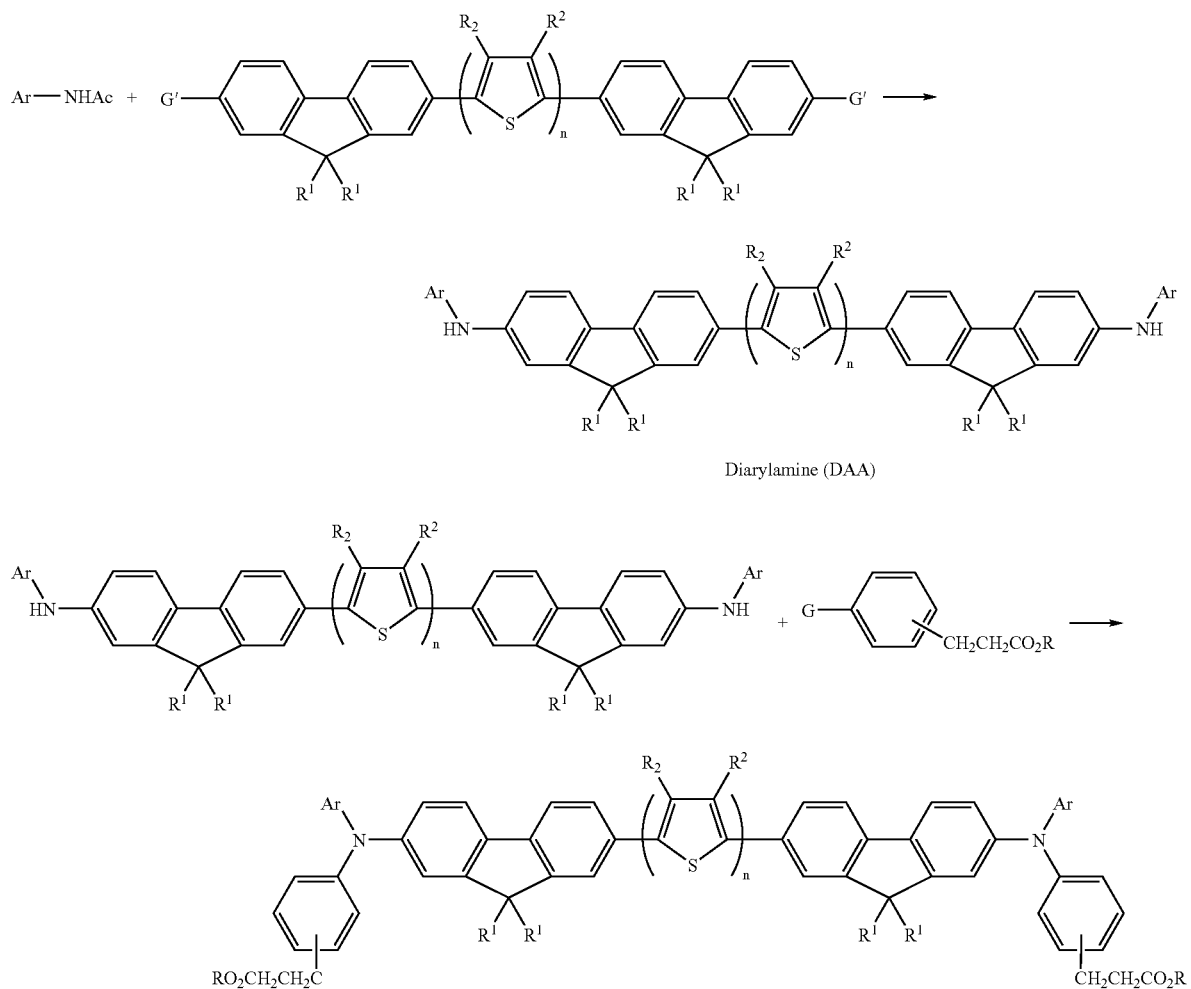

Diarylamine (DAA)

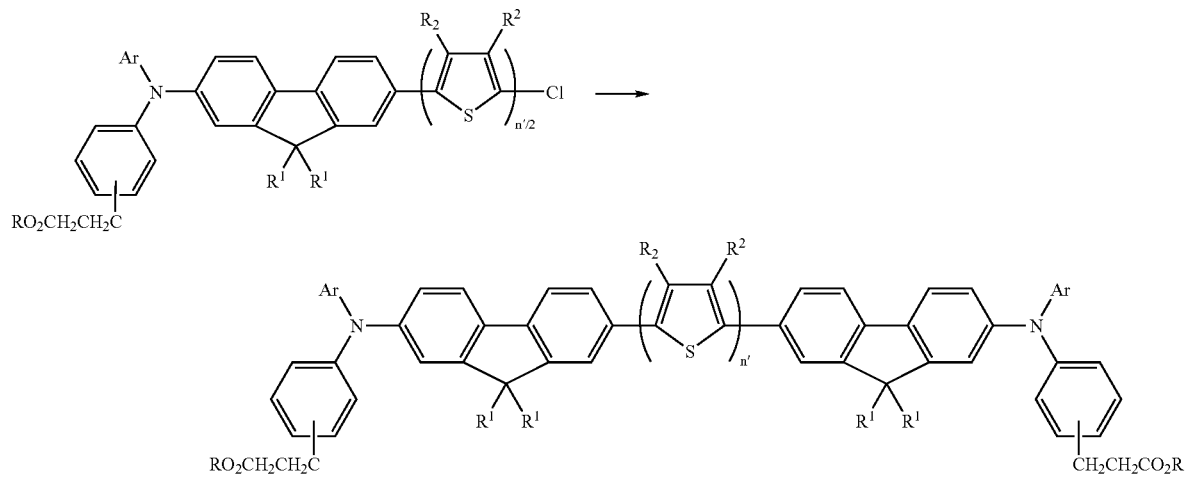

[In the reaction formula, Ar has the same definition as Ar in formulae (I-1) and (I-2), and exemplary range thereof may be also the same; $R^1$ and $R^2$ have the same definitions as $R^1$ and $R^2$ in formula (II), and exemplary ranges thereof may be also the same; and R has the same definition as R in formulae (VI-1) and (VI-2), and exemplary range thereof may be also the same; and n' is an even integer in the range of 1 to 10].

It is possible to prepare charge-transporting polyesters represented by formulae (III-1) and (III-2) above by polymerizing the obtained charge-transporting monomers represented by formula (VI-1) and (VI-2) according to a known method. Specifically, the above-described methods of preparing the thiophene-containing compound polymers represented by formulae (X-II-1) and (X-II-2) may be used.

The charge-transporting polyesters represented by formulae (III-1) and (III-2) can be prepared in the following manner: In all cases among [1] to [3] described in the above methods, the compound represented by the following formula (VII-1) or (VII-2) is formed in reaction in the presence of excess dihydric alcohol, and the compound is allowed to react as the monomer, for example, with a bivalent carboxylic acid or a bivalent carboxylic halide by a method similar to [2], to give a polymer.

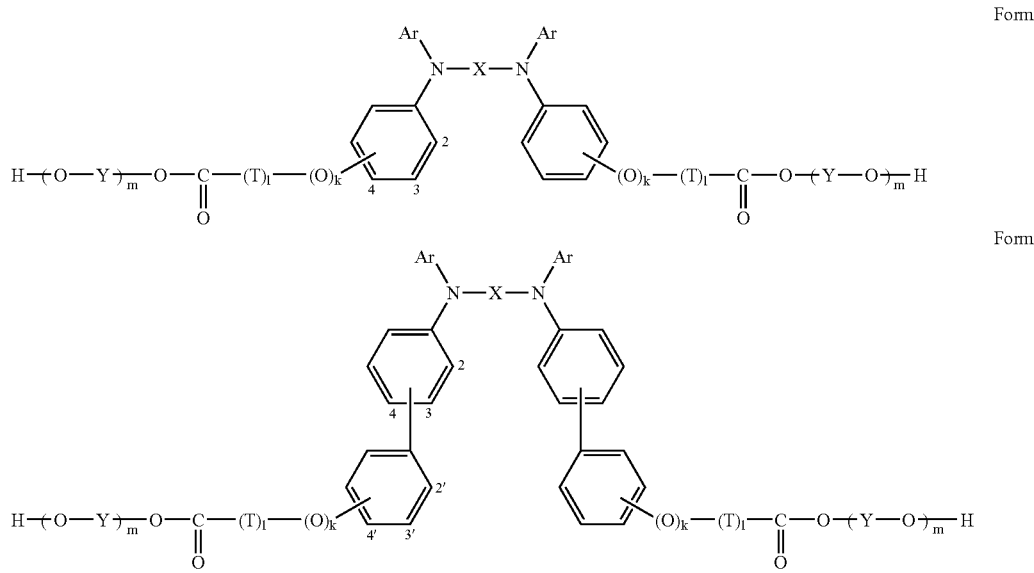

Formula (VII-1)

Formula (VII-2)

[In formulae (VII-1) and (VII-2), Ar, X, T, l, and k respectively have the same definitions as Ar, X, T, l, and k in formulae (I-1) and (I-2) above, and exemplary ranges thereof may be also the same; and Y and m respectively have the same definitions as Y and m in formulae (III-1) and (III-2) above, and exemplary ranges thereof may be also the same].

—Organic Electroluminescent Device—

Hereinafter, the organic electroluminescent device according to an aspect of the invention will be described in detail.

The layer structure of the organic electroluminescent device according to the aspect of the invention is not particularly limited if the device has a pair of electrodes, at least one of which is transparent or semitransparent, and one or multiple organic compound layers provided between the electrodes, and at least one of the organic compound layers contains at least one charge-transporting polyester described above.

When the organic electroluminescent device according to the aspect of the invention has one organic compound layer, the organic compound layer means a light-emitting layer having electric charge-transporting ability, and the light-emitting layer contains the above charge-transporting polyester. On the other hand when there are multiple organic compound layers (i.e., when the device is a function-separation-type device in which each layer has a different function), at least one of the layers is a light-emitting layer, and the light-emitting layer may be a light-emitting layer having electric charge-transporting ability. Specific examples of the layer structure consisting of the light-emitting layer or the light-emitting layer having electric charge-transporting ability and other layers in such a case include the followings (1) to (3).

(1) Layer structure consisting of a light-emitting layer and an electron transport layer and/or an electron injection layer.

(2) Layer structure consisting of a hole transport layer and/or a hole injection layer, a light-emitting layer, and an electron transport layer and/or and electron injection layer.

(3) Layer structure consisting of a hole transport layer and/or a hole injection layer, and a light-emitting layer.

The other layers than the light-emitting layer and the light-emitting layer having electric charge-transporting ability in these layer structures (1) to (3) have a function as a charge transport layer or as a charge injection layer.

In each of the layer structures (1) to (3), one of the layers may contain the charge-transporting polyester.

In the organic electroluminescent device according to the aspect of the invention, the light-emitting layer, hole transport layer, hole injection layer, electron transport layer, or electron injection layer may contain additionally a charge-transporting compound other than the charge-transporting polyester (hole-transporting material or electron-transporting material). Details of such a charge-transporting compound will be described below.

Hereinafter, the invention will be described more in detail with reference to drawings, but the invention is not limited thereto.

Figure 9:
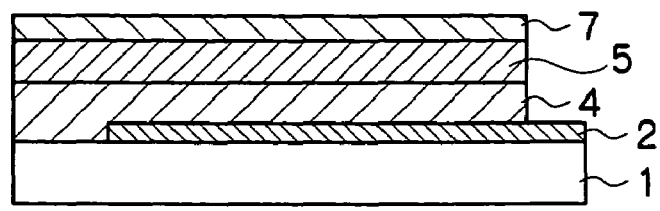
FIG. 9 is a schematic sectional view illustrating an example of the layer structure of an organic electroluminescent device according to an aspect of the present invention.
Figure 10:
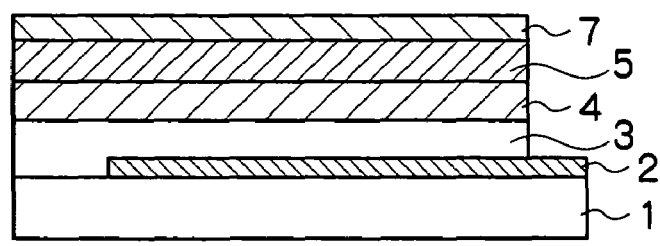
FIG. 10 is a schematic sectional view illustrating an example of the layer structure of another organic electroluminescent device according to an aspect of the invention.
Figure 11:
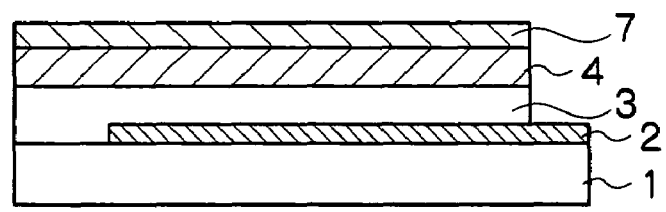
FIG. 11 is a schematic sectional view illustrating an example of the layer structure of yet another organic electroluminescent device according to an aspect of the invention.
Figure 12:
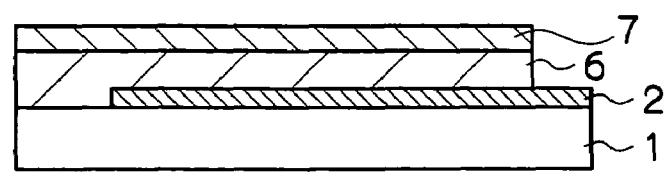
FIG. 12 is a schematic sectional view illustrating an example of the layer structure of yet another organic electroluminescent device according to an aspect of the invention.

FIGS. 9 to 12 are schematic sectional views illustrating the layer structure of the organic electroluminescent devices according to aspects of the invention, and FIGS. 9, 10, and 11 show examples in the case where there are multiple organic compound layers. FIG. 12 shows an example in the case where there is one organic compound layer. In FIGS. 9 to 12, the same reference character is allocated to members having the same function.

The organic electroluminescent device shown in FIG. 9 has a transparent insulator substrate 1, and a transparent electrode 2, a light-emitting layer 4, an electron transport layer and/or an electron injection layer 5, and a back electrode 7 formed thereon in that order, and thus, has a layer structure corresponding to the layer structure (1). However, when the layer of reference character 5 is an electron transport layer and an electron injection layer, the electron transport layer, the electron injection layer, and the back electrode 7 are laminated in that order at the back electrode 7 side of the light-emitting layer 4.

The organic electroluminescent device shown in FIG. 10 has a transparent insulator substrate 1, and a transparent electrode 2, a hole transport layer and/or a hole injection layer 3, a light-emitting layer 4, an electron transport layer and/or an electron injection layer 5, and a back electrode 7 formed thereon in that order, and thus, have a layer structure corresponding to layer structure (2). However, when the layer indicated by reference character 3 is a hole transport layer and a hole injection layer, the hole injection layer, the hole transport layer, and a light-emitting layer 4 are laminated in that order on the back electrode 7 side of the transparent electrode 2. When the layer indicated by reference character 5 is an electron transport layer and an electron injection layer, the electron transport layer, the electron injection layer, and the back electrode 7 are laminated in that order on the back electrode 7 side of the light-emitting layer 4.

The organic electroluminescent device shown in FIG. 11 has a transparent insulator substrate 1, and a transparent electrode 2, a hole transport layer and/or a hole injection layer 3, a light-emitting layer 4, and a back electrode 7 formed thereon in that order, and thus, has a layer structure equivalent to layer structure (3). However, when the layer indicated by reference character 3 is a hole transport layer and a hole injection layer, the hole injection layer, the hole transport layer, and the light-emitting layer 4 are laminated in that order on the back electrode 7 of the transparent electrode 2.

The organic electroluminescent device shown in FIG. 12 has a transparent insulator substrate 1, and a transparent electrode 2, a light-emitting layer having electric charge-transporting ability 6 and a back electrode 7 formed thereon in that order.

Hereinafter, each layer structure will be described in detail.

The charge-transporting polyester according to an aspect of the invention may have hole- or electron-transporting ability depending on the function of the organic compound layer containing the polyester.

For example in the case of the layer structure of the organic electroluminescent device shown in FIG. 9, the charge-transporting polyester may be contained in any one of the light-emitting layer 4 or the electron transport layer 5, and thus, the layer containing the charge-transporting polyester may function either as a light-emitting layer 4 or an electron transport layer 5. In the case of the layer structure of the organic electroluminescent device shown in FIG. 10, the charge-transporting polyester may be contained in any of the hole transport layer 3, the light-emitting layer 4, or the electron transport layer 5, and thus, the layer containing it functions as a hole transport layer 3, a light-emitting layer 4 or an electron transport layer 5. In the case of the layer structure of the organic electroluminescent device shown in FIG. 11, the charge-transporting polyester may be contained in any of the hole transport layer 3 or the light-emitting layer 4, and thus, the layer containing it functions as either as a hole transport layer 3 or a light-emitting layer 4. In the case of the layer structure of the organic electroluminescent device shown in FIG. 12, the charge-transporting polyester is contained in the light-emitting layer having electric charge-transporting ability 6, and thus, the layer containing the charge-transporting polyester functions as a light-emitting layer having electric charge-transporting ability 6.

In the case of the layer structures of the organic electroluminescent devices shown in FIGS. 9 to 12, the transparent insulator substrate 1 may be transparent so as to allow transmission of the emitted light, and examples thereof include, but are not limited to, glass and plastic films. The transparent electrode 2, similarly to the transparent insulator substrate, is preferably transparent so as to allow transmission of the emitted light, and preferably has a greater work function so as to ease hole injection, and examples thereof include, but are not limited to, oxide layers such as of indium tin oxide (ITO), tin oxide (NESA), indium oxide, and zinc oxide, and films formed by vapor deposition or sputtering of gold, platinum, palladium, or the like.

In the case of the layer structures of the organic electroluminescent devices shown in FIGS. 9 and 10, the electron transport layer 5 may be made only of a charge-transporting polyester having a function corresponding to the purpose (electron-transporting ability). As an alternative, the electron transport layer 5 may additionally contain an electron-transporting material other than the charge-transporting polyester in an amount in the range of 1 to 50 wt % dispersed therein so as to adjust the electron mobility for the purpose of further improving the electrical properties. Examples of the electron-transporting material include oxadiazole derivatives, nitro-substituted fluorenone derivatives, diphenoquinone derivatives, thiopyranedioxide derivatives, and fluorenylidenemethane derivatives. Specific examples include, but are not limited to, the following exemplary compounds (VIII-1) to (VIII-3). In addition, it may be used in combination with multiple electron-transporting materials. When the charge-transporting polyester above is not used, the electron transport layer includes only one, or two or more, electron-transporting materials that may be selected from those described above.

(hole-transporting ability). As an alternative, the hole transport layer 3 may additionally contain a hole-transporting material other than the charge-transporting polyester in an amount in the range of 1 to 50 wt % dispersed therein so as to adjust the hole mobility. Examples of the hole-transporting materials include tetraphenylenediamine derivatives, triphenylamine derivatives, carbazole derivatives, stilbene derivatives, arylhydrazone derivatives, and porphyrin compounds, and specific examples thereof include the following exemplary compounds (IX-1) to (IX-9). Among them, tetraphenylenediamine derivatives are preferable because they are superior in compatibility with the charge-transporting polyester. As an alternative, the hole transport layer may include a mixture of the charge-transporting polyester and one or more

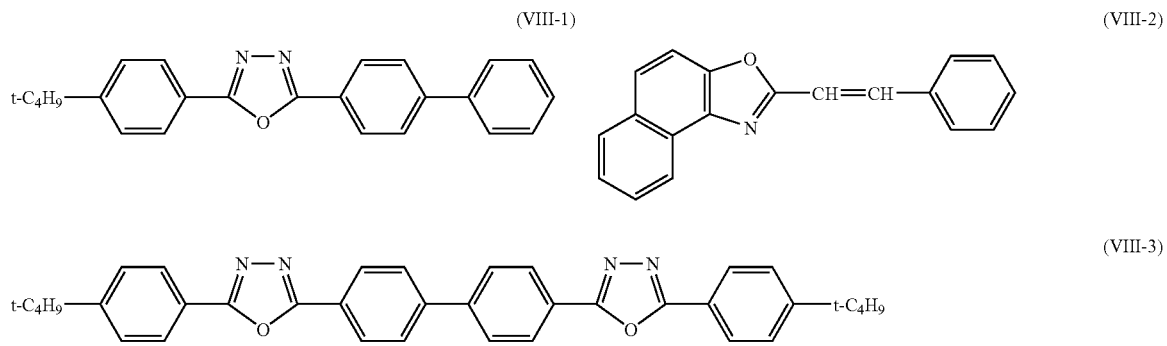

In the case of the layer structures of the organic electroluminescent devices shown in FIG. 10 and FIG. 11, the hole transport layer 3 may be made only of a charge-transporting polyester having a function corresponding to the purpose other common resins. When the charge-transporting polyester above is not used, the hole transport layer includes only one, or two or more, charge-transporting materials that may be selected from those described above.

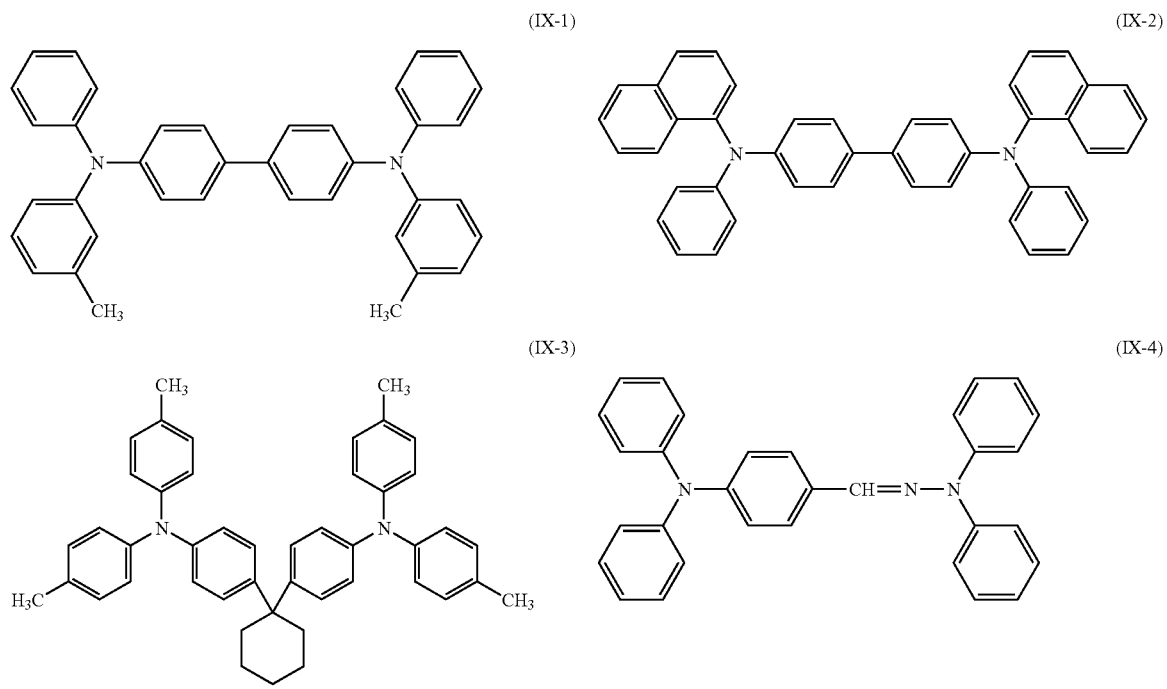

(IX-5)
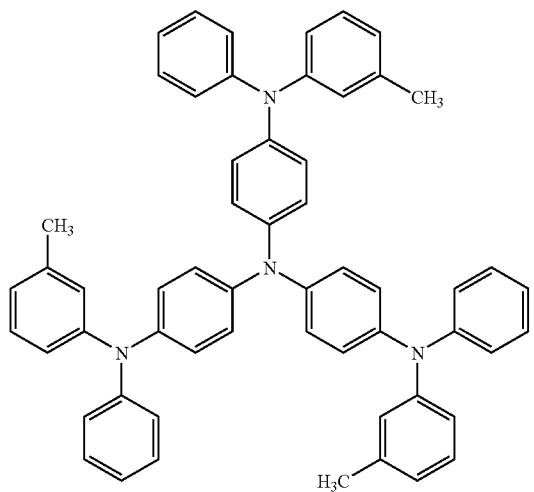
(IX-6)
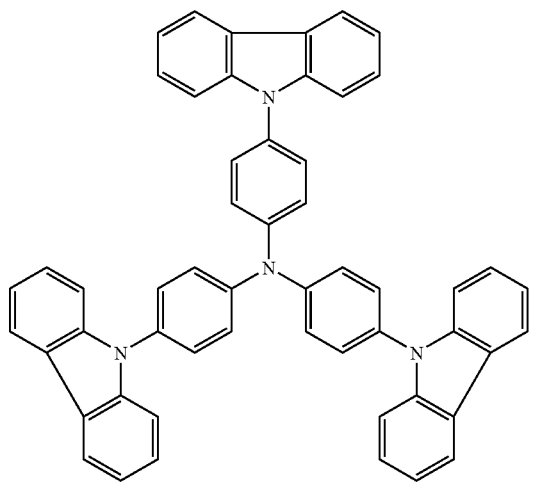
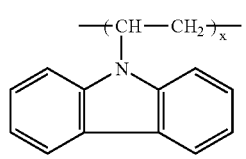
(IX-7)
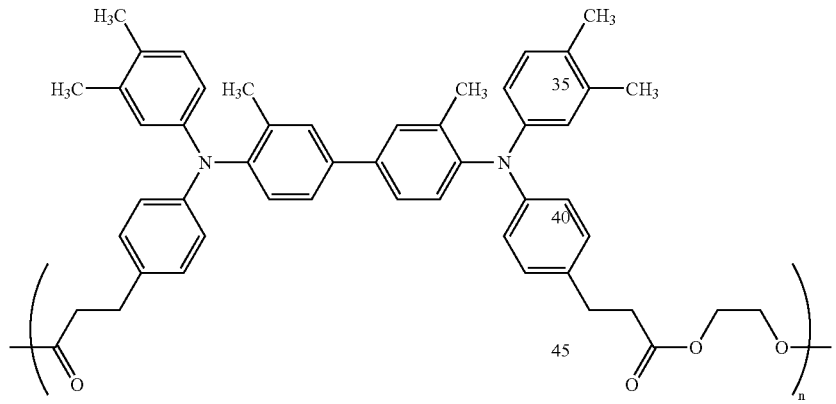
(IX-8)
(IX-9)
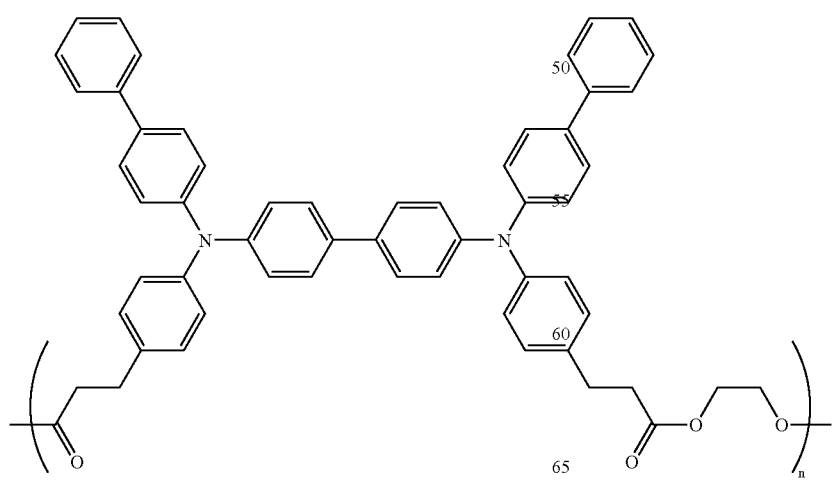

In the case of the layer structures of the organic EL devices shown in FIGS. 9 to 11, a compound having a high fluorescence quantum yield in the solid state is used as the light-emitting material in the light-emitting layer 4. When the light-emitting material is an organic low-molecular weight compound, the compound should give a favorable thin film by vacuum deposition or application and drying of a solution or dispersion liquid containing the low-molecular weight compound and a binder resin. Alternatively when it is a polymer, the polymer should give a favorable thin film by application and drying of a solution or dispersion liquid containing the polymer. Examples of the organic low-molecular weight compound include chelating organic metal complexes, fused polynuclear aromatic ring compounds, perylene derivatives, coumarin derivatives, styrylarylene derivatives, silol derivatives, oxazole derivatives, oxathiazole derivatives, and oxadiazole derivatives, and examples of the polymer include poly-para-phenylene derivatives, poly-para-phenylene vinylene derivatives, polythiophene derivatives, polyacetylene derivatives, and polyfluorene derivatives. Specific examples include, but are not limited to, the following compounds (X-1) to (X-17).

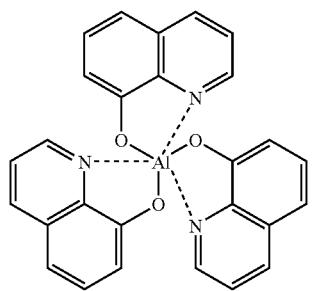
(X-1)

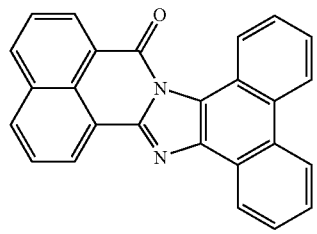
(X-2)

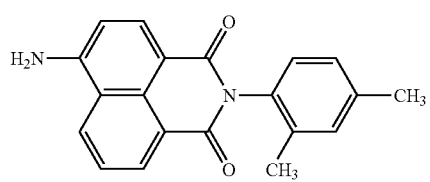
(X-3)

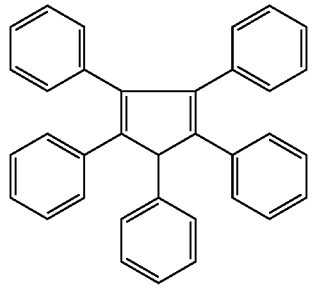
(X-4)

-continued

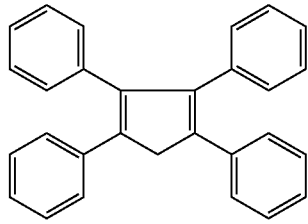
(X-5)

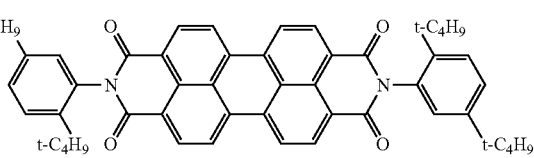
(X-6)

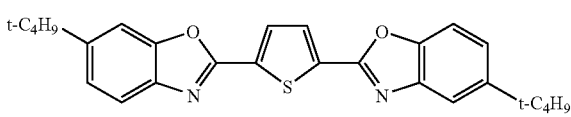
(X-7)

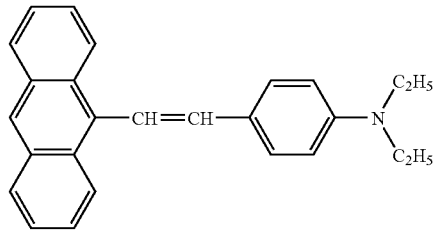
(X-8)

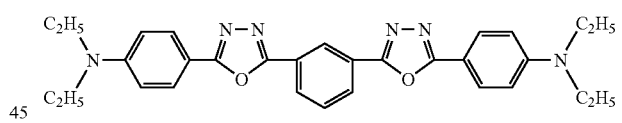
(X-9)

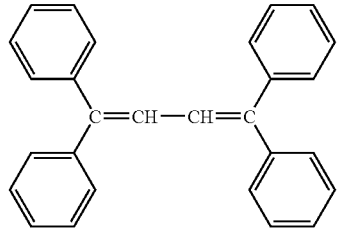
(X-10)

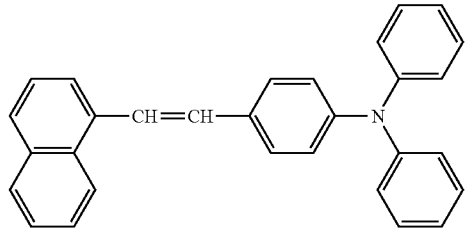
(X-11)

-continued

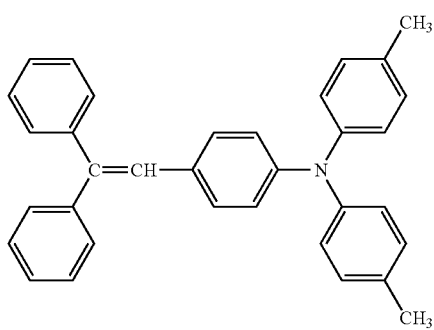
(X-12)

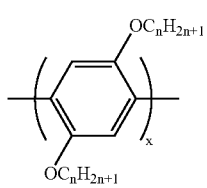
(X-13)

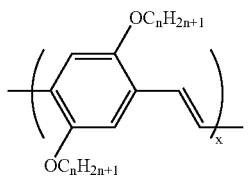
(X-14)

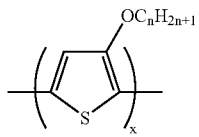
(X-15)

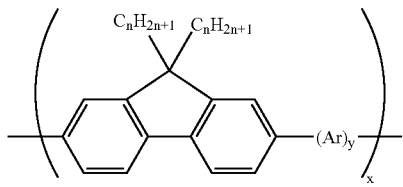
(X-16)

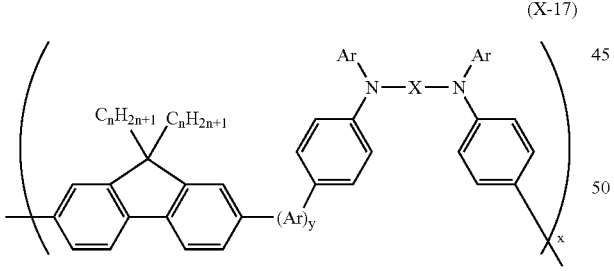
(X-17)

[In structural formulae (X-13) to (X-17), each of n and x is independently an integer of 1 or greater, y is 0 or 1; and in formulae (X-16) and (X-17), Ar represents a substituted or unsubstituted monovalent or bivalent aromatic group, and X represents a substituted or unsubstituted bivalent aromatic group].

A colorant compound as a guest material that is different form the light-emitting material above may be doped to the light-emitting material so as to improve the durability or luminous efficiency of the organic electroluminescent device. The compound is doped by co-vapor deposition when a light-emitting layer is formed by vacuum deposition, or alterna- tively, the compound is mixed in a solution or dispersion liquid to achieve doping when the light-emitting layer is formed by application and drying of the solution or dispersion liquid. The proportion of the colorant compound to be doped in the light-emitting layer may be 0.001 to 40 wt %, preferably 0.01 to 10 wt %. The colorant compound used for doping may be an organic compound superior in compatibility with the light-emitting material that allows formation of a thin light-emitting layer, and examples thereof include DCM derivatives, quinacridone derivatives, rubrene derivatives, and porphyrin compounds. Specific examples include, but are not limited to, the following compounds (XI-1) to (XI-4).

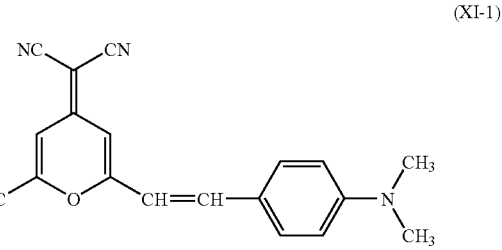
(XI-1)

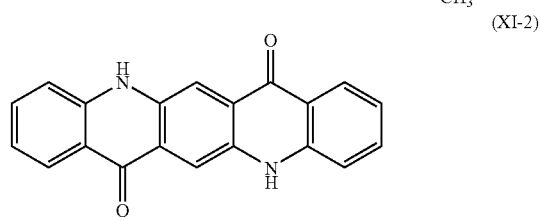
(XI-2)

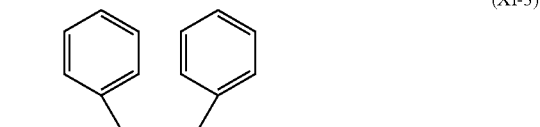
(XI-3)

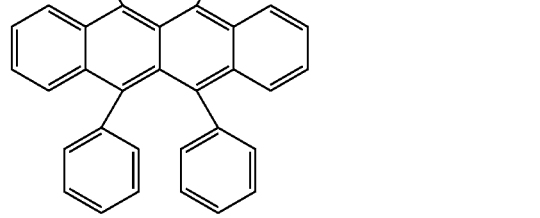
(XI-4)

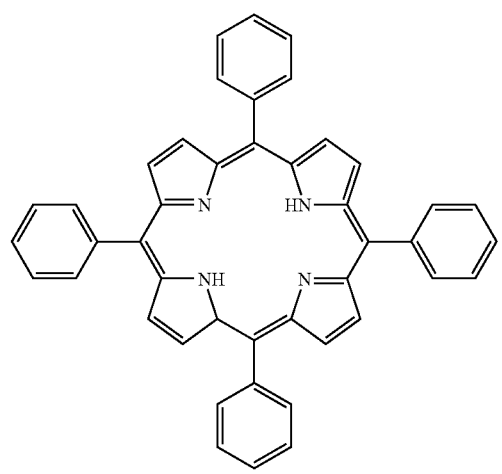

The light-emitting layer 4 may be made only of the light-emitting material above. As an alternative, the light-emitting layer may include 1 to 50 wt % of the charge-transporting polyester above that is dispersed in the light-emitting material so as to further improve the electrical properties and emission characteristics. As another alternative, the light-emitting layer may include 1 to 50 wt % of a charge-transporting material dispersed in the light-emitting material, the charge-transporting material being other than the charge-transporting polyester described above. When the charge-transporting polyester has light-emitting property additionally, it may be used as the light-emitting material, and in such a case, the light-emitting layer may include 1 to 50 wt % of a charge-transporting material dispersed in the light-emitting material so as to further improve the electrical properties and emission characteristics, the charge-transporting material being other than the charge-transporting polyester described above.

In the case of the layer structure of the organic electroluminescent device shown in FIG. 12, the light-emitting layer having electric charge-transporting ability 6 is an organic compound layer formed only with the charge-transporting polyester having a function corresponding to the purpose (hole-transporting ability or electron-transporting ability) or an organic compound layer containing a light-emitting material other than the charge-transporting polyester (preferably, at least one material selected from the light-emitting materials (X-1) to (X-17) in an amount of 50 wt % or less) dispersed in the charge-transporting polyester. Such a light-emitting layer 6 may further include 10 to 50 wt % of a charge-transporting material dispersed therein so as to control the balance between the holes and electrons injected into the organic electroluminescent device, the charge-transporting material being other than the charge-transporting polyester. Examples of the charge-transporting material used as the electron-transporting material for control of electron mobility include oxadiazole derivatives, nitro-substituted fluorenone derivatives, diphenoquinone derivatives, thiopyranedioxide derivatives, and fluorenylidenemethane derivatives. Specific examples thereof include the exemplary compounds (VIII-1) to (VIII-3) shown above.

Use of an organic compound not showing strong interaction with the charge-transporting polyester is preferable; use of the following exemplary compound (XII) is more preferable; but the compound is not limited thereto.

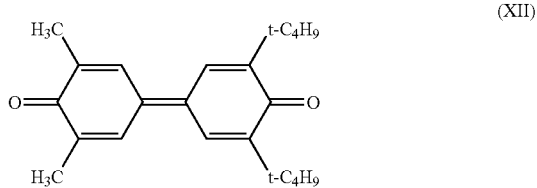

(XII)

Examples of the hole-transporting material usable when the hole mobility is adjusted include tetraphenylenediamine derivatives, triphenylamine derivatives, carbazole derivatives, stilbene derivatives, arylhydrazone derivatives, and porphyrin compounds; specific examples include the exemplary compounds (IX-1) to (IX-9) shown above. Tetraphenylenediamine derivatives, which are superior in compatibility with the charge-transporting polyester, are preferable.

In the case of the layer structures of the organic electroluminescent devices shown in FIGS. 9 to 12, a metal allowing vacuum deposition and having a small work function permitting electron injection is generally used for the back electrode 7, and examples thereof include magnesium, aluminum, silver, indium and alloys thereof, and metal halides and metal oxides such as lithium fluoride and lithium oxide. A protective layer may be formed additionally on the back electrode 7 so as to prevent deterioration of the device due to water and oxygen. Specific examples of the material for the protective layer include metals such as In, Sn, Pb, Au, Cu, Ag, and Al; metal oxides such as MgO, $SiO_2$, and $TiO_2$; and resins such as polyethylene resin, polyurea resin, and polyimide resin. Vacuum deposition, sputtering, plasma polymerization, CVD, or coating may be used in forming the protective layer.

Each of these organic electroluminescent devices shown in FIGS. 9 to 12 can be prepared first by forming the respective layers on a transparent electrode 2 in the order according to the layer structure of the organic electroluminescent device. The hole transport layer and/or hole injection layer 3, light-emitting layer 4, electron transport layer and/or electron injection layer 5, or light-emitting layer having electric charge-transporting ability 6 is formed on the transparent electrode, for example, by vacuum deposition of the materials described above or by dissolving or dispersing the materials in an appropriate solvent to form a coating liquid, and providing the coating liquid on the transparent electrode by spin coating, casting, dipping, or inkjet. Among the methods above, inkjet method is preferable because it allows application of only a required amount of polymer material on the positions of desired pixels, reduces undesirable consumption of the materials, and is thus, friendly to global environment, allows high-definition patterning and easy expansion in size of the layer, and provides a greater degree of freedom of the medium on which the printing is conducted on.

The thickness of each of the hole transport layer and/or hole injection layer 3, light-emitting layer 4, electron transport layer and/or electron injection layer 5, and the thickness of the light-emitting layer having electric charge-transporting ability 6 is preferably in the range of 10 μm or less, more preferably 0.001 to 5 μm. The dispersion state of respective materials above (e.g., non-conjugated polymer, light-emitting material, etc.) may be molecular dispersion state or fine-particle state containing fine crystals. The dispersion solvent to be used in the film-forming method using a coating solution may be selected appropriately according to the dispersibility and solubility of the respective materials so as to realize the molecular dispersion state. A ball mill, a sand mill, a paint shaker, an attriter, a homogenizer, ultrasonic wave, or the like can be used for dispersing the materials to the fine particle state.

In the case of the organic electroluminescent devices shown in FIGS. 9 and 10, the organic electroluminescent device according to an aspect of the invention can be prepared by forming a back electrode 7 on the electron transport layer and/or the electron injection layer 5, for example, by vacuum deposition or sputtering. The organic electroluminescent device according to an aspect of the invention can be prepared by forming a back electrode 7, for example by vacuum deposition or sputtering on the light-emitting layer 4 in the case of the organic electroluminescent device shown in FIG. 11 and on the light-emitting layer having electric charge-transporting ability 6 in the case of the organic electroluminescent device shown in FIG. 11.

Light is emitted from the organic electroluminescent device according an aspect of the invention, when, for example, a DC voltage of 4 to 20 V at a current density of 1 to 200 mA/cm² is applied between the pair of electrodes.

—Image Display Medium—

The image display medium in which the organic electroluminescent device according to an aspect of the invention is used will be described below.

The organic electroluminescent devices according to an aspect of the invention may be arranged in a matrix and/or segment shape to form an image display medium. In arranging the organic electroluminescent devices in the matrix shape, only electrodes may be disposed in the matrix shape, or both electrodes and organic compound layers may be disposed in the matrix shape. When arranging the organic electroluminescent devices in the segment shape, only electrodes may be disposed in the segment shape, or both electrodes and organic compound layers may be disposed in the segment shape.

The organic compound layers disposed in the matrix or segment shape can be prepared easily by the inkjet printing method above.

EXAMPLES

Hereinafter, the present invention will be described with reference to Examples, but it should be understood that the invention is not limited thereto. "Part" and "%" in the following Examples are based on weight (i.e., part by weight and % by weight).

Example 1

Acetanilide (25.0 g), methyl 4-iodophenylpropionate (64.4 g), potassium carbonate (38.3 g), copper sulfate pentahydrate (2.3 g), and n-tridecane (50 ml) are placed in a 500-ml three-necked flask, and the mixture is stirred under heat and nitrogen stream at 230° C. for 20 hours. After reaction, a solution of potassium hydroxide (15.6 g) in ethylene glycol (300 ml) is added thereto; the mixture is heated under reflux under nitrogen stream for 3.5 hours, and cooled to room temperature; and the reaction solution is poured into 1 L of distilled water and neutralized with hydrochloric acid, to give a crystalline precipitate. The crystal is collected by suction filtration, washed thoroughly with water, and transferred into a 1-L flask. Toluene (500 ml) is added thereto; the mixture is heated under reflux, while water is removed by azeotropic distillation; a solution of conc. sulfturic acid (1.5 ml) in methanol (300 ml) is added; and the mixture is heated under reflux under nitrogen stream for 5 hours. After reaction, the product is extracted with toluene, and the organic layer is washed with water thoroughly. Then after drying over anhydrous sodium sulfate, the solvent is removed under reduced pressure, and the residue is recrystallized from hexane, to give 36.5 g of DAA-1.

DAA-1

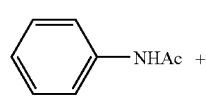

NHAc +

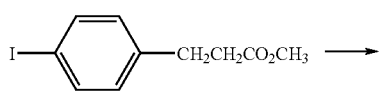

-continued

Tetrakis(triphenyl)phosphine palladium (0.4 g), toluene (15 ml), 2,7-diiodo-9,9-dimethylfluorene (5 g), sodium hydrogen carbonate aqueous solution (6 ml), 5-chlorothiophene-2-boronic acid (2 g), and ethanol (5 ml) are placed in a 100-ml three-necked round-bottomed flask, and the mixture is heated under reflux in a nitrogen environment for 4 hours. After reaction, the mixture is allowed to cool to room temperature; the aqueous and organic layers are separated; and the organic layer is washed with saturated aqueous sodium chloride solution. The solvent is removed under reduced pressure, to give a crude product. The residue is purified by silica gel chromatography using hexane, to give 1.1 g of [intermediate 1].

[Intermediate 1]

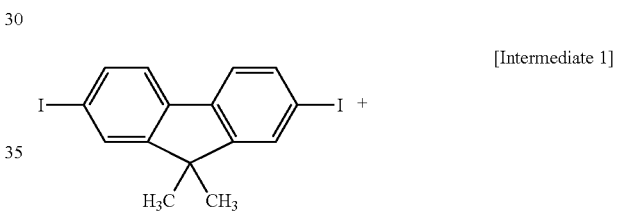

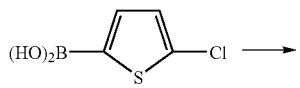

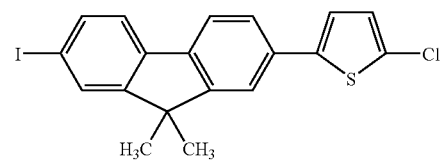

DAA-1 (0.8 g), [intermediate 1] (1.1 g), potassium carbonate (0.6 g), copper sulfate pentahydrate (0.1 g), and o-dichlorobenzene (2 ml) are placed in a 25-ml three-necked flask, and the mixture is stirred under heat and under nitrogen stream at 180° C. for 15 hours. After reaction, the mixture is allowed to cool to 100° C. and dissolved in toluene; the insoluble matter is removed by Celite filtration while hot; and the filtrate is purified by silica gel column chromatography using ethyl acetate/hexane, to give 1.1 g of TAA-1.

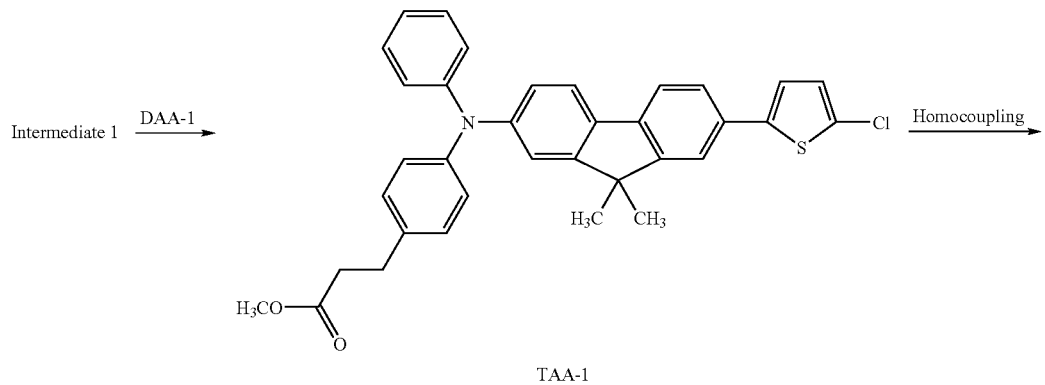

TAA-1

Figure 2:
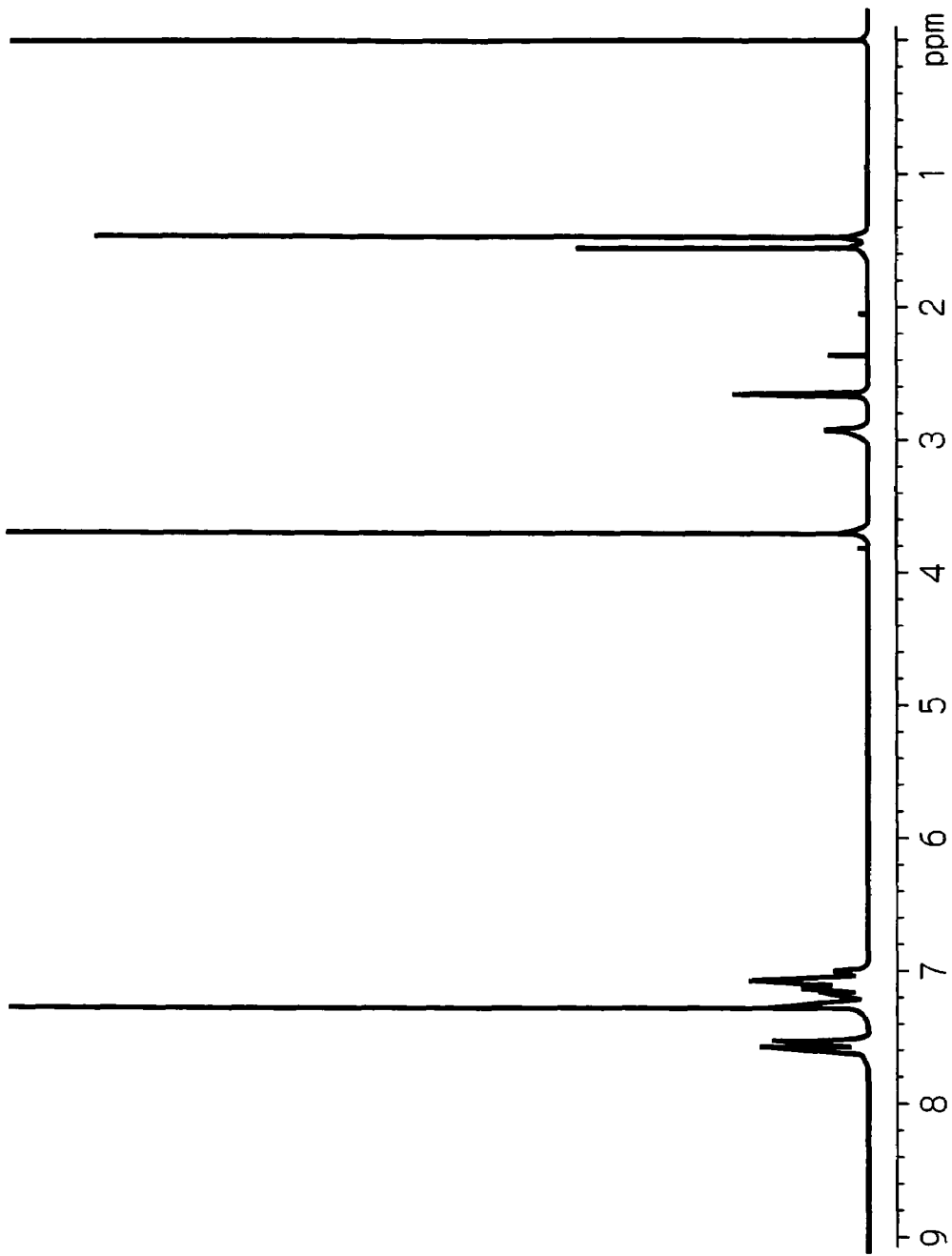
FIG. 2 is the NMR spectrum of the compound obtained in Example 1.

Nickel chloride (0.3 g), triphenylphosphine (2.1 g), and anhydrous DMF (4 ml) are placed in a 25-ml three-necked flask; the mixture is heated to 50° C.; and after addition of zinc (0.1 g), the mixture is stirred at 50° C. for 1 hour. TAA-1 (1.0 g) and anhydrous DMF (3 ml) are added then, and the mixture is stirred additionally for 2.5 hours. After termination of the reaction, the mixture is poured into water (80 ml); the aqueous and organic layers are separated; the organic layer is washed and, after drying over anhydrous sodium sulfate, the solvent is removed under reduced pressure, to give a crude product. The product is purified by silica gel column chromatography using ethyl acetate/hexane, to give 0.6 g of an exemplary compound 5 (yield: 66%). The melting point of the exemplary compound 5 thus obtained is 223 to 225° C. The infrared absorption spectrum of the exemplary compound 5 obtained is shown in FIG. 1, and the NMR spectrum (1H-NMR, solvent: CDCl₃, the same shall apply in NMR spectra below) in FIG. 2.

Example 2

The intermediate 1 (4.0 g), methyl 4-acetamidophenylpropionate (26.9 g), potassium carbonate (3.7 g), copper sulfate pentahydrate (0.4 g), and o-dichlorobenzene (20 ml) are placed in a 100-ml three-necked flask, and the mixture is stirred under heat and nitrogen stream at 185° C. for 13.5 hours. After termination of the reaction, a solution of potassium hydroxide (1.3 g) in ethylene glycol (25 ml) is added, and the mixture is heated under reflux under nitrogen stream for 5 hours. After termination of the reaction, the mixture is allowed to cool to room temperature, and, after being added to distilled water (200 ml), is neutralized with hydrochloric acid, to give a crystalline precipitate. The crystal is collected by filtration, washed thoroughly with water, and transferred into a 1-L flask. Toluene (300 ml) is added thereto; the mixture is heated under reflux to remove water by azeotropic distillation; then methanol (100 ml) and conc. sulfuric acid (0.5 ml) are added thereto; and the mixture is heated under reflux under nitrogen stream for 4.5 hours. After termination of the reaction, the reaction product is poured into distilled water and extracted with toluene. The organic layer is washed thoroughly with distilled water and dried over anhydrous sodium sulfate; the solvent is removed under reduced pressure; and the residue is recrystallized from an ethyl acetate/hexane liquid mixture, to give 2.8 g of DAA-2.

An intermediate 2 is prepared in a similar manner to the preparation of intermediate 1, except that 5-chlorothiophene-2-boronic acid is replaced with thiophene-2-boronic acid.

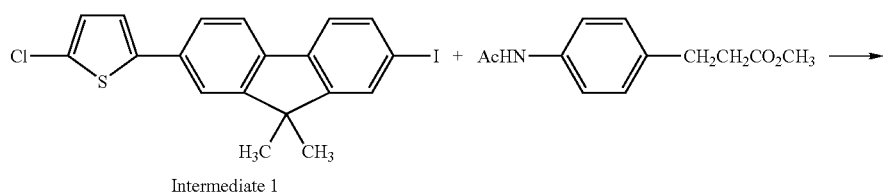

Intermediate 1

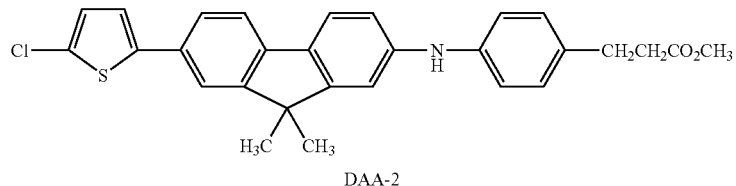

DAA-2

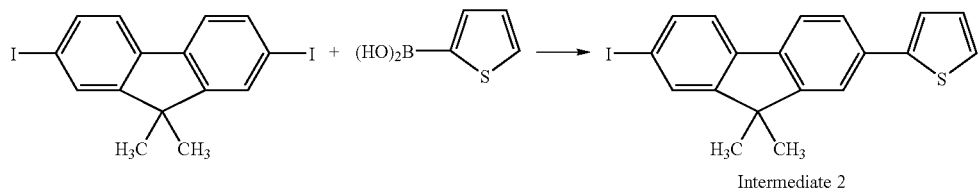

Intermediate 2

DAA-2 (1.1 g), the intermediate 2 (1.4 g), potassium carbonate (0.7 g), copper sulfate pentahydrate (0.1 g), and o-dichlorobenzene (2 ml) are placed in a 50-ml three-necked flask, and the mixture is stirred under heat and nitrogen stream at 180° C. for 12 hours. After termination of the reaction, the mixture is allowed to cool to 100° C. and dissolved in 100 ml of toluene; the insoluble matter is removed by Celite filtration while hot; and the filtrate is purified by silica gel column chromatography using toluene, to give 1.7 g of TAA-2.

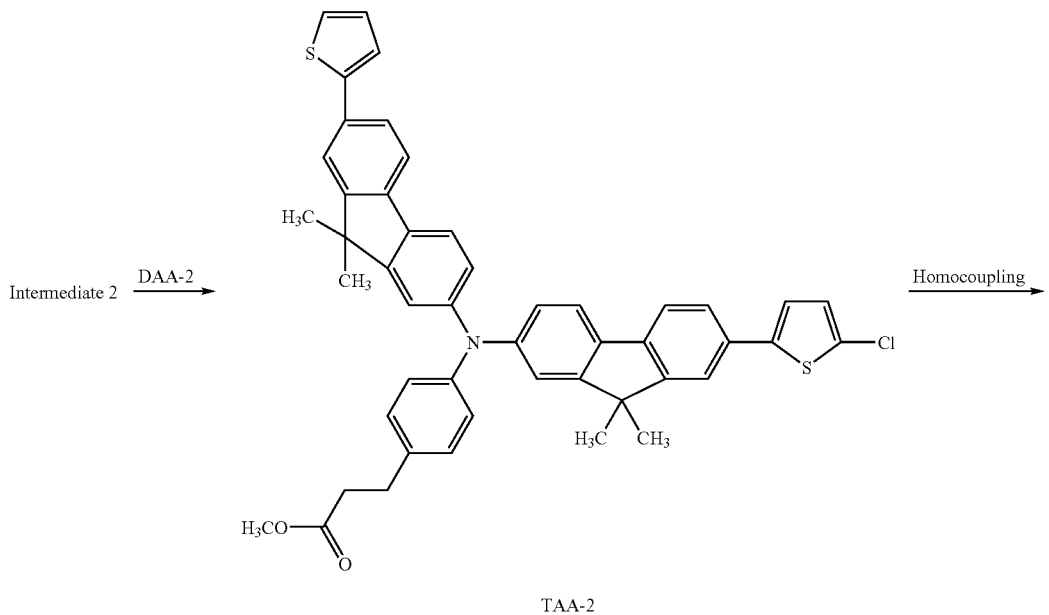

TAA-2

Figure 3:
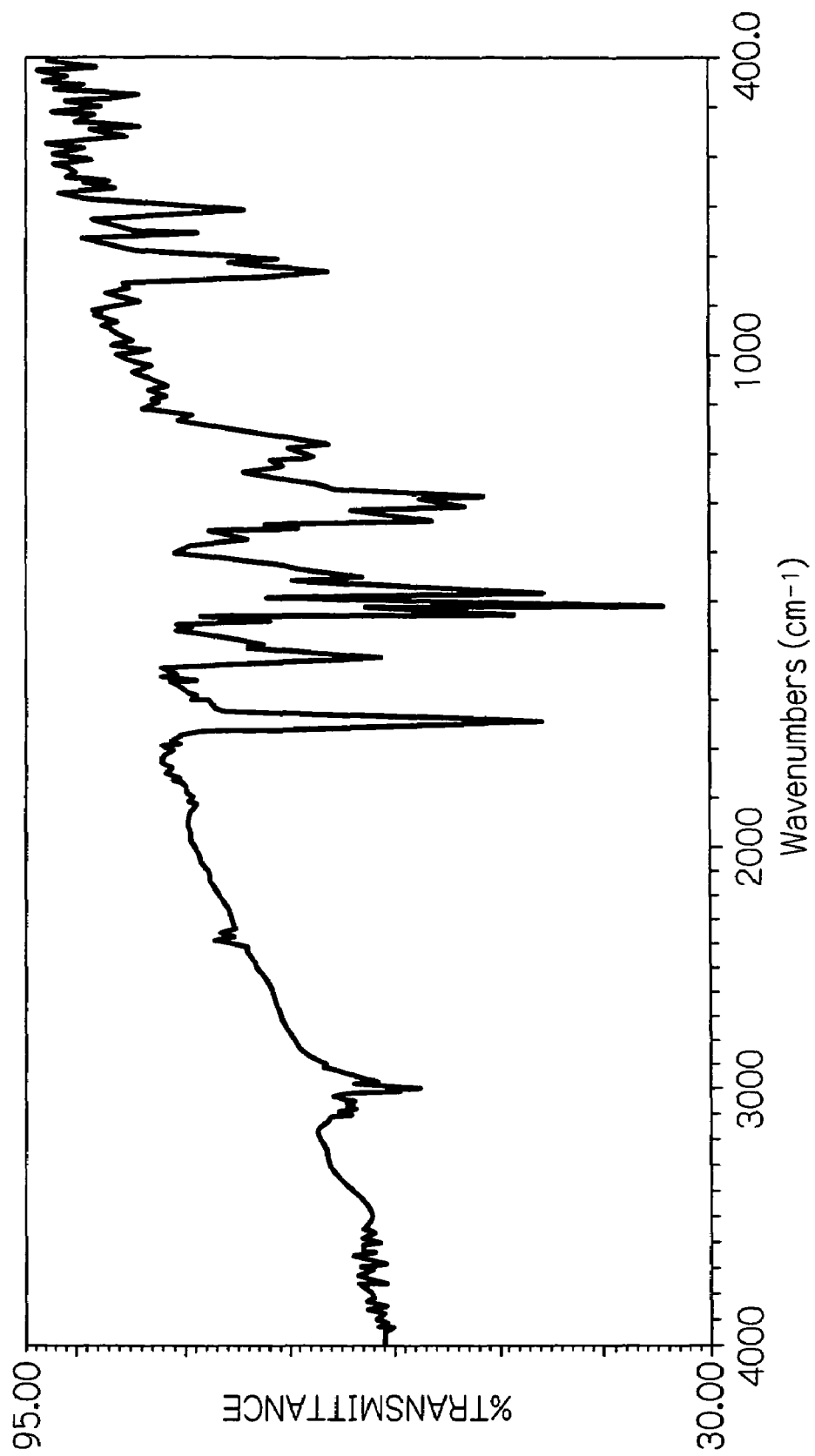
FIG. 3 is the IR spectrum of the compound obtained in Example 2.
Figure 4:
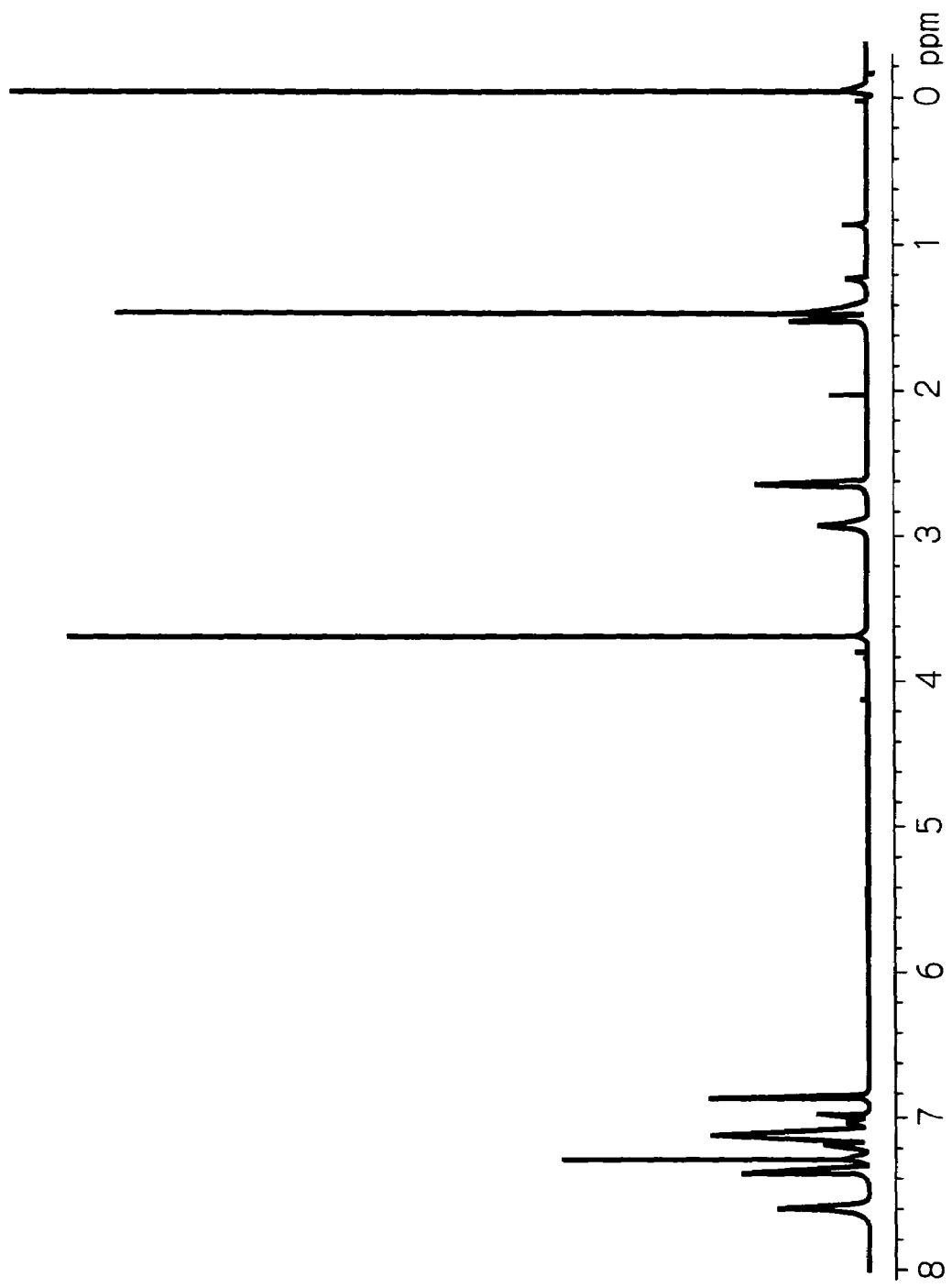
FIG. 4 is the NMR spectrum of the compound obtained in Example 2.

Nickel chloride (0.2 g), triphenylphosphine (1.4 g), and anhydrous DMF (5 ml) are placed in a 25-ml three-necked flask, and the mixture is heated to 50° C. and, after addition of zinc (0.1 g), stirred at 50° C. for 1 hour. TAA-2 (0.7 g) is then added, and the mixture is stirred additionally for 2.5 hours. After termination of the reaction, the reaction product is poured into water (50 ml), and the precipitated solid is collected by suction filtration, to give a crude product. The crude product is purified by silica gel column chromatography using an ethyl acetate/hexane/toluene mixture solution, to give 0.6 g of an exemplary compound 22 (yield: 90%). The melting point of the exemplary compound 22 obtained is 176 to 180° C. The infrared absorption spectrum of the exemplary compound 22 obtained is shown in FIG. 3, and the NMR spectrum thereof is shown in FIG. 4.

Example 3

Magnesium (0.2 g) is placed in a 50-ml three-necked flask, baked with a burner, and cooled to room temperature. Ether (2 ml), 5-chloro-2-iodo-3-(2,4-dimethylphenyl)thiophene (3.1 g), and ether (8 ml) are added thereto, and the mixture is heated under reflux for 15 minutes. After confirmation of consumption of magnesium, the mixture is cooled to room temperature, to give a Grignard reagent. Separately, Pd (dppf) Cl$_2$ (0.1 g), 2,7-diiodo-9,9-dimethylfluorene (3.6 g), and toluene (20 ml) are placed in a 100-ml three-necked flask, and the Grignard reagent is added thereto dropwise. After dropwise addition, the mixture is stirred at room temperature for 6 hours. After termination of the reaction, the mixture is made acidic by addition of hydrochloric acid and separated into aqueous and organic layers. The organic layer is washed with distilled water and dried over anhydrous sodium sulfate. The solvent is removed under reduced pressure, to give a crude product. The crude product is purified by silica gel chromatography using hexane, to give 1.1 g of an intermediate 3.

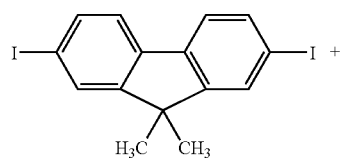

-continued

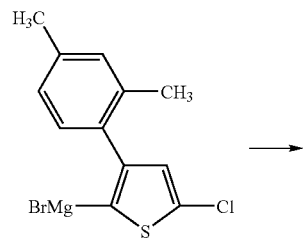

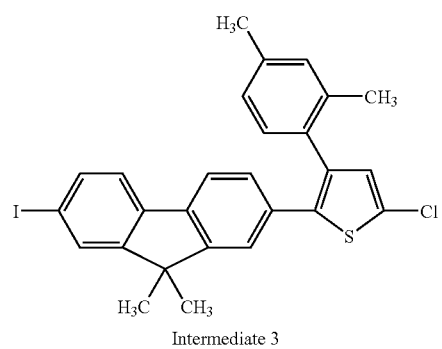

Intermediate 3

2-Hexyl-5-(2-iodo-9,9-dimethylfluorenyl)thiophene (2.2 g), acetamidophenylpropionic methyl ester (0.9 g), potassium carbonate (0.9 g), and copper sulfate pentahydrate (0.1 g), and o-dichlorobenzene (3 ml) are placed in a 50-ml three-necked flask, and the mixture is heated under reflux under nitrogen stream for 16 hours. After termination of the reaction, the mixture is allowed to cool to room temperature and dissolved in 100 ml of toluene; the insoluble matter is removed by filtration; and the filtrate is purified by silica gel column chromatography using an ethyl acetate/hexane liquid mixture, to give 1.9 g of DAA-3.

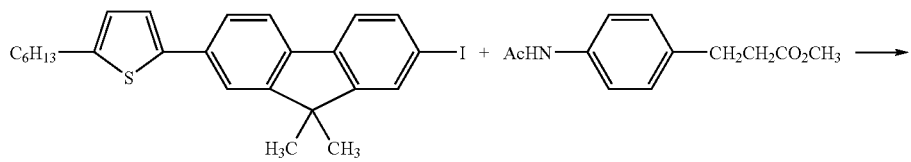

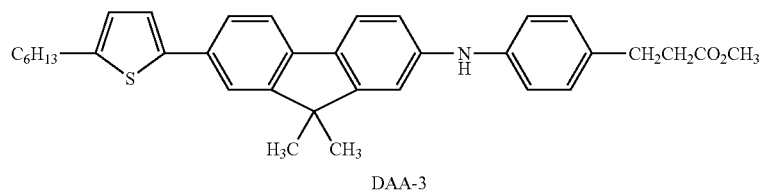

DAA-3

DAA-3 (0.9 g), the intermediate 3 (1.1 g), potassium carbonate (0.4 g), copper sulfate pentahydrate (0.1 g), and o-dichlorobenzene (3 ml) are placed in a 50-ml three-necked flask, and the mixture is heated under reflux under nitrogen stream at 180° C. for 24 hours. After termination of the reaction, the mixture is cooled to 100° C. and dissolved in 100 ml of toluene; the insoluble matter is removed by Celite filtration while hot; and the filtrate is purified by silica gel column chromatography using an ethyl acetate/hexane liquid mixture, to give 1.2 g of TAA-3.

5 hours while ethylene glycol is distilled off. The mixture is then cooled to room temperature and dissolved in 50 ml of monochlorobenzene; the insoluble matter is removed by filtration through a 0.5-μm polytetrafluoroethylene (PTFE) filter; and the filtrate is added dropwise into 500 ml of stirred methanol, to give a polymer precipitate. The polymer obtained is collected by filtration, washed thoroughly with methanol, and dried, to give 0.7 g of a polymer [exemplary compound: (1)]. Analysis of the molecular weight of the polymer by gel-permeation chromatography (GPC) (HLC-

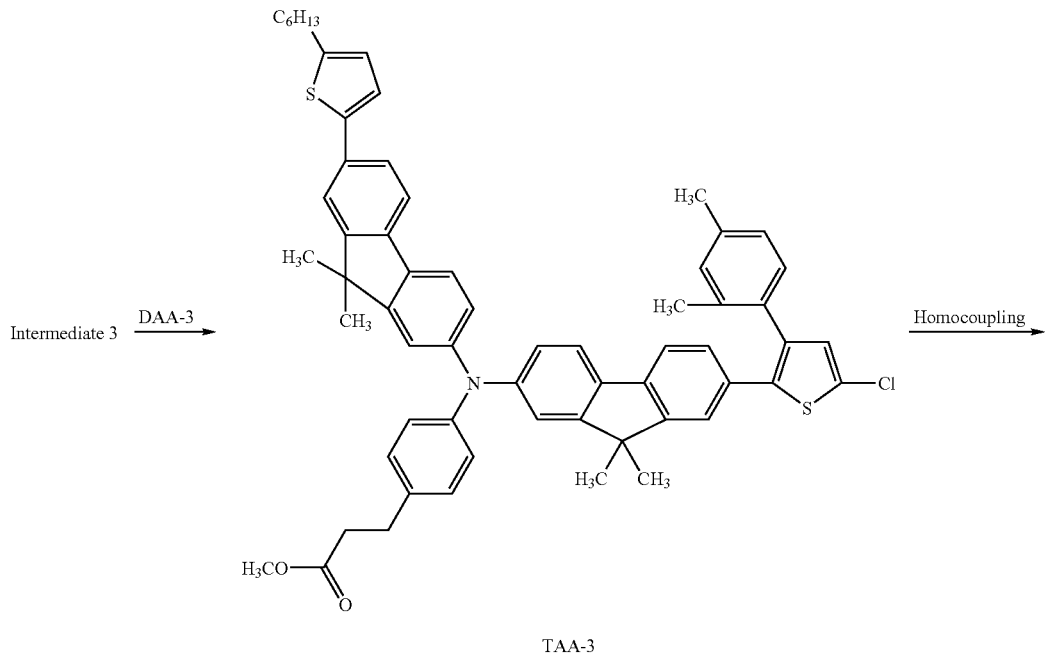

Figure 5:
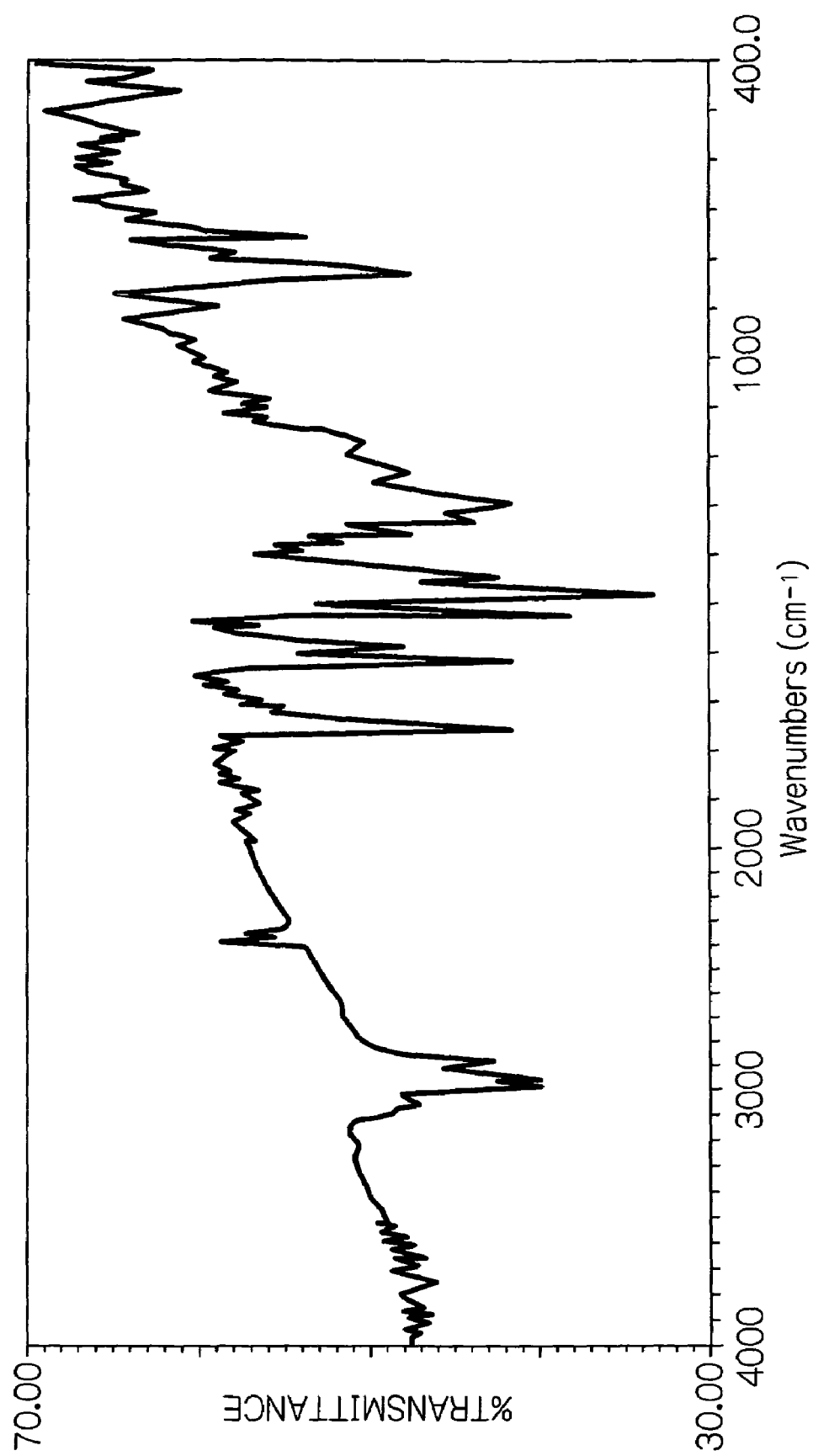
FIG. 5 is the IR spectrum of the compound obtained in Example 3.
Figure 6:
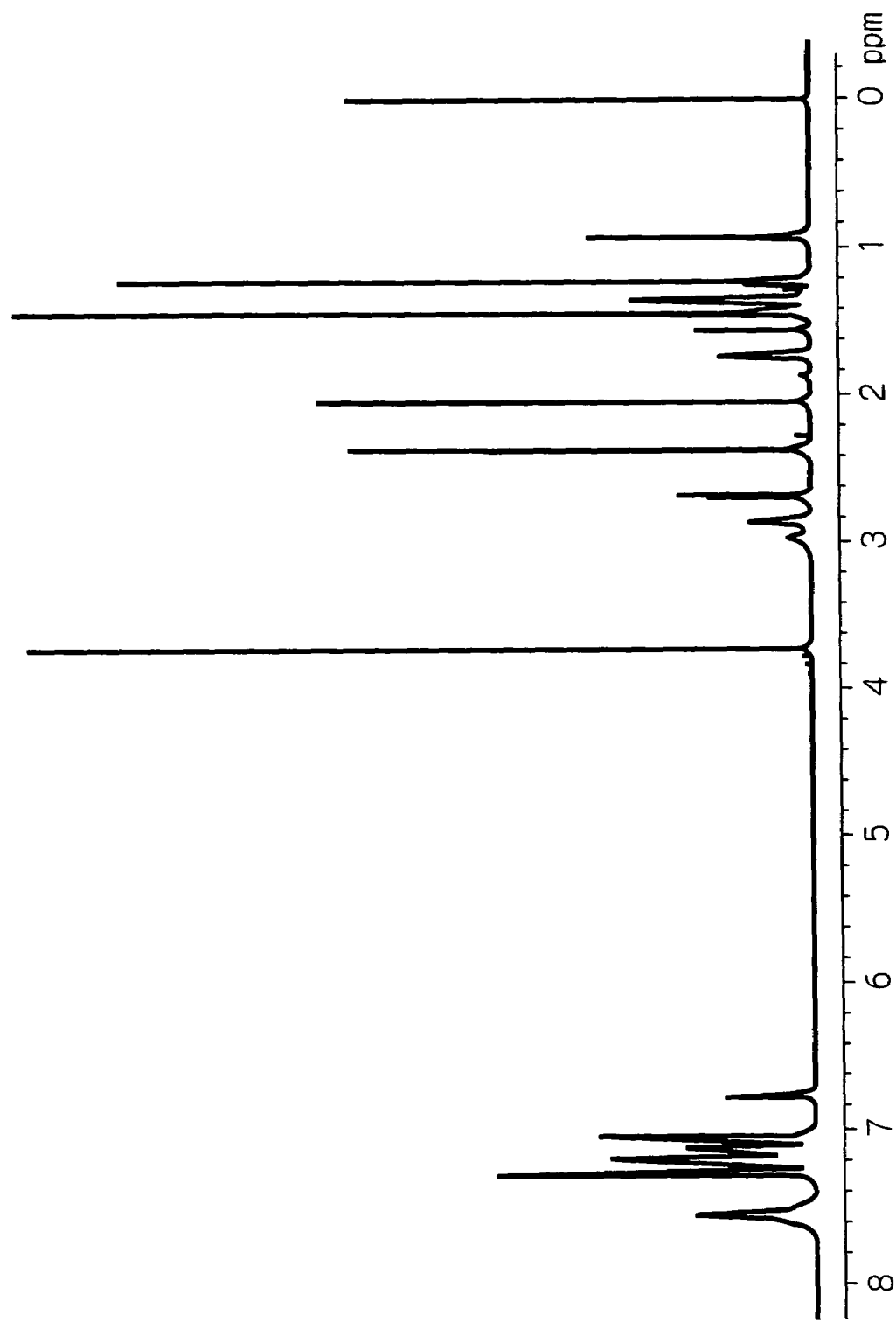
FIG. 6 is the NMR spectrum of the compound obtained in Example 3.

Nickel chloride (0.2 g), triphenylphosphine (1.1 g), and anhydrous DMF (5 ml) are placed in a 25-ml three-necked flask, and the mixture is heated to 50° C. and, after addition of zinc (0.1 g), stirred at 50° C. for 1 hour. TAA-3 (0.7 g) is then added, and the mixture is stirred additionally for 2.5 hours. After termination of the reaction, the reaction product is poured into water (50 ml), and the precipitated solid is collected by suction filtration, to give a crude product. The crude product is purified by silica gel column chromatography using an ethyl acetate/hexane mixture solution, to give 0.6 g of an exemplary compound 23 (yield: 85%). The melting point of the exemplary compound 23 obtained is indefinite. The infrared absorption spectrum of the exemplary compound 23 obtained is shown in FIG. 5, and the NMR spectrum thereof is shown in FIG. 6.

Example 4

Figure 7:
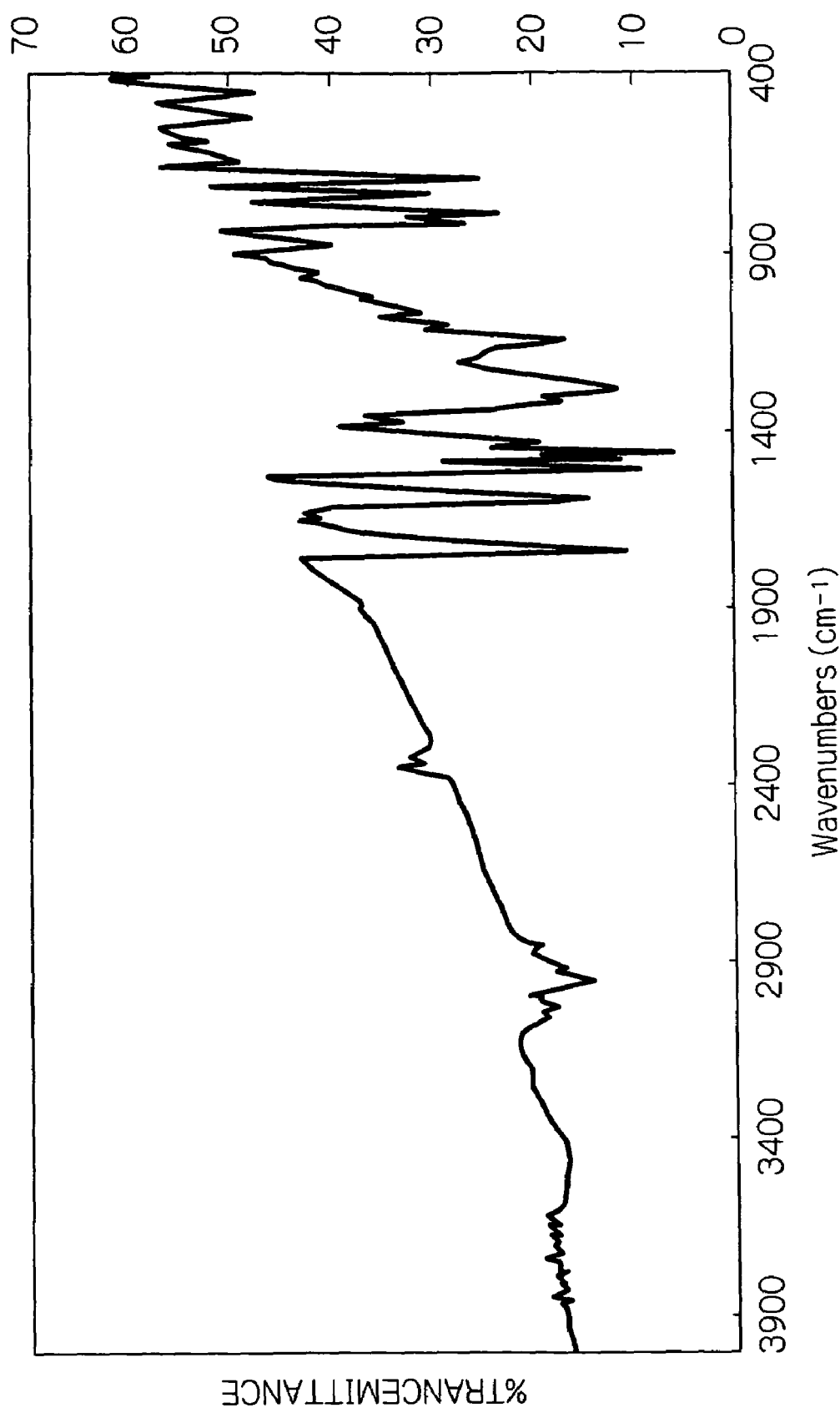
FIG. 7 is the IR spectrum of the compound obtained in Example 4.
Figure 8:
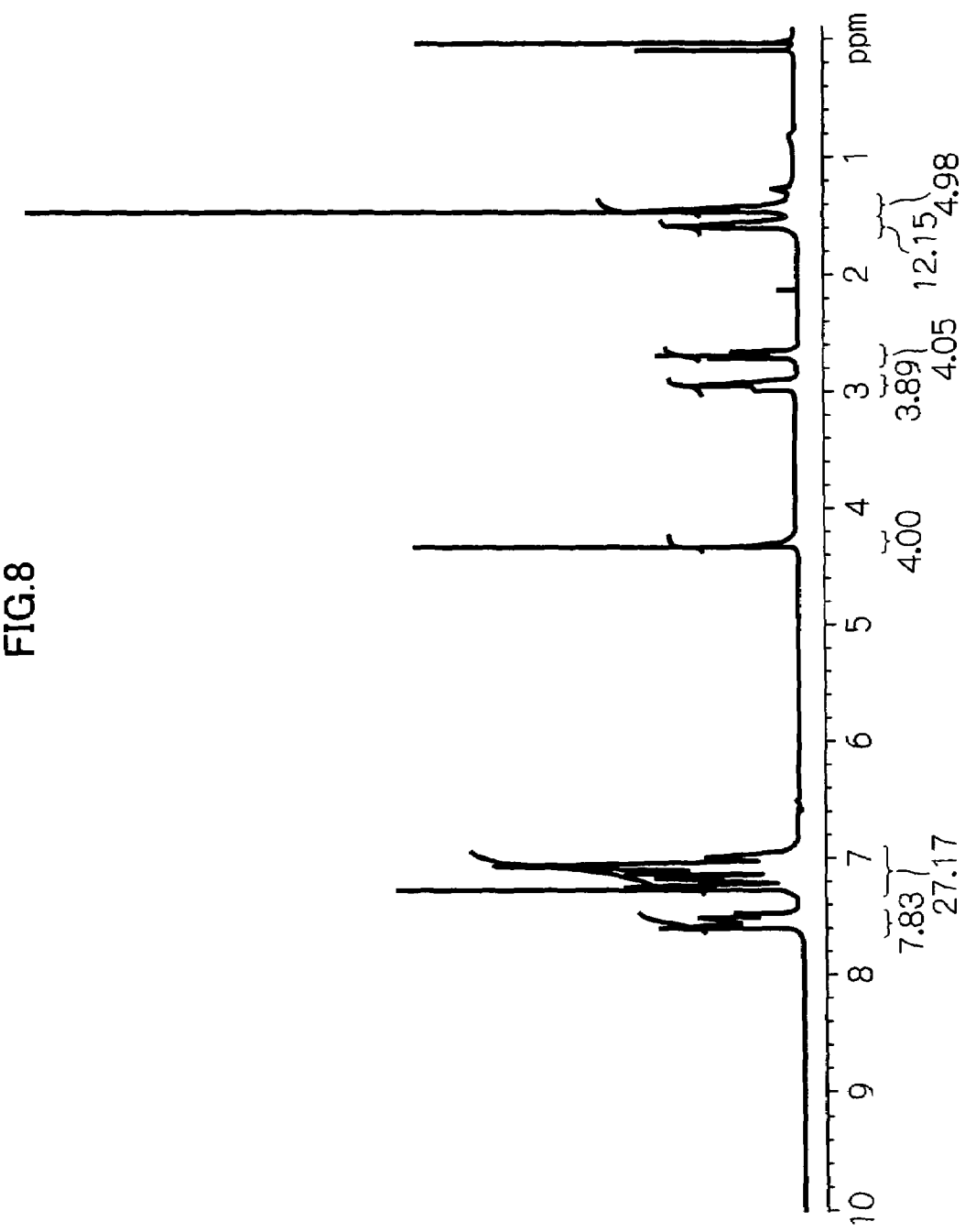
FIG. 8 is the NMR spectrum of the compound obtained in Example 4.

1.0 g of the exemplary compound 5 obtained in Example 1, 5.0 ml of ethylene glycol and 0.02 g of tetrabutoxytitanium are placed in a 50-ml three-necked round-bottomed flask, and, the mixture is stirred under heat and nitrogen stream at 205° C. for 5 hours. After confirmation of consumption of the raw material diamine by TLC, the mixture is heated to 210° C. under a reduce pressure of 0.5 mm Hg and allowed to react for 8120GPC, manufactured by Toso Corporation) showed a MW of $1.83 \times 10^5$ (in terms of styrene) and a Mw/Mn of 3.51, and the polymerization degree p as determined from the monomer molecular weight is approximately 173. The infrared absorption spectrum of the exemplary compound (1) obtained is shown in FIG. 7 and the NMR spectrum thereof is shown in FIG. 8.

Example 5

1.0 g of the exemplary compound 22 obtained in Example 2, 8.0 ml of ethylene glycol and 0.02 g of tetrabutoxytitanium are placed in a 50-ml three-necked round-bottomed flask, and the mixture is stirred under heat and nitrogen stream at 200° C. for 7 hours. After confirmation of consumption of the raw material diamine by TLC, the pressure is reduced to 0.5 mmHg, and the mixture is heated to 210° C. and allowed to react for 5 hours while ethylene glycol is distilled off. The mixture is then cooled to room temperature and dissolved in 50 ml of monochlorobenzene; the insoluble matter is removed by filtration through a 0.5-μm PTFE filter; and the filtrate is added dropwise into 500 ml of stirred methanol, to give a polymer precipitate. The polymer obtained is collected by filtration, washed thoroughly with methanol, and dried, to give 0.9 g of a polymer [exemplary compound: (14)]. Analy-

Example 6

0.8 g of the exemplary compound 23 obtained in Example 3, 8.0 ml of ethylene glycol and 0.02 g of tetrabutoxytitanium are placed in a 50-ml three-necked round-bottomed flask, and the mixture is heated under heat and nitrogen stream at 200° C. for 8 hours. After confirmation of consumption of the raw material diamine, the pressure is reduced to 0.5 mmHg, and the mixture is heated to 200° C. and allowed to react for 4 hours while ethylene glycol is distilled off. The mixture is then cooled to room temperature and dissolved in 50 ml of monochlorobenzene; the insoluble matter is removed by filtration through a 0.5-μm PTFE filter; and the filtrate is added dropwise into 500 ml of stirred methanol, to give a polymer precipitate. The polymer obtained is collected by filtration, washed thoroughly with methanol, and dried, to give 0.9 g of a polymer [exemplary compound: (17)]. Analysis of the molecular weight of the polymer by GPC showed a Mw of $1.04 \times 10^5$ (in terms of styrene) and a Mw/Mn of 4.34, and the polymerization degree p as determined from the monomer molecular weight is approximately 64.

Example 7

0.5 g of the exemplary compound 5 obtained in Example 1, 0.5 g of terephthalic acid, 5.0 ml of ethylene glycol and 0.02 g of tetrabutoxytitanium are placed in a 50-ml three-necked round-bottomed flask, and the mixture is stirred under heat and nitrogen stream at 200° C. for 5 hours. After confirmation of consumption of the raw material diamine by TLC, the pressure is reduced to 0.5 mmHg, and the mixture is heated to 200° C. and allowed to react for 7 hours while ethylene glycol is distilled off. The mixture is then cooled to room temperature and dissolved in 50 ml of monochlorobenzene; the insoluble matter is removed by filtration through a 0.5-μm PTFE filter; and the filtrate is added dropwise into 500 ml of stirred methanol, to give a polymer precipitate. The polymer obtained is collected by filtration, washed thoroughly with methanol, and dried, to give 0.9 g of a polymer [exemplary compound: (4)]. Analysis of the molecular weight of the polymer by GPC showed a Mw of $1.22 \times 10^5$ (in terms of styrene) and a Mw/Mn of 3.16, and the polymerization degree p as determined from the monomer molecular weight is approximately 95.

Comparative Example 1

MEH-PPV ((Poly[2-methoxy-5-(2'-ethylhexyloxy)-1,4-phenylenevinylene] (weight-average molecular weight: 86,000)) is prepared and used as a Comparative Example for comparison with the thiophene-containing compounds and thiophene-containing compound polymers thus obtained in Examples according to an aspect of the invention.

The mobility of the thiophene-containing compounds or thiophene-containing compound polymers obtained in Examples 1 to 7 according to an aspect of the invention, and the mobility of the sample of Comparative Example 1 is determined by a time-of-flight method (TOF-401, manufactured by Optel), and the glass transition temperature thereof is measured by differential scanning calorimetry (DSC) (Tg/DTA6200, manufactured by Seiko Instruments Inc.). The mobility measurement is conducted on a film in which 40 wt % (20 wt %, only in Example 2) of the sample is dispersed in polycarbonate when the sample is a monomer. When the sample is a polymer, the mobility measurement is conducted on a film obtained from the sample dissolved in a solvent. The absorption spectrum is determined in an ultraviolet-visible absorption analyzer (U-4000, manufactured by Hitachi), and the emission spectrum is determined by using a He—Cd laser (excitation wavelength: 325 nm) as the excitation light source and a multi-channel detector (PMA-11, manufactured by Hamamatsu Photonics) as the detector. The results are summarized in Table 70.

TABLE 70

|  | Mobility (cm$^2$/Vs) | Absorption wavelength λ max (nm) | Emission wavelength λ max (nm) | Glass transition temperature (° C.) |
| --- | --- | --- | --- | --- |
| Compound of Example 1 | $1.1 \times 10^{-5}$ | 427 | 524 | 90 |
| Compound of Example 2 | $3.3 \times 10^7$ | 423 | 510 | 116 |
| Compound of Example 3 | $3.5 \times 10^{-5}$ | 410 | 509 | 119 |
| Compound of Example 4 | $4.3 \times 10^{-5}$ | 414 | 541 | 158 |
| Compound of Example 5 | $1.0 \times 10^{-4}$ | 425 | 517 | 125 |
| Compound of Example 6 | $4.8 \times 10^{-4}$ | 412 | 510 | 156 |
| Compound of Example 7 | $5.0 \times 10^{-5}$ | 420 | 535 | 143 |
| Comparative Example 1 (MEH-PPV) | $10^{-7}$ to $10^{-8}$ | 479 | 550 | 75 |

As is apparent from the results in Table 70, the thiophene-containing compounds and thiophene-containing compound polymers according to an aspect of the invention may have high mobility and favorable emission characteristics.

Preparative Example 1

Charge-Transporting Polyester (13)

A diamine 29 (following monomer (XIII)) is prepared according to the following method:

25.0 g of acetanilide, 64.4 g of methyl 4-iodophenylpropionate, 38.3 g of potassium carbonate, 2.3 g of copper sulfate pentahydrate, and 50 ml of n-tridecane are placed in a 500-ml three-necked flask, and the mixture is stirred under heat and nitrogen stream at 230° C. for 20 hours. After termination of the reaction, a solution of 15.6 g of potassium hydroxide in 300 ml of ethylene glycol is added thereto; the mixture is heated under reflux under nitrogen stream for 3.5 hours and then cooled to room temperature; and the reaction solution is poured into 1 L of distilled water and neutralized with hydrochloric acid, to give a crystalline precipitate. The crystal is collected by suction filtration, washed thoroughly with water, and transferred into a 1-L flask. After addition of 500 ml of toluene, the mixture is heated under reflux to remove water by azeotropic distillation; a solution of 1.5 ml of conc. sulfuric acid in 300 ml of methanol is added thereto; and the mixture is heated under reflux under nitrogen stream for 5 hours. After reaction, the product is extracted with toluene, and the organic layer is washed thoroughly with distilled water. Then after drying over anhydrous sodium sulfate, the solvent is removed under reduced pressure, and the residue is recrystallized from hexane, to give 36.5 g of DAA-1.

0.4 g of tetrakis(triphenyl)phosphine palladium, 15 ml of toluene, 5 g of 2,7-diiodo-9,9-dimethylfluorene, 6 ml of aqueous sodium hydrogen carbonate solution, 2 g of 5-chlorothiophene-2-boronic acid, and 5 ml of ethanol are placed in a 100-ml three-necked round-bottomed flask, and the mixture is heated under reflux in nitrogen environment for 4 hours. After termination of the reaction, the mixture is cooled to room temperature; the aqueous and organic layers are separated; and the organic layer is washed with aqueous saturated sodium chloride solution. Removal of the solvent under reduced pressure gives a crude product. It is purified by silica gel chromatography using hexane, to give 1.1 g of [intermediate 1].

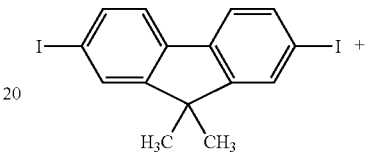

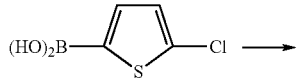

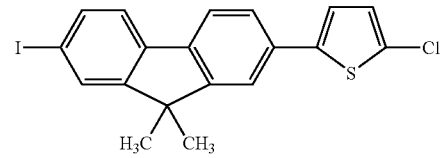

Intermediate 1

0.8 g of DAA-1, 1.1 g of [intermediate 1], 0.6 g of potassium carbonate, 0.1 g of copper sulfate pentahydrate, and 2 ml of o-dichlorobenzene are placed in a 25-ml three-necked flask, and the mixture is stirred under heat under nitrogen stream at 180° C. for 15 hours. After termination of the reaction, the mixture is cooled to 100° C. and dissolved in toluene; the insoluble matter is removed by Celite filtration while hot, and the filtrate is purified by silica gel column chromatography using ethyl acetate/hexane, to give 1.1 g of TAA-1.

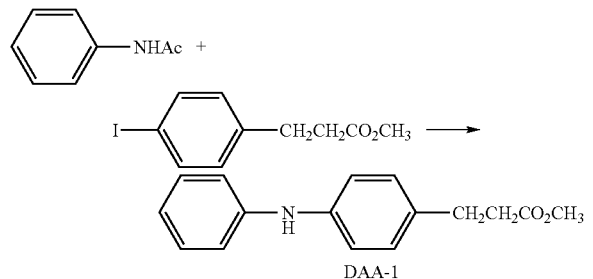

DAA-1

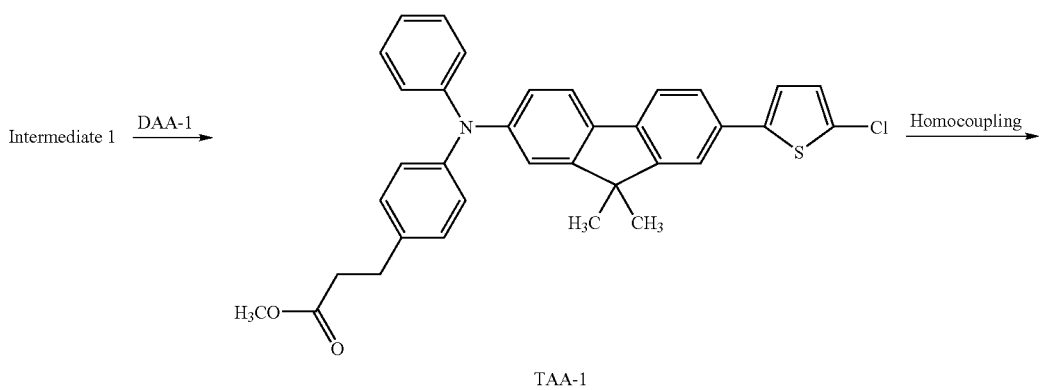

TAA-1

0.3 g of nickel chloride, 2.1 g of triphenylphosphine, and 4 ml of anhydrous DMF are place in a 25-ml three-necked flask; the mixture is heated to 50° C.; and, after addition of 0.1 g of zinc, the mixture is stirred under heat at 50° C. for 1 hour. Then, 1.0 g of TAA-1 and 3 ml of anhydrous DMF are added, and the mixture is stirred additionally for 2.5 hours. After termination of the reaction, the mixture is poured into 80 ml of water; after separation into aqueous and organic layers, the organic layer is washed and dried over anhydrous sodium sulfate, and removal of the solvent under reduced pressure gives a crude product. It is purified by silica gel column chromatography using ethyl acetate/hexane, to give 0.6 g of diamine 29 (yield 66%).

to room temperature, to give a Grignard reagent. Separately, 0.1 g of Pd (dppf)Cl$_2$, 3.6 g of 2,7-diiodo-9,9-dimethylfluorene, and 20 ml of toluene are placed in a 100-ml three-necked flask, and the Grignard reagent is added dropwise. After dropwise addition, the mixture is stirred at room temperature for 6 hours. After termination of the reaction, the mixture is made acidic by addition of hydrochloric acid and separated into aqueous and organic layers. The organic layer is washed with distilled water and dried over anhydrous sodium sulfate. The solvent is removed under reduced pressure, to give a crude product. The crude product is purified by silica gel chromatography using hexane, to give 1.1 g of [intermediate 2].

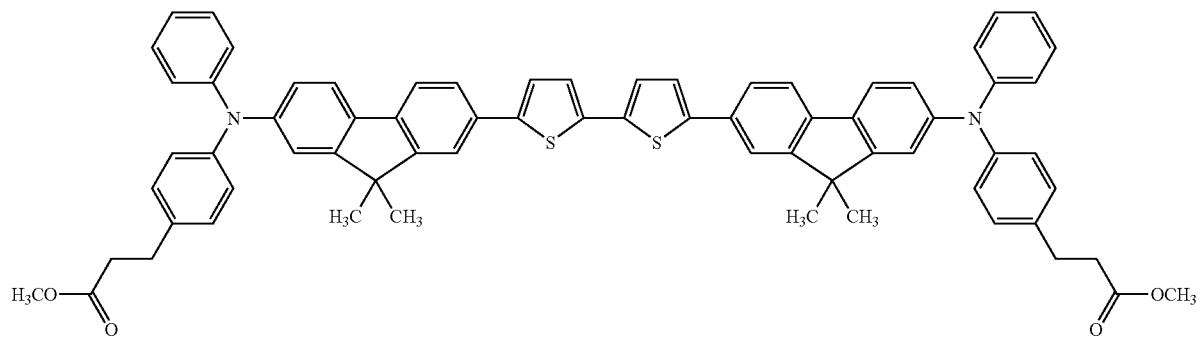

(XIII)

Then, 1.0 g. of diamine 29 (the monomer (XIII)), 10.0 ml of ethylene glycol and 0.02 g of tetrabutoxytitanium are placed in a 50-ml three-necked round-bottomed flask, and the mixture is stirred under heat under nitrogen stream at 200° C. for 6.5 hours. After confirming that the raw material diamine 29 (the monomer (XIII)) is consumed, the mixture is heated to 210° C. under a reduced pressure of 0.5 mm Hg and allowed to react for 4 hours while distilling off ethylene glycol. Then, the mixture is cooled to room temperature and dissolved in 50 ml of monochlorobenzene; the insoluble matter is removed by filtration through a polytetrafluoroethylene (PTFE) filter having an opening of 0.5 μm; and the filtrate is added dropwise into 500 ml of methanol while stirred, allowing precipitation of polymer. The polymer obtained is filtered, washed thoroughly with methanol, and dried, to give 1.1 g of the charge-transporting polyester (13) above. Molecular weight analysis by GPC gel-permeation chromatography (GPC) shows a Mw of $1.03 \times 10^5$ (in terms of styrene) and a Mn/Mw of 2.35, and thus, the polymerization degree p as determined from the monomer molecular weight is approximately 97.

Preparative Example 2

Charge-Transporting Polyester (52)

A diamine 141 (the following monomer (XIV)) is prepared according to the following method.

0.2 g of magnesium is placed in a 50-ml three-necked flask, baked with a burner, and then cooled to room temperature. 2 ml of ether, 3.1 g of 5-chloro-2-iodo-3-(2,4-dimethylphenyl) thiophene, and 8 ml of ether are then added thereto, and the mixture is heated under reflux for 15 minutes. After confirmation of consumption of magnesium, the mixture is cooled

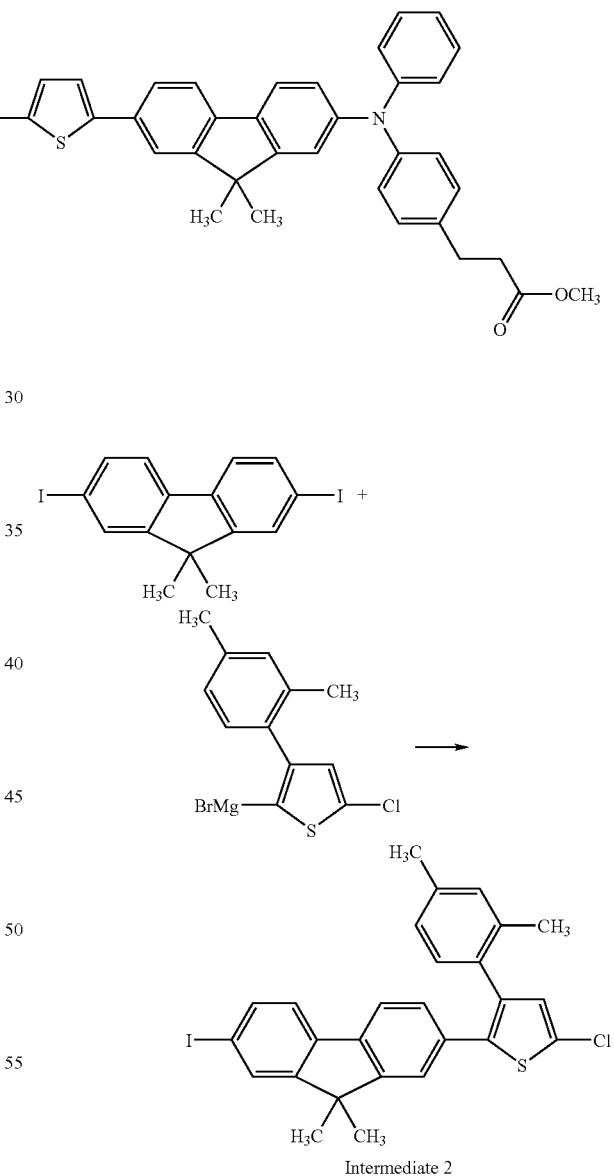

Intermediate 2

Then, coupling reaction with DAA-1 prepared in Preparative Example 1 is conducted in the same manner as Preparative Example 1, except that the [intermediate 2] is used instead of the [intermediate 1], to give TAA-2. The TAA-2 is homo-coupled in a similar manner to Preparative Example 1, to give a diamine 141.

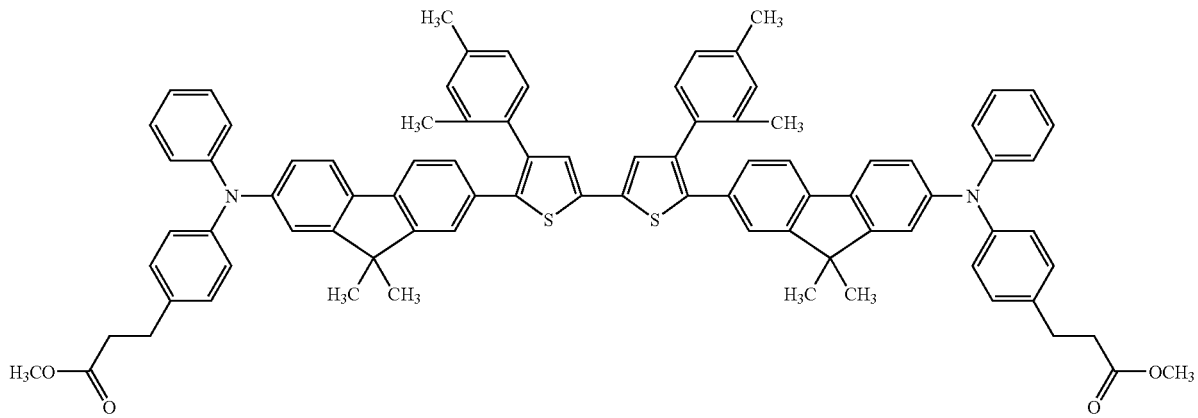

(XIV)

Then, 1.0 g of diamine 141 (the monomer (XIV)), 10.0 ml of ethylene glycol and 0.02 g of tetrabutoxytitanium are placed in a 50-ml three-necked round-bottomed flask, and the mixture is stirred under heat and nitrogen stream at 200° C. for 8 hours. After confirmation of consumption of the raw material diamine 141 (the monomer (XIV)) by TLC, the mixture is heated to 210° C. at a reduced pressure of 0.5 mm Hg additionally for 5 hours while distilling off ethylene glycol. The mixture is then cooled to room temperature and dissolved in 50 ml of monochlorobenzene; the insoluble matter is then removed by filtered through a 0.5-μm PTFE filter; and the filtrate is added dropwise into 500 ml of stirred methanol, to give a polymer precipitate. The polymer obtained is collected by filtration, washed thoroughly with methanol, and dried to give 0.8 g of a charge-transporting polyester (52). Molecular weight analysis by GPC showed a Mw of $1.05 \times 10^5$ (in terms of styrene) and an Mw/Mn of 2.89, and the polymerization degree p as determined from the monomer molecular weight is approximately 69.

Preparative Example 3

Charge-Transporting Polyester (57)

A diamine 147 (the following monomer (XV)) is first prepared according to the following method.

An [intermediate 2] is first prepared in a similar manner to Preparative Example 2.

2.2 g of 2-hexyl-5-(2-iodo-9,9-dimethylfluorenyl)thiophene, 0.9 g of acetamidophenylpropionic methyl ester, 0.9 g of potassium carbonate, 0.1 g of copper sulfate pentahydrate, and 3 ml of o-dichlorobenzene are placed in a 50-ml three-necked flask, and the mixture is heated under reflux under nitrogen stream for 16 hours. After termination of the reaction, the mixture is cooled to room temperature and dissolved in 100 ml of toluene; the insoluble matter is removed by filtration; and the filtrate is purified by silica gel column chromatography using an ethyl acetate/hexane liquid mixture, to give 1.9 g of DAA-3.

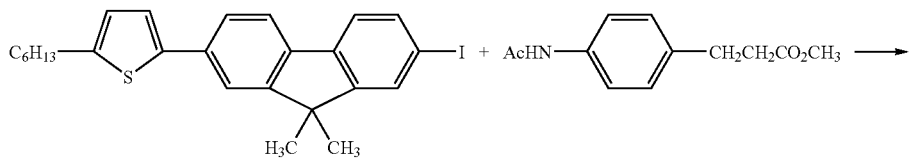

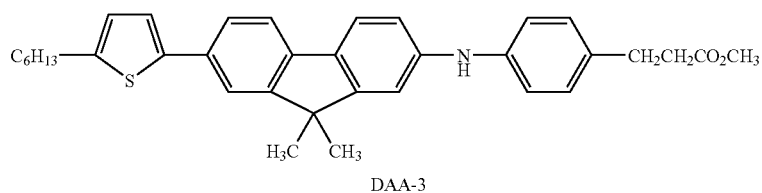

DAA-3

0.9 g of DAA-3, 1.1 g of [intermediate 2], 0.4 g of potassium carbonate, 0.1 g of copper sulfate pentahydrate, and 3 ml of o-dichlorobenzene are placed in a 50-ml three-necked flask, and the mixture is heated under reflux and under nitrogen stream at 180° C. for 24 hours. After termination of the reaction, the mixture is cooled to 100° C. and dissolved in 100 ml of toluene; the insoluble matter is removed by Celite filtration while hot; and the filtrate is purified by silica gel column chromatography using an ethyl acetate/hexane liquid mixture, to give 1.2 g of TAA-3.

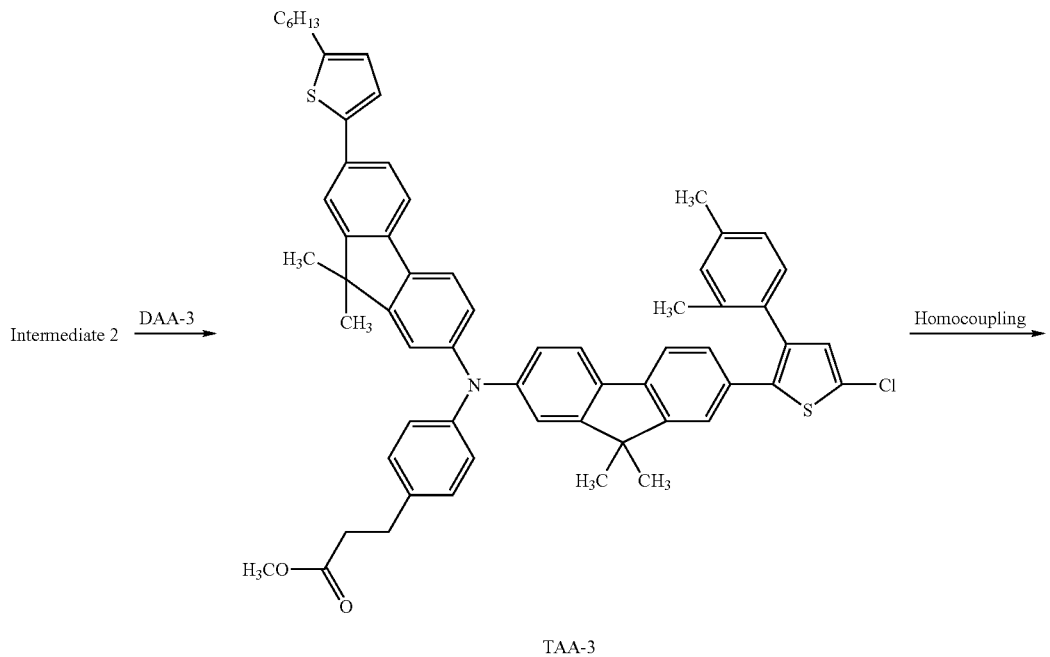

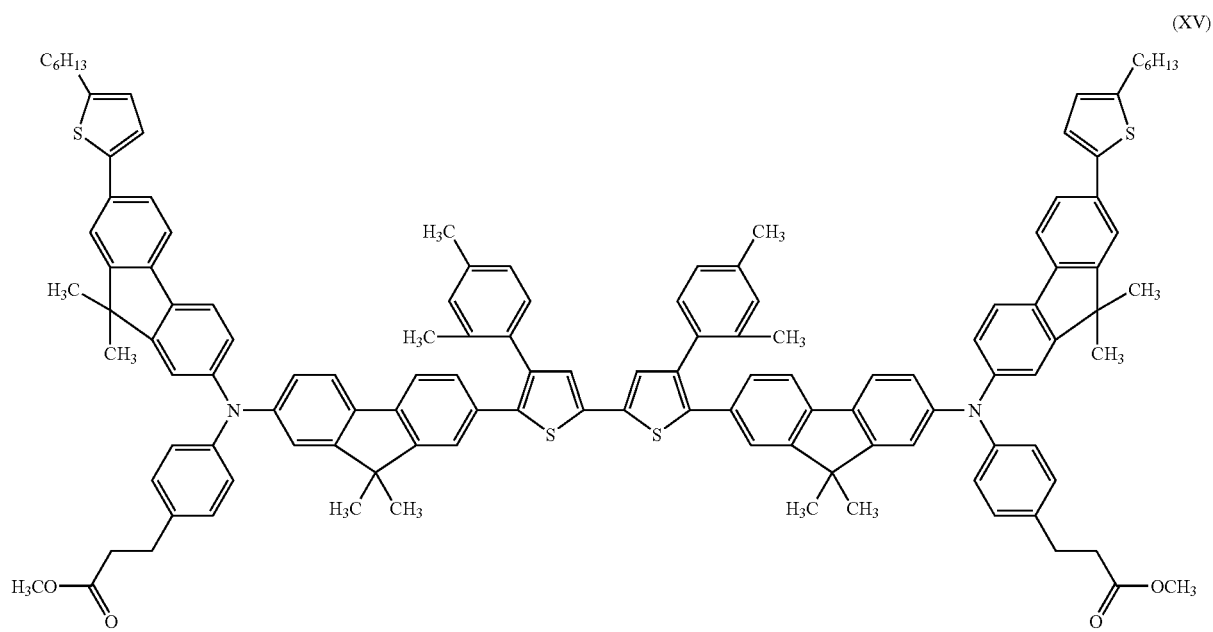

0.2 g of nickel chloride, 1.1 g of triphenylphosphine, and 5 ml of anhydrous DMF are placed in a 25-ml three-necked flask, and the mixture is heated to 50° C. After 0.1 g of zinc is added, the mixture is stirred at 50° C. for 1 hour. 0.7 g of TAA-3 is then added, and the mixture is stirred additionally for 2.5 hours. After termination of the reaction, the mixture is poured into 50 ml of water, and the precipitated solid is collected by suction filtration, to give a crude product. It is purified by silica gel column chromatography using an ethyl acetate/hexane mixture solution, to give 0.6 g of a diamine 147 (yield: 85%).

Then, 1.0 g of the diamine 147 (the monomer (XV)), 10.0 ml of ethylene glycol and 0.02 g of tetrabutoxytitanium are placed in a 50-ml three-necked round-bottomed flask, and the 0.2 g of nickel chloride, 1.1 g of triphenylphosphine, and 5 ml of anhydrous DMF are placed in a 25-ml three-necked flask, and the mixture is heated to 50° C. After 0.1 g of zinc is added, the mixture is stirred at 50° C. for 1 hour. 0.7 g of TAA-3 is then added, and the mixture is stirred additionally for 2.5 hours. After termination of the reaction, the mixture is poured into 50 ml of water, and the precipitated solid is collected by suction filtration, to give a crude product. It is purified by silica gel column chromatography using an ethyl acetate/hexane mixture solution, to give 0.6 g of a diamine mixture is stirred under heat and nitrogen stream at 200° C. for 7 hours. After confirmation of consumption of the raw material diamine 147 (the monomer (XV)), the mixture is heated to 200° C. under a reduced pressure of 0.5 mm Hg for 4 hours while distilling off ethylene glycol. Then, the mixture is cooled to room temperature and dissolved in 50 ml of monochlorobenzene; the insoluble matter is removed by filtration through a 0.5-μm PTFE filter; and the filtrate is added dropwise into 500 ml of stirred methanol, to give a polymer precipitate. The polymer obtained is collected by filtration, washed thoroughly with methanol, and dried, to give 0.9 g of a charge-transporting polyester (57). Molecular weight analysis by GPC showed a Mw of $8.73 \times 10^4$ (in terms of styrene) and a Mw/Mn of 2.95, and the polymerization degree p as determined from the monomer molecular weight is approximately 69.

Preparative Example 4

Charge-Transporting Polyester (27)

A diamine 70 (the following monomer (XVI)) is first prepared according to the following method.

0.2 g of magnesium is placed in a 50-ml three-necked flask, baked with a burner, and then cooled to room temperature. 2 ml of ether and 3.0 g of 5-chloro-2-iodo-3-(2,4-dimethylphenyl)thiophene are added thereto, and the mixture is heated under reflux for 15 minutes. After confirmation of consumption of magnesium, the mixture is cooled to room temperature, to give a Grignard reagent. Then, 0.1 g of $Pd(dppf)Cl_2$, 3.6 g of 2,7-diiodo-9,9-dimethylfluorene, and 20 ml of toluene are placed in a 100 ml three-necked flask, and the Grignard reagent is added dropwise thereto. After dropwise addition, the mixture is stirred at room temperature for 6.5 hours. After termination of the reaction, the mixture is made acidic by addition of hydrochloric acid and separated into aqueous and organic layers. The organic layer is washed with distilled water and dried over anhydrous sodium sulfate. The solvent is removed under reduced pressure, to give a crude product. The crude product is purified by silica gel chromatography using hexane, to give 1.3 g of [intermediate 4].

Then, the diamine 70 is prepared in the same manner as Preparative Example 2, except that the [intermediate 2] is replaced with the [intermediate 4].

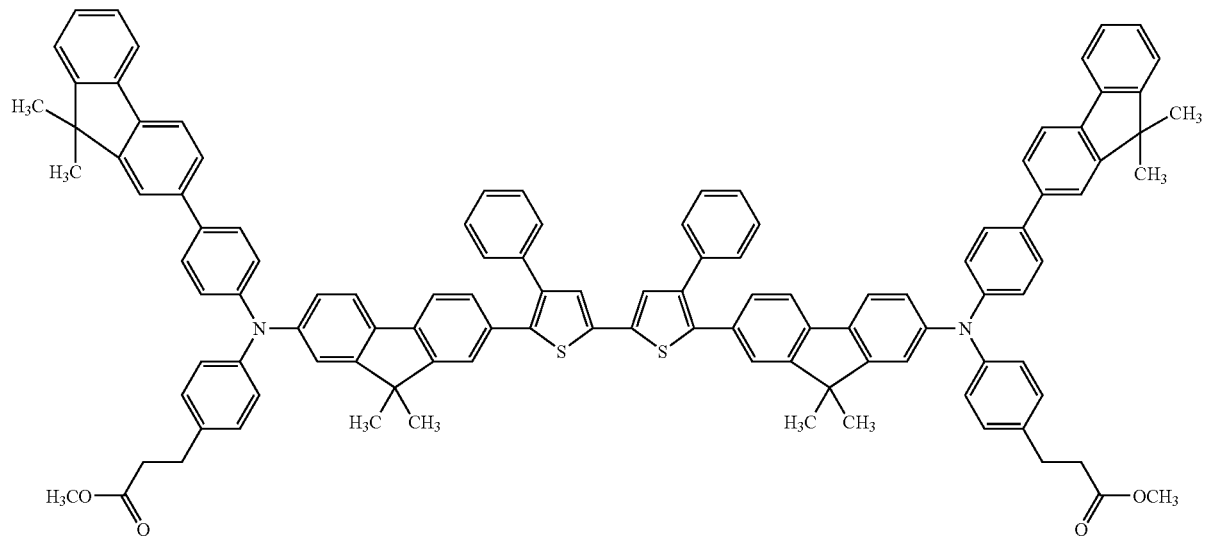

(XVI)

Then, 1.0 g of diamine 70 (the monomer (XVI), 10.0 ml of ethylene glycol and 0.02 g of tetrabutoxytitanium are placed in a 50-ml three-necked round-bottomed flask, and the mixture is stirred under heat and nitrogen stream at 200° C. for 5 hours. After confirmation of consumption of the diamine 70

(the monomer (XVI)), the mixture is heated to 210° C. at a reduced pressure of 0.5 mm Hg and allowed to react for 4 hours while distilling off ethylene glycol. The mixture is then cooled to room temperature and dissolved in 50 ml of monochlorobenzene; the insoluble matter is removed by filtration through a 0.5-μm PTFE filter; and the filtrate is added dropwise into to 500 ml of stirred methanol, to give a polymer precipitate. The polymer obtained is collected by filtration, washed thoroughly with methanol, and dried, to give 1.0 g of a charge-transporting polyester (27). Molecular weight analysis by GPC showed a Mw of $1.27 \times 10^5$ (in terms of styrene) and an Mw/Mn of 2.52, and the polymerization degree p as determined from the monomer molecular weight is approximately 80.

Preparative Example 5

Charge-Transporting Polyester (71)

A diamine 271 (the following monomer (XVII)) is first prepared according to the following method.

The diamine 271 is prepared in the same manner as Preparative Example 1, except that acetanilide is replaced with 4-bithienylacetanilide and 2,7-diiodo-9,9-dimethylfluorene is replaced with 2,7-diiodo-9,9-dihexylfluorene.

ture is stirred under heat and nitrogen stream at 200° C. for 6 hours. After confirmation of consumption of the diamine 271 (the monomer (XVII)), the mixture is heated to 210° C. at a reduced pressure of 0.5 mm Hg and allowed to react for 4 hours while distilling off ethylene glycol. The mixture is then cooled to room temperature and dissolved in 50 ml of monochlorobenzene; the insoluble matter is removed by filtration through a 0.5-μm PTFE filter; and the filtrate is added dropwise into to 500 ml of stirred methanol, to give a polymer precipitate. The polymer obtained is collected by filtration, washed thoroughly with methanol, and dried, to give 1.0 g of a charge-transporting polyester (71). Molecular weight analysis by GPC showed a Mw of $1.09 \times 10^5$ (in terms of styrene) and an Mw/Mn of 2.99, and the polymerization degree p as determined from the monomer molecular weight is approximately 60.

Preparative Example 6

Charge-Transporting Polyester (75)

A diamine 340 (the following monomer (XVIII)) is first prepared according to the following method.

DAA-4 is prepared in the same manner as Preparative Example 1, except that acetanilide is replaced with 4-(9,9-dimethylfluorenyl)acetanilide. Then, a diamine 340 is prepared in the same manner as Preparative Example 2, except that DAA-1 is replaced with the DAA-4.

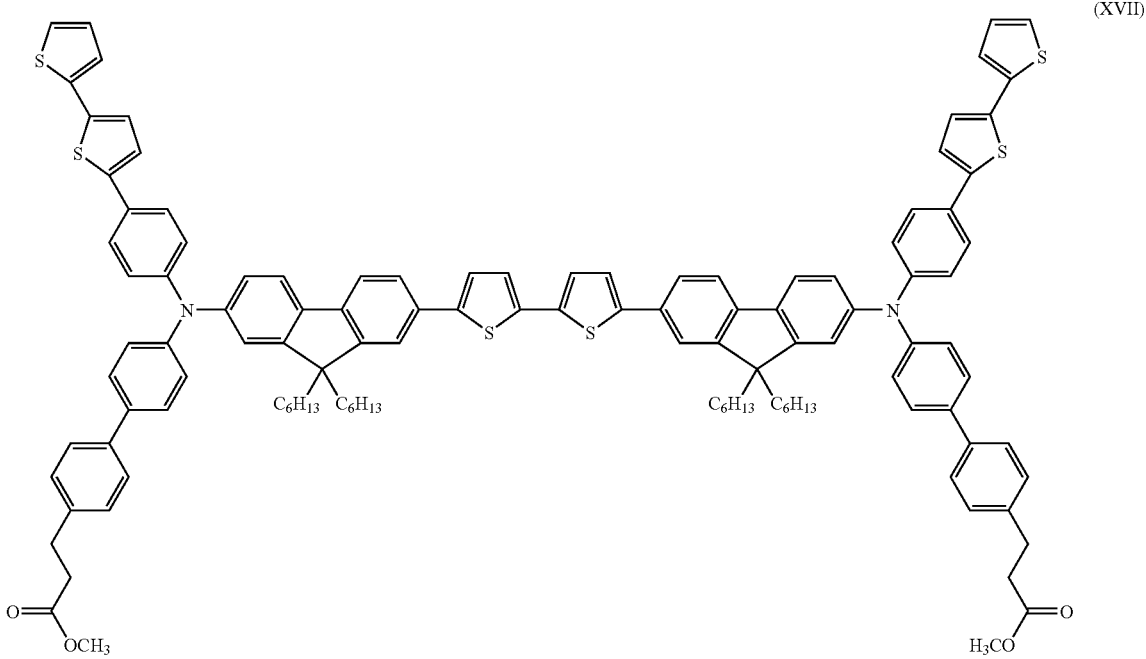

(XVII)

Then, 1.0 g of diamine 271 (the monomer (XVII)), 10.0 ml ethylene glycol and 0.02 g of tetrabutoxytitanium are placed in a 50-ml three-necked round-bottomed flask, and the mix-

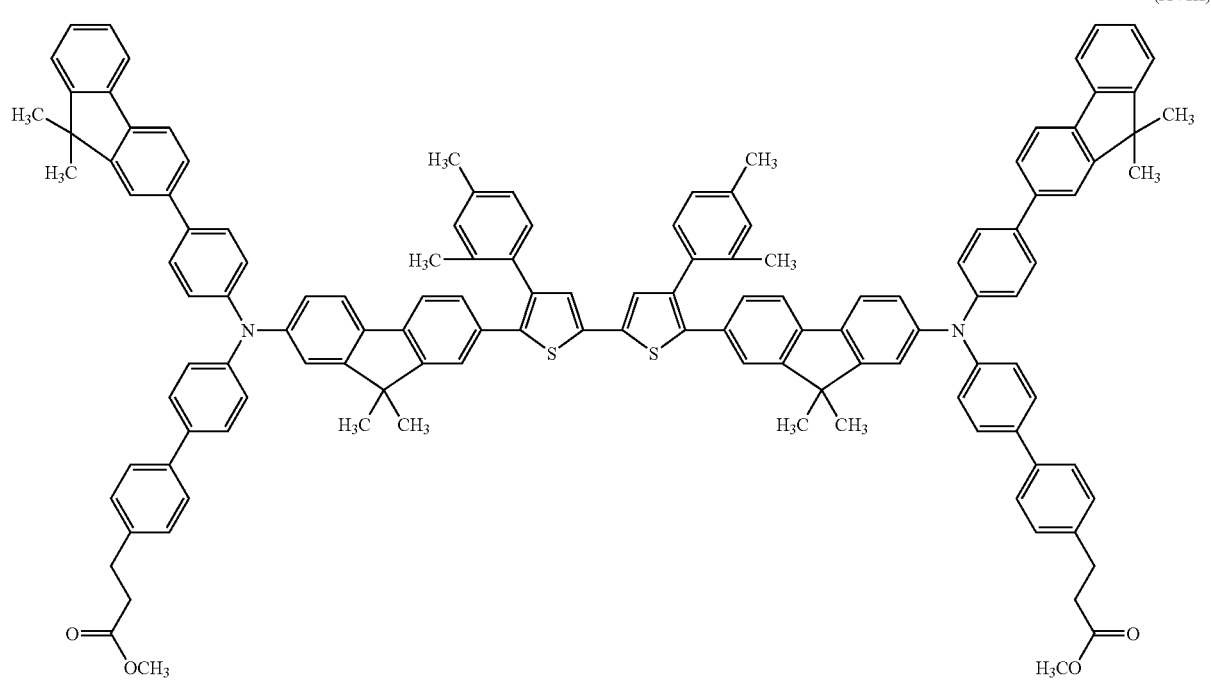

(XVIII)

Then, 1.0 g of the diamine 340 (the monomer (XVIII)), 10.0 ml of ethylene glycol and 0.02 g of tetrabutoxytitanium are placed in a 50-ml three-necked round-bottomed flask, and the mixture is stirred under heat and nitrogen stream at 200° C. for 6 hours. After confirmation of consumption of the diamine 340 (the monomer (XVIII)), the mixture is heated to 210° C. at a reduced pressure of 0.5 mm Hg and allowed to react for 4 hours while distilling off ethylene glycol. The mixture is then cooled to room temperature and dissolved in 50 ml of monochlorobenzene; the insoluble matter is removed by filtration through a 0.5-μm PTFE filter; and the filtrate is added dropwise into to 500 ml of stirred methanol, to give a polymer precipitate. The polymer obtained is collected by filtration, washed thoroughly with methanol, and dried, to give 1.0 g of the charge-transporting polyester (75). Molecular weight analysis by GPC showed a Mw of $1.29 \times 10^5$ (in terms of styrene) and an Mw/Mn of 2.88, and the polymerization degree p as determined from the monomer molecular weight is approximately 72.

Then, devices are prepared in the following manner, using the charge-transporting polyesters prepared by the methods above:

Example 8

A glass substrate of 2 mm in width on which an strip-shaped ITO electrode has been formed by etching is ultrasonicated sequentially in a neutral detergent solution, ultrapure water, acetone (for electronic industry, manufactured by Kanto Kagaku), and 2-propanol (for electronic industry, manufactured by Kanto Kagaku) in that order for five minutes each, whereby the glass substrate is cleaned; and, after drying, a 5% chlorobenzene solution containing a light-emitting polymer (following compound (XIX), polyfluorene-based) (Mw: ca. $10^5$) as the light-emitting material is prepared, filtered though a 0.1-μm polytetrafluoroethylene (PTFE) filter, and coated thereon by spin coating, to form a light-emitting layer having a thickness of 0.03 μm. After sufficient drying, a 5% dichloroethane solution containing the charge-transporting polyester (13) prepared in Preparative Example 1 above as the electron-transporting material is prepared, filtered though a 0.1-μm PTFE filter, and coated on the light-emitting layer by spin coating, to form an electron transport layer having a thickness of 0.03 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 $cm^2$.

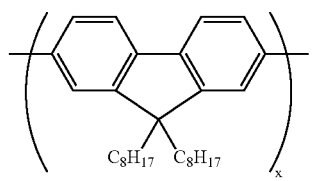

(XIX)

Example 9

After ultrasonication in a similar manner to Example 8, a 5% chlorobenzene solution containing the charge-transporting polymer (compound (IX-9), polyester-based) (Mw: ca. $10^5$) as the hole-transporting material which has been filtered through a 0.1-μm polytetrafluoroethylene (PTFE) filter is coated by spin coating on the buffer layer of the dried glass substrate on which a strip-shaped ITO electrode of 2 mm in width has been formed by etching, to form a hole transport layer having a thickness of 0.03 μm. After sufficient drying, sublimation-purified Alq3 (the compound (X-1)) as the light-emitting material placed in a tungsten board is vapor-deposited on the hole transport layer under vacuum, to form a light-emitting layer having a thickness of 0.05 μm. The degree of vacuum then is $10^{-5}$ Torr, and the board temperature is 300° C. In addition, a 5% dichloroethane solution containing the charge-transporting polyester (52) prepared in Preparative Example 2 above as the electron-transporting material is prepared, filtered through a 0.1-μm PTFE filter, and coated on the light-emitting layer by spin coating, to form an electron transport layer having a thickness of 0.03 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Example 10

An organic EL device is formed in the same manner as Example 9, except that a 5% chlorobenzene solution containing a light-emitting polymer (the compound (XIX), polyfluorene-based) (Mw: ca. $10^5$) as the light-emitting material is prepared, filtered through a 0.1-μm polytetrafluoroethylene (PTFE) filter, and coated by spin coating to form a light-emitting layer having a thickness of 0.03 μm.

Example 11

An organic EL device is formed in the same manner as Example 10, except that a 5% chlorobenzene solution containing the charge-transporting polyester (57) prepared in Preparative Example 3 as the hole-transporting material is prepared, filtered through a 0.1-μm polytetrafluoroethylene (PTFE) filter, and coated on the buffer layer by spin coating to form a hole transport layer having a thickness of 0.01 μm.

Example 12

A dried glass substrate of 2 mm in width on which an strip-shaped ITO electrode has been formed by etching is cleaned by ultrasonication in the same manner as in Example 8. A 5% chlorobenzene solution containing the charge-transporting polyester (57) prepared in Preparative Example 3 as the hole-transporting material is prepared, filtered through a 0.1-μm polytetrafluoroethylene (PTFE) filter, and coated on the buffer layer by spin coating on the glass substrate to form a hole transport layer having a thickness of 0.01 μm. After sufficient drying, sublimation-purified Alq3 (the compound (X-1)) as the light-emitting material placed in a tungsten board is vapor-deposited on the hole transport layer under vacuum, to form a light-emitting layer having a thickness of 0.05 μm. The degree of vacuum then is $10^{-5}$ Torr, and the board temperature is 300° C. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Example 13

An organic EL device is formed in the same manner as Example 12, except that a 5% chlorobenzene solution containing a light-emitting polymer (following compound (XX), PPV-based) (Mw: ca. $10^5$) as the light-emitting material is prepared, filtered through a 0.1-μm polytetrafluoroethylene (PTFE) filter, and coated by spin coating to form a light-emitting layer having a thickness of 0.03 μm.

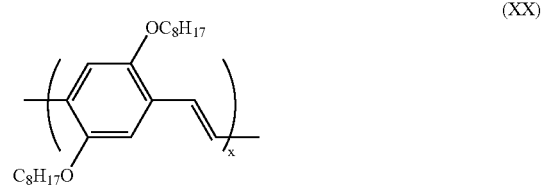

Example 14

A dried glass substrate of 2 mm in width on which an strip-shaped ITO electrode has been formed by etching is cleaned by ultrasonication in the same manner as in Example 8. A 10% chlorobenzene solution containing 0.5 part of the charge-transporting polyester (27) prepared in Preparative Example 4 and 0.1 part of the light-emitting polymer (compound (XX), PPV-based) (Mw: ca. $10^5$) as the charge-transporting materials is prepared, filtered through a 0.1-μm polytetrafluoroethylene (PTFE) filter, and coated by spin coating on the glass substrate, to form a light-emitting layer having electric charge-transporting ability and having a thickness of 0.05 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Example 15

A dried glass substrate of 2 mm in width on which an strip-shaped ITO electrode has been formed by etching is cleaned by ultrasonication in the same manner as in Example 8. A 10% chlorobenzene solution containing 0.5 part of the charge-transporting polyester (71) prepared in Preparative Example 5 and 0.1 part of the light-emitting polymer (compound (XX), PPV-based) (Mw: ca. $10^5$) as the charge-transporting materials is prepared, filtered through a 0.1-μm polytetrafluoroethylene (PTFE) filter, and coated by spin coating on the glass substrate, to form a light-emitting layer having electric charge-transporting ability and having a thickness of 0.05 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Example 16

A dried glass substrate of 2 mm in width on which an strip-shaped ITO electrode has been formed by etching is cleaned by ultrasonication in the same manner as in Example 8. A 10% chlorobenzene solution containing 0.5 part of the charge-transporting polyester (75) prepared in Preparative Example 6 and 0.1 part of the light-emitting polymer (compound (XX), PPV-based) (Mw: ca. $10^5$) as the charge-transporting materials is prepared, filtered through a 0.1-μm polytetrafluoroethylene (PTFE) filter, and coated by spin coating on the glass substrate, to form a light-emitting layer having electric charge-transporting ability and having a thickness of 0.05 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Example 17

A glass substrate of 2 mm in width on which an strip-shaped ITO electrode has been formed by etching is ultrasonicated sequentially in a neutral detergent solution, ultrapure water, acetone (for electronic industry, manufactured by Kanto Kagaku), and 2-propanol (for electronic industry, manufactured by Kanto Kagaku) in that order for five minutes each, whereby the glass substrate is cleaned; and, after drying, a 5% chlorobenzene solution containing a light-emitting polymer (the above compound (XIX), polyfluorene-based) (Mw: ca. $10^5$) as the light-emitting material is prepared, filtered though a 0.1-μm polytetrafluoroethylene (PTFE) filter, and coated thereon by inkjet printing method, to form a light-emitting layer having a thickness of 0.03 μm. After sufficient drying, a 5% dichloroethane solution containing the charge-transporting polyester (13) prepared in Preparative Example 1 above as the electron-transporting material is prepared, filtered though a 0.1-μm PTFE filter, and coated on the light-emitting layer by inkjet printing method, to form an electron transport layer having a thickness of 0.03 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Comparative Example 2

A glass substrate of 2 mm in width on which an strip-shaped ITO electrode has been formed by etching is ultrasonicated sequentially in a neutral detergent solution, ultrapure water, acetone (for electronic industry, manufactured by Kanto Kagaku), and 2-propanol (for electronic industry, manufactured by Kanto Kagaku) in that order for five minutes each, whereby the glass substrate is cleaned; and, after drying, a 5% chlorobenzene solution containing a light-emitting polymer (the above compound (XIX), polyfluorene-based) (Mw: ca. $10^5$) as the light-emitting material is prepared, filtered though a 0.1-μm polytetrafluoroethylene (PTFE) filter, and coated thereon by spin coating, to form a light-emitting layer having a thickness of 0.03 μm. After sufficient drying, an electron transport layer having a thickness of 0.05 μm made of the compound (VIII-1) as the electron-transporting material is formed by vacuum deposition. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Comparative Example 3

A dried glass substrate of 2 mm in width on which an strip-shaped ITO electrode has been formed by etching is cleaned by ultrasonication in the same manner as in Comparative Example 2. A hole transport layer having a thickness of 0.05 μm made of the compound (IX-2) as the hole-transporting material, a light-emitting layer having a thickness of 0.065 μm made of the sublimation-purified Alq3 (the compound (X-1)) as the light-emitting material, and an electron transport layer having a thickness of 0.05 μm made of the compound (VIII-1) as the electron-transporting material are formed in that order on the glass substrate. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Comparative Example 4

A dried glass substrate of 2 mm in width on which an strip-shaped ITO electrode has been formed by etching is cleaned by ultrasonication in the same manner as in Comparative Example 2. A hole transport layer having a thickness of 0.05 μm made of the compound (IX-2) as the hole-transporting material is formed on the glass substrate by vacuum deposition. Then, a 5% chlorobenzene solution containing the light-emitting polymer (the compound (XX), PPV-based) (Mw: ca. $10^5$) as the light-emitting material is prepared. The chlorobenzene solution was filtered through a 0.1-μm polytetrafluoroethylene (PTFE) filter, and was coated on the hole transport layer by spin coating, and was sufficiently dried to form a light-emitting layer having a thickness of 0.03 μm. An electron transport layer having a thickness of 0.05 μm made of the compound (VIII-1) as the electron-transporting material is formed by vacuum deposition. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Comparative Example 5

A dried glass substrate of 2 mm in width on which an strip-shaped ITO electrode has been formed by etching is cleaned by ultrasonication in the same manner as in Comparative Example 2. A hole transport layer having a thickness of 0.05 μm made of the compound (IX-2) as the hole-transporting material and a light-emitting layer having a thickness of 0.065 μm made of sublimation-purified Alq3 (compound (X-1)) as the light-emitting material are formed on the glass substrate by vacuum deposition in this order. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Comparative Example 6

A dried glass substrate of 2 mm in width on which an strip-shaped ITO electrode has been formed by etching is cleaned by ultrasonication in the same manner as in Comparative Example 2. A hole transport layer having a thickness of 0.05 μm made of the compound (IX-2) as the hole-transporting material is formed on the glass substrate by vacuum deposition. Then, a 5% chlorobenzene solution containing a light-emitting polymer (the compound (XX), PPV-based) (Mw≈105) as the light-emitting material is prepared, filtered through a 0.1-μm polytetrafluoroethylene (PTFE) filter, coated by spin coating, and dried sufficiently to form a light-emitting layer having a thickness of 0.03 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

Comparative Example 7

A dried glass substrate of 2 mm in width on which an strip-shaped ITO electrode has been formed by etching is cleaned by ultrasonication in the same manner as in Comparative Example 2. A 10% dichloroethane solution containing 1 part of the compound (IX-2) as the hole-transporting material, 1 part of the sublimation-purified Alq3 (the compound (X-1)) as the light-emitting material, and 1 part of polymethyl methacrylate (PMMA) as the binder resin is prepared, filtered through a 0.1-μm polytetrafluoroethylene (PTFE) filter, and coated on the glass substrate by dipping, to form a light-emitting layer having electric charge-transporting ability and having a thickness of 0.05 μm. Finally, a Mg—Ag alloy is co-deposited thereon to form a back electrode having a width of 2 mm and a thickness of 0.15 μm such that the back electrode intersects with the ITO electrode. The effective area of the organic EL device formed is 0.04 cm$^2$.

(Evaluation)

A DC voltage is applied to each of the obtained organic EL devices with the ITO electrode serving as the positive electrode and the Mg—Ag side serving as the negative electrode under vacuum [$133.3 \times 10^{-3}$ Pa ($10^{-5}$ Torr)]. The start-up voltage, the maximum brightness, and the drive current density at the maximum brightness are determined, and the measurement results are summarized in the following Table.

The emission lifetime of each organic EL device is also determined under dry nitrogen. In measurement of the emission lifetime, the time the brightness takes to decline from the initial value to half of the initial value when operated with a small current that gives an initial brightness of 50 cd/cm$^2$ is designated as the device lifetime (hour). The device lifetime determined is also shown in the following Table.

TABLE 71

| | Start-up voltage (cd/m$^2$) | Maximum brightness (cd/m$^2$) | Drive current density (mA/m$^2$) | Device lifetime (hour) |
|---|---|---|---|---|
| Example 8 | 4.1 | 1065 | 7.3 | 78 |
| Example 9 | 3.8 | 1079 | 7.0 | 88 |
| Example 10 | 4.2 | 1055 | 6.5 | 74 |
| Example 11 | 3.8 | 1047 | 7.2 | 69 |
| Example 12 | 4.0 | 1036 | 7.0 | 68 |
| Example 13 | 3.6 | 1088 | 6.4 | 90 |
| Example 14 | 3.6 | 1072 | 6.6 | 75 |
| Example 15 | 3.7 | 1030 | 6.5 | 74 |
| Example 16 | 3.9 | 1025 | 6.9 | 86 |
| Example 17 | 4.0 | 998 | 7.5 | 75 |
| Comparative Example 2 | 4.4 | 800 | 7.6 | 33 |
| Comparative Example 3 | 4.7 | 980 | 6.8 | 45 |
| Comparative Example 4 | 3.9 | 1010 | 7.5 | 48 |
| Comparative Example 5 | 4.7 | 860 | 7.9 | 39 |
| Comparative Example 6 | 4.4 | 900 | 7.6 | 34 |
| Comparative Example 7 | 6.2 | 680 | 10.7 | 35 |

The results in Table 71 reveal that each of the charge-transporting polyesters having a repeating structure containing at least one structure selected from the structures represented by formulae (I-1) and (I-2) as the partial structure has an ionization potential and a charge mobility suitable for use in organic electroluminescent devices and may give a favorable thin film, for example, by spin coating or dipping. The charge-transporting polyesters also raise charge injecting and transporting efficiency, and thus, may give a thin film improved in electric charge balance and consistently superior in brightness and efficiency. Thus, the organic electroluminescent devices according to an aspect of the invention are free from defects such as pinholes, allows easy expansion in size and shows excellent durability and light emission characteristics.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

All publications, patent applications, and technical standards mentioned in this specification are herein incorporated by reference to the same extent as if each individual publication, patent application, or technical standard was specifically and individually indicated to be incorporated by reference.

What is claimed is:

1. A thiophene-containing compound represented by the following formula (X-1):

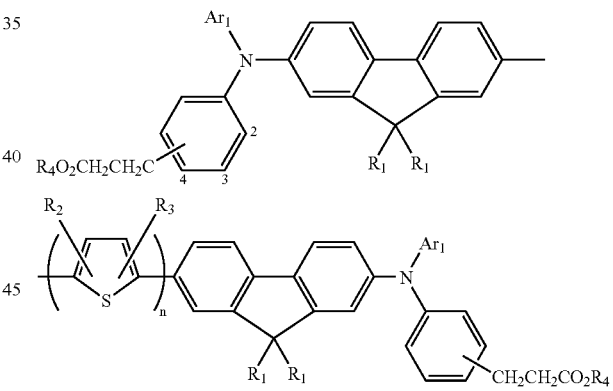

Formula (X-1)

in formula (X-1), Ar$_1$ representing a substituted or unsubstituted monovalent aromatic group; R$_1$ to R$_4$ each independently representing a hydrogen atom, a substituted or unsubstituted alkyl group, a substituted or unsubstituted aryl group, or a substituted or unsubstituted aralkyl group; and n representing an integer of 1 to 5.

* * * * *